(12) United States Patent
Cuevas et al.

(10) Patent No.: US 7,524,956 B2
(45) Date of Patent: Apr. 28, 2009

(54) HEMISYNTHETIC METHOD AND NEW COMPOUNDS

(75) Inventors: Carmen Cuevas, Madrid (ES); Marta Perez, Madrid (ES); Andres Francesch, Madrid (ES); Carolina Fernandez, Madrid (ES); Jose Luis Chicharro, Madrid (ES); Pilar Gallego, Madrid (ES); Maria Zarzuelo, Madrid (ES); Fernando de Calle, Madrid (ES); Ignacio Manzanares, Madrid (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 11/774,890

(22) Filed: Jul. 9, 2007

(65) Prior Publication Data

US 2008/0045713 A1 Feb. 21, 2008

Related U.S. Application Data

(63) Continuation of application No. 09/979,404, filed as application No. PCT/GB00/01852 on May 15, 2000, now Pat. No. 7,241,892.

(30) Foreign Application Priority Data

| May 14, 1999 | (GB) | ................................ | 9911345.8 |
| Aug. 2, 1999 | (GB) | ................................ | 99818178.6 |
| Oct. 6, 1999 | (GB) | ................................ | 9923632.5 |
| Jan. 17, 2000 | (GB) | ................................ | 0001063.7 |

(51) Int. Cl.
C07D 471/22 (2006.01)
C07D 487/22 (2006.01)
A61K 31/496 (2006.01)

(52) U.S. Cl. ...................... 544/338; 544/342
(58) Field of Classification Search ................. 544/338, 544/342
See application file for complete search history.

(56) References Cited

U.S. PATENT DOCUMENTS

| 4,400,752 | A | 8/1983 | Chabrolle | 360/112 |
| 5,089,273 | A | 2/1992 | Rinehart et al. | 424/520 |
| 5,149,804 | A | 9/1992 | Rinehart et al. | 540/466 |
| 5,256,663 | A | 10/1993 | Rinehart et al. | 514/250 |
| 5,478,932 | A | 12/1995 | Rinehart et al. | 540/466 |
| 5,654,426 | A | 8/1997 | Rinehart et al. | 540/466 |
| 5,721,362 | A | 2/1998 | Corey et al. | 540/466 |
| 5,985,876 | A | 11/1999 | Rinehart et al. | 514/250 |
| 6,124,292 | A | 9/2000 | Corey | 514/250 |
| 6,124,293 | A | 9/2000 | Rinehart et al. | |
| 6,316,214 | B1 | 11/2001 | Rinehart et al. | 435/25 |
| 6,348,467 | B1 | 2/2002 | Corey | 514/250 |
| 6,686,470 | B2 | 2/2004 | Danishefsky et al. | |
| 6,867,334 | B2 | 3/2005 | Floriano et al. | |
| 7,247,629 | B2 | 7/2007 | Manzanares et al. | |
| 2003/0216397 | A1 | 11/2003 | Flores et al. | |
| 2004/0002602 | A1 | 1/2004 | Francesch et al. | |
| 2004/0019056 | A1 | 1/2004 | Manzanares et al. | |

FOREIGN PATENT DOCUMENTS

| EP | 0 309 477 B1 | 11/1991 |
| JP | 59-225189 | 12/1984 |
| JP | 59225189 | * 12/1984 |
| JP | 60-84288 | 5/1985 |
| WO | WO 87/07610 | 12/1987 |

(Continued)

OTHER PUBLICATIONS

Arai, T. et al., "The Structure of a Novel Antitumor Antibiotic, Saframycin A", *Experientia*, vol. 36, pp. 1025-1027 (1980).

(Continued)

*Primary Examiner*—Kahsay T Habte
(74) *Attorney, Agent, or Firm*—Fish & Richardson P.C.

(57) ABSTRACT

Methods are provided for preparing a compound with a fused ring structure of formula (XIV) which comprises one or more reactions starting from a 21-cyano compound of formula (XVI) where typically; $R^1$ is an amidomethylene group or an acyloxymethylene group; $R^5$ and $R^8$ are independently chosen from —H, —OH or —OCOCH$_2$OH, or $R^5$ and $R^8$ are both keto and the ring A is a p-benzoquinone ring; $R^{14a}$ and $R^{14b}$ are both —H ozone is —H and the other is —OH, —OCH$_3$ or —OCH$_2$CH$_3$, or $R^{14a}$ and $R^{14b}$ together form a keto group; and $R^{15}$ and $R^{18}$ are independently chosen from —H or —OH, or $R^5$ and $R^8$ are both keto and the ring A is a p-benzoquinone ring. In modified starting materials, the 21-cyano group can be replaced by other groups introduced using nucleophilic reagents.

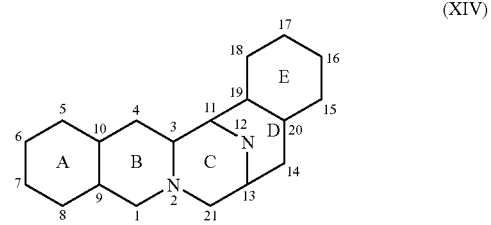

(XIV)

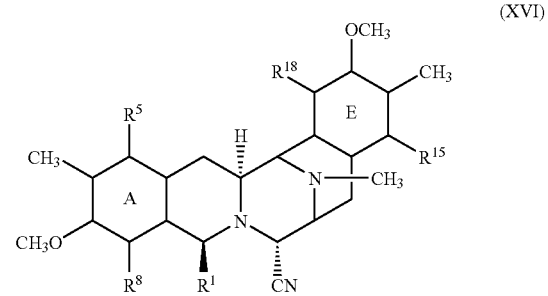

(XVI)

6 Claims, No Drawings

FOREIGN PATENT DOCUMENTS

| WO | WO 92/09607 | 6/1992 |
| --- | --- | --- |
| WO | WO 98/12198 | 3/1998 |
| WO | WO 98/46080 | 10/1998 |
| WO | WO 99/51238 | 10/1999 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |
| WO | WO 01/87895 | 11/2001 |

OTHER PUBLICATIONS

Arai, Tadashi et al., "Increased Production of Saframycin A and Isolation of Saframycin S", *The Journal of Antibiotics*, vol. XXXIII, No. 9, pp. 951-960 (1980).

Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).

Arai, Tadashi et al., "Isoquinolineinones from Actinomycetes and Sponges", *The Alkaloids Chemistry and Pharmacology*, vol. XXI, pp. 56-100 (1983).

Arai, Tadashi et al., "New Antibiotics, Safraycins A, B, C, D and E", *The Journal of Antibiotics*, vol. XXX, No. 11, pp. 1015-1018 (1977).

Arai, Tadashi et al., "Increased Production of Saframycin A and Isolation of Saframycin S", *The Journal of Antibiotics*, vol. XXXIII, No. 9, pp. 951-960 (1980).

Asaoka, Takemitsu et al., "A New Saframycin, Saframycin R", *The Journal of Antibiotics*, vol. XXXV, No. 12, pp. 1708-1710 (1982).

Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).

Brown, J.M., "NCI's Anticancer Drug Screening Program May Not Be Selecting for Clinically Active Compounds," Oncol. Res. 9(5):213-215 (1997).

Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).

Calabresi et al., "Chemotherapy of Neoplastic Diseases", Goodman & Gilman's The Pharmacological Basis of Therapeutics, 9th ed. New York: McGraw-Hill, 1996, pp. 1225-1229.

Cecil Textbook of Medicine (Bennet, J.C. and Plum, F., eds.) 20th Edition, vol. 1, pp. 1004-1010, (1996).

Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).

Corey, E.J. et al., "Enantioselective Total Synthesis of Ecteinascidin 743", *Journal of the American Chemical Society*, vol. 118, No. 38, pp. 9202-9203 (1996).

Cuevas, Carmen et al., "Synthesis of Exteinascidin ET-743 and Phthalascidin Pt-650 from Cyanosafracin B", *Organic Letters*, vol. 2, No. 16, pp. 2545-2548 (2000).

Draetta, G. and Pagano, M., "Annual Reports in Medicinal Chemistry, vol. 31," Academic Press, San Diego, pp. 241-246 (1996).

Eckhardt, S.G. et al., "Activity of eceteinascidin, a novel marine cytotoxic, against primary human tumor colony-forming units", *Proceedings of the American Association for Cancer Research*, vol. 37, #2791, pp. 409 (1996).

Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).

Flam, Faye, "Chemical Prospectors Scour the Seas for Promising Drugs", *Science*, vol. 266, pp. 1324-1325 (1994).

Frincke, James M. et al., "Antimicrobial Metabolites of the Sponge *Reniera* sp." *Journal of the American Chemical Society*, vol. 104, pp. 265-269 (1982).

Fukuyama, Tohru et al., "Total Synthesis of (±)-Saframycin A", *Journal of American Chemical Society*, vol. 112, pp. 3712-3713 (1990).

Fukuyama, Tohru et al., "Stereocontrolledl Total Synthesis of (±)-Saframycin B", *Journal of American Chemical Society*, vol. 104, pp. 4957-4958 (1982).

Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge *Reniera* sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Kania, Robert S., "The First Enantioselective Total Syntheses of Dolabellatrienone and Ecteinascidin 743", Ph.D. Thesis, Harvard University, Sep. 1997, pp. 1-225.

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kubo et al., "Stereoselective Total Synthesis of (±) Saframycim B", J. Org. Chem., vol. 53, No. 18, 1988, pp. 4295-4310.

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Ito, Yoichiro, "High-Speed Countercurrent Chromatography", *Critical Reviews in Analytical Chemistry*, vol. 17, No. 1, pp. 65-143 (1986).

Lichter, W. et al., "Biological Activities Exerted by Extracts of Ecteinascidia Turbinata", *Food and Drugs from the Sea Proceedings*, pp. 118-127 (1972).

Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).

Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).

Martinez, Eduardo J. et al., "Phthalascidin, a synthetic antitumor agent with potency and mode of action comparable to ecteinascidin 743", *Chemistry*, vol. 96, pp. 3496-3501 (1999).

Martinez et al., "Enantioselective Synthesis of Saframycin A and Evaluation of Antitumor Activity Relative to Ecteinascidin/Saframycin Hybrids", Organic Letters, 1(7):75-77 (1999).

Martinez et al., "A New, More Effficient, and Effective Process for the Synthesis of a Key Pentacyclic Intermediate for Production of Ecteinascidin and Phthalascidin Antitumor Agents", Organic Letters, 2(7):993-996 (2000).

Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Moore et al., "NMR-Based Model of an Ecteinascidin 743-DNA Adduct", J/ Am. Chem. Soc., vol. 119, 1997, pp. 5475-5476.

Myers et al., "A Concise, Stereocontrolled Synthesis of (−)-Saframycin A by the Directed Condensation of α-Amino Aldehyde Precursors", J. Am. Chem. Soc., 121:10828-10829 (1999).

Nakagawa, Masako et al., "Total Synthesis of (+)-Eudistomin L and (+)-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35.

Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).

Remers, William A. *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Bioactive Compounds from Aquatic and Terrestrial Sources", *Journal of Natural Products*, vol. 53, No. 4, pp. 771-792 (1990).

Rinehart, Kenneth L., "Antitumor Compounds from Tunicates", *Medicinal Research Reviews*, vol. 20, No. 1, pp. 1-27 (2000).

Rinehard, Kenneth L. et al., "Ecteinascidins 729, 743, 759A , 759B, and 770: Potent Antitumor Agents from the Caribbean Tunicate Exteinascidia Turbinata", *The Journal of Organic Chemistry*, vol. 55, No. 15, pp. 4512-4515 (1990).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Shamma, Maurice et al., *Carbon-13 NMR Shift Assignments of Amines and Alkaloids*, pp. 206 (1979).

Sparidans, Rolf W. et al., "Search for metabolites of ecteinascidin 743, a novel, marine-derived, anti-cancer agent, in man." *Anti-Cancer Drugs*, vol. 12, pp. 653-666.

Still, W. Clark et al., "Rapid Chromatographic Technique for Preparative Separations with Moderate Resolution", *Journal of Organic Chemistry*, vol. 43, No. 14, pp. 2923-2925 (1978).

Takahaski, Katsuhiro, "New Antibiotics, Saframycins A, B, C, D and E", *The Journal of Antibiotics*, vol. XXX, No. 11, pp. 1015-1018 (1977).

Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Trowitzsch-Kienast, Wolfram et al., "Isolierung und Strukturaufklarung der Saframycine Mx 1 und Mx 2, neue antitumoraktive Antibiotika aus Myxococcus xanthus", *Liebigs Ann. Chem.*, vol. XXXV, pp. 475-481 (1988).

Valoti et al. Clin. Cancer Res. 4(8): 1977-83 (1998).

Witten, Jane L. et la., "Structures of Two Cockroach Neuropeptides Assigned by Fast Atom bombardment Mass Spectrometry", *Biochemical and Biophysical Research Communications*, vol. 124, No. 2, pp. 350-358 (1984).

Wright, Amy E. et al., "Antitumor Tetrahydroisoquinoline Alkaloids from the Colonial Ascidian Ecteinascidia Turbinata", *The Journal of Organic Chemistry*, vol. 55, no. 15, pp. 4508-4512 (1990).

Yazawa, Katsukiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).

Zmijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

\* cited by examiner

HEMISYNTHETIC METHOD AND NEW COMPOUNDS

CROSS-REFERENCE TO RELATED APPLICATION

This application is a continuation of U.S. Ser. No. 09/979,404, filed Mar. 6, 2002, which is the National Stage of International Application No. PCT/GB00/01852 filed on May 15, 2000, which claims priority from United Kingdom Patent Application No. 0001063.7 filed on Jan. 17, 2000, United Kingdom Patent Application No. 9923632.5 filed on Oct. 6, 1999, United Kingdom Patent Application No. 9918178.6 filed on Aug. 2, 1999, and United Kingdom Patent Application No. 9911345.8 filed on May 14, 1999, all of which are incorporated herein by reference in their entirety.

The present invention relates to synthetic methods, and in particular it relates to hemisynthetic methods.

BACKGROUND OF THE INVENTION

European Patent 309,477 relates to ecteinascidins 729, 743, 745, 759A, 759B and 770. The ecteinascidin compounds are disclosed to have antibacterial and other useful properties. Ecteinascidin 743 is now undergoing clinical trials as an antitumour agent.

Ecteinascidin 743 has a complex tris(tetrahydroisoquinolinephenol) structure of the following formula (I):

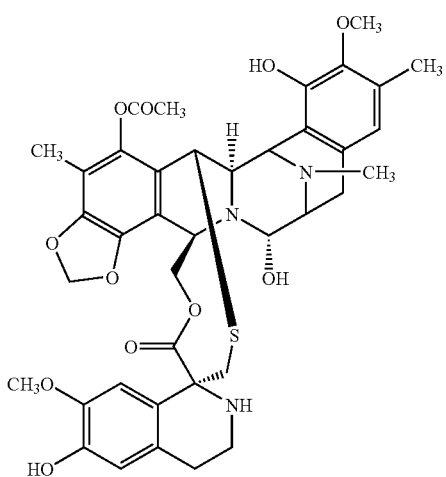

It is currently prepared by isolation from extracts of the marine tunicate *Ecteinascidin turbinata*. The yield is low, and alternative preparative processes have been sought.

A synthetic process for producing ecteinascidin compounds is described in U.S. Pat. No. 5,721,362. The claimed method is long and complicated, there being 38 Examples each describing a step in the synthetic sequence to arrive at ecteinascidin 743.

Claim 25 of U.S. Pat. No. 5,721,362 is directed at an intermediate phenol compound of a given formula (II), which we refer to also as Intermediate 11 or Int-11. It has the following bis(tetrahydroisoquinolinephenol) structure (II):

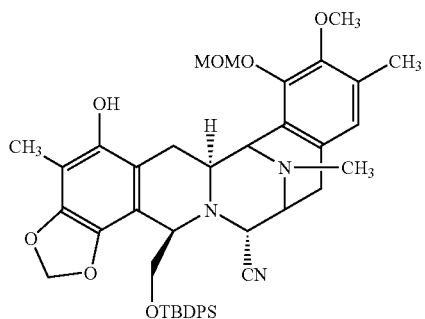

where MOM is a methoxymethyl substituent and TBDPS is a 3,5-t-butyldiphenylsilyl substituent.

From Intermediate 11 it is possible to synthesise another interesting antitumour agent, phthalascidin, see Proc. Natl. Acad. Sci. USA, 96, 3496-3501, 1999. Phthalascidin is a bis(tetrahydroisoquinolinephenol) derivative of formula (III):

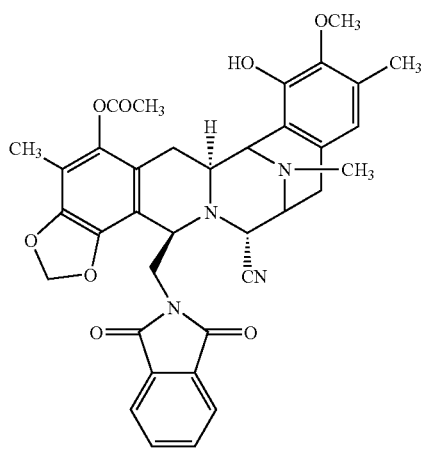

In ecteinascidin 743, the 1,4 bridge has the structure of formula (IV):

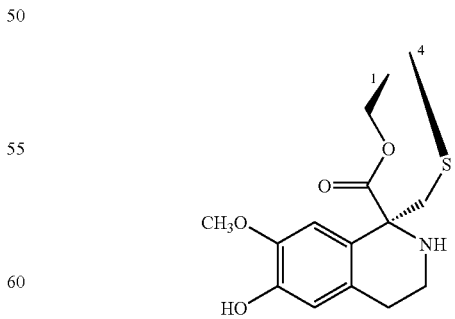

Other known ecteinascidins include compounds with a different bridged cyclic ring system, such as occurs in ecteinascidin 722 and 736, where the bridge has the structure of formula (V):

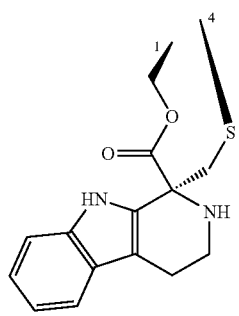

ecteinascidins 583 and 597, where the bridge has the structure of formula (VI):

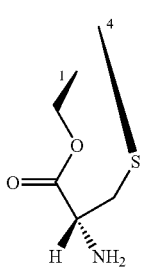

and ecteinascidin 594 and 596, where the bridge has the structure of formula (VII):

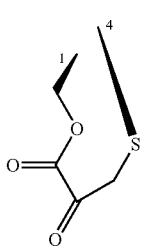

The complete structure for these and related compounds is given in J. Am. Chem. Soc. (1996) 118, 9017-9023. This article is incorporated by reference.

Further compounds are known which lack a bridged cyclic ring system. They include the bis(tetrahydroisoquinoline-quinone) antitumor-antimicrobial antibiotics safracins and saframycins, and the marine natural products renieramicins and xestomycin isolated from cultured microbes or sponges. They all have a common dimeric tetrahydroisoquinoline carbon framework. These compounds can be classified into four types, types I to IV, with respect to the oxidation pattern of the aromatic rings.

Type I, dimeric isoquinolinequinones, is a system of formula (VIII) most commonly occurring in this class of compounds, see the following table I.

TABLE I

Structure of Type I Saframycin Antibiotics.

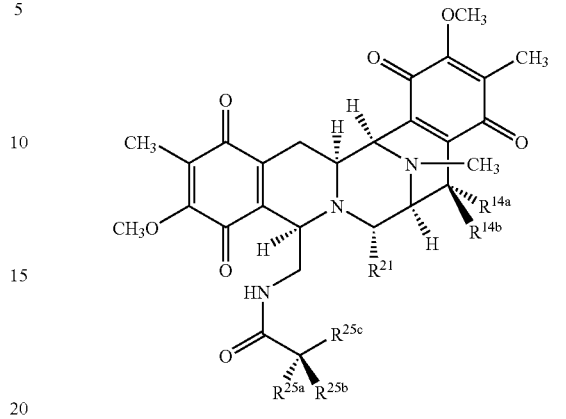

| Compound | $R^{14a}$ | $R^{14b}$ | $R^{21}$ | $R^{25a}$ | $R^{25b}$ | $R^{25c}$ |
|---|---|---|---|---|---|---|
| saframycin A | H | H | CN | O | O | $CH_3$ |
| saframycin B | H | H | H | O | O | $CH_3$ |
| saframycin C | H | $OCH_3$ | H | O | O | $CH_3$ |
| saframycin G | H | OH | CN | O | O | $CH_3$ |
| saframycin H | H | H | CN | OH | $CH_2COCH_3$ | $CH_3$ |
| saframycin S | H | H | OH | O | O | $CH_3$ |
| saframycin $Y_3$ | H | H | CN | $NH_2$ | H | $CH_3$ |
| saframycin $Yd_1$ | H | H | CN | $NH_2$ | H | $C_2H_5$ |
| saframycin $Ad_1$ | H | H | CN | O | O | $C_2H_5$ |
| saframycin $Yd_2$ | H | H | CN | $NH_2$ | H | H |
| saframycin $Y_{2b}$ | H | $Q^b$ | CN | $NH_2$ | H | $CH_3$ |
| saframycin $Y_{2b-d}$ | H | $Q^b$ | CN | $NH_2$ | H | $C_2H_5$ |
| saframycin $AH_2$ | H | H | CN | $H^a$ | $OH^a$ | $CH_3$ |
| saframycin $AH_2Ac$ | H | H | CN | H | OAc | $CH_3$ |
| saframycin $AH_1$ | H | H | CN | $OH^a$ | $H^a$ | $CH_3$ |
| saframycin $AH_1Ac$ | H | H | CN | OAc | H | $CH_3$ |
| saframycin $AR_3$ | H | H | H | H | OH | $CH_3$ |

$^a$assignments are interchangeable.
$^b$where the group Q is of formula (IX):

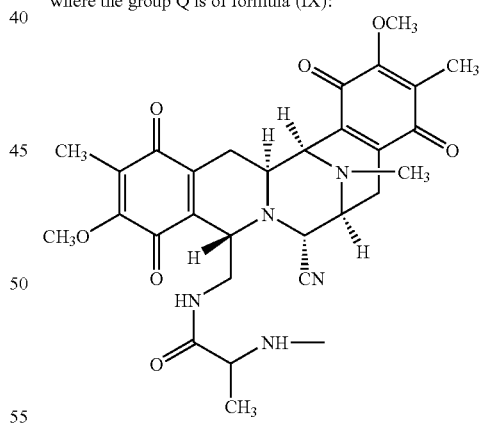

Type I aromatic rings are seen in saframycins A, B and C; G and H; and S isolated from *Streptomyces lavendulae* as minor components. A cyano derivative of saframycin A, called cyanoquinonamine, is known from Japanese Kokai JP-A2 59/225189 and 60/084288. Saframycins $Y_3$, $Yd_1$, $Ad_1$, and $Yd_2$ were produced by *S. lavendulae* by directed biosynthesis, with appropriate supplementation of the culture medium. Saframycins $Y_{2b}$ and $Y_{2b-d}$ dimers formed by linking the nitrogen on the C-25 of one unit to the C-14 of the other, have also been produced in supplemented culture media of *S. lavendulae*. Saframycins $AR_1$ (=$AH_2$,), a microbial reduction product of saframycin A at C-25 produced by *Rhodococcus amidophilus*, is also prepared by nonstereoselective chemical reduction of saframycin A by sodium borohydride as a 1:1 mixture of epimers followed by chromatographic separation [the other isomer $AH_1$ is less polar]. The further reduction product saframycin $AR_3$, 21-decyano-25-dihydro-saframycin A, (=25-dihydrosaframycin B) was produced by the same microbial conversion. Another type of microbial conversion of saframycin A using a *Nocardia* species produced saframycin B and further reduction by a *Mycobacterium* species produced saframycin $AH^1Ac$. The 25-O-acetates of saframycin $AH_2$ and $AH_1$ have also been prepared chemically for biological studies.

Type I compounds of formula (X) have also been isolated from marines sponges, see Table II.

TABLE II

Structures of Type I Compounds from Marine Sponges.

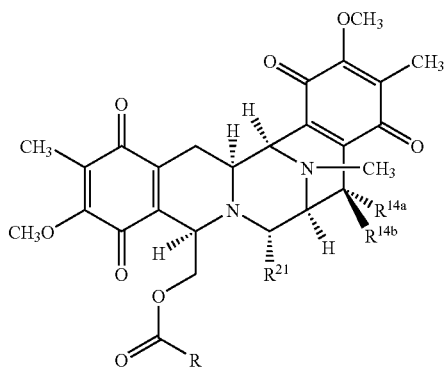

| | | Substituents | |
|---|---|---|---|
| $R^{14a}$ | $R^{14b}$ | $R^{21}$ | R |
| renieramycin A | OH | H | H | —C(CH$_3$)=CH—CH$_3$ |
| renieramycin B | OC$_2$H$_5$ | H | H | —C(CH$_3$)=CH—CH$_3$ |
| renieramycin C | OH | O | O | —C(CH$_3$)=CH—CH$_3$ |
| renieramycin D | OC$_2$H$_5$ | O | O | —C(CH$_3$)=CH—CH$_3$ |
| renieramycin E | H | H | OH | —C(CH$_3$)=CH—CH$_3$ |
| renieramycin F | OCH$_3$ | H | OH | —C(CH$_3$)=CH—CH$_3$ |
| xestomycin | OCH$_3$ | H | H | —CH$_3$ |

Renieramycins A-D were isolated from the antimicrobial extract of a sponge, a *Reniera* species collected in Mexico, along with the biogenetically related monomeric isoquinolines renierone and related compounds. The structure of renieramycin A was initially assigned with inverted stereochemistry at C-3, C-11, and C-13. However, careful examination of the $^1H$ NMR data for new, related compounds renieramycins E and F, isolated from the same sponge collected in Palau, revealed that the ring junction of renieramycins was identical to that of saframycins. This result led to the conclusion that the formerly assigned stereochemistry of renieramycins A to D must be the same as that of saframycins.

Xestomycin was found in a sponge, a *Xestospongia* species collected from Sri Lancan waters.

Type II compounds of formula (XI) with a reduced hydroquinone ring include saframycins D and F, isolated from *S. lavendulae*, and saframycins Mx-1 and Mx-2, isolated from *Myxococcus xanthus*. See table III.

TABLE III

Type II Compounds

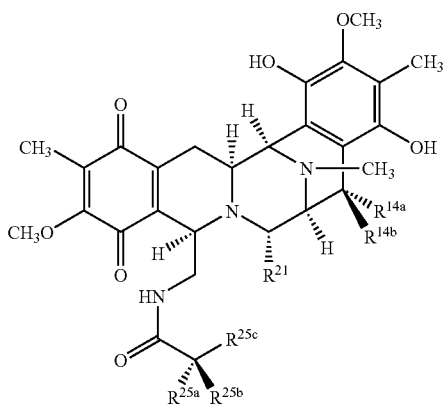

| | Substituents | | | | | |
|---|---|---|---|---|---|---|
| Compound | $R^{14a}$ | $R^{14b}$ | $R^{21}$ | $R^{25a}$ | $R^{25b}$ | $R^{25c}$ |
| saframycin D | O | O | H | O | O | CH$_3$ |
| saframycin F | O | O | CN | O | O | CH$_3$ |
| saframycin Mx-1 | H | OCH$_3$ | OH | H | CH$_3$ | NH$_2$ |
| saframycin Mx-2 | H | OCH$_3$ | H | H | CH$_3$ | NH$_2$ |

The type III skeleton is found in the antibiotics safracins A and B, isolated from cultured *Pseudomonas fluorescens*. These antibiotics of formula (XII) consist of a tetrahydroisoquinoline-quinone subunit and a tetrahydroisoquninoli-nephenol subunit.

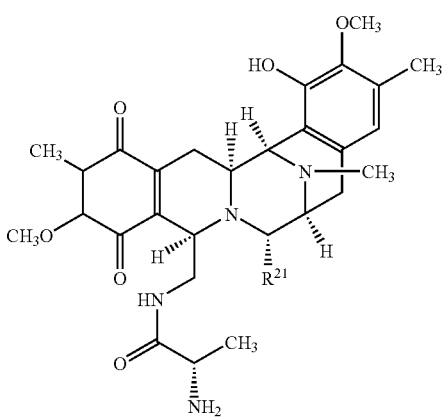

where $R^{21}$ is —H in safracin A and is —OH in safracin B.

Saframycin R, the only compound classified as the Type IV skeleton, was also isolated from *S. lavendulae*. This compound of formula (XIII), consisting of a hydroquinone ring with a glycolic ester sidechain on one of the phenolic oxygens, is conceivably a pro-drug of saframycin A because of its moderate toxicity.

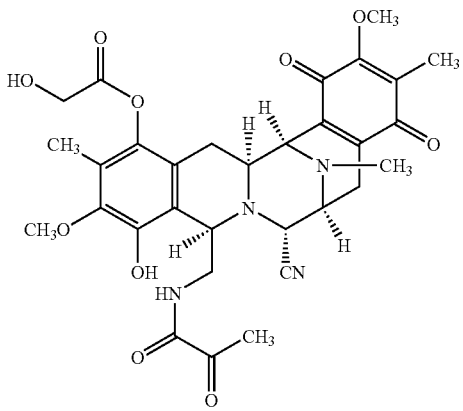

All these known compounds have a fused system of five rings (A) to (E) as shown in the following structure of formula (XIV):

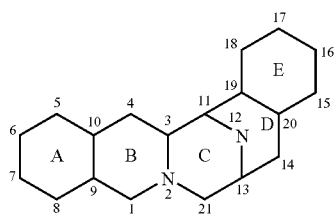

The rings A and E are phenolic in the ecteinascidins and some other compounds, while in other compounds, notably the saframycins, the rings A and E are quinolic. In the known compounds, the rings B and D are tetrahydro, while ring C is perhydro.

OBJECT OF THE INVENTION

The need remains for new active compounds with the fused five-ring system of the known compounds, and for alternative synthetic routes to the ecteinascidin compounds and related compounds. Such synthetic routes may provide more economic paths to the known antitumour agents, as well as permitting preparation of new active compounds.

SUMMARY OF THE INVENTION

In one aspect, the present invention is directed at the use of a known compound, safracin B, also referred to as quinonamine, in hemisynthetic synthesis.

More generally, the invention relates to a hemisynthetic process for the formation of intermediates, derivatives and related structures of ecteinascidin or other tetrahydroisoquinolinephenol compounds starting from natural bis(tetrahydroisoquinoline) alkaloids. Suitable starting materials for the hemi-synthetic process include the classes of saframycin and safracin antibiotics available from different culture broths, and also the classes of reineramicin and xestomycin compounds available from marine sponges.

A general formula (XV) for the starting compounds is as follows:

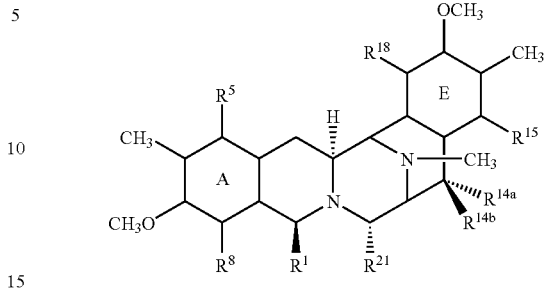

where:

$R^1$ is an amidomethylene group such as —$CH_2$—NH—CO—$CR^{25a}R^{25b}R^{25c}$ where $R^{25a}$ and $R^{25b}$ form a keto group or one is —OH, —$NH_2$ or —$OCOCH_3$ and the other is —$CH_2COCH_3$, —H, —OH or —$OCOCH_3$, provided that when $R^{25a}$ is —OH or —$NH_2$ then $R^{25b}$ is not —OH, and $R^{25c}$ is —H, —$CH_3$ or —$CH_2CH_3$, or $R^1$ is an acyloxymethylene group such as —$CH_2$—O—CO—R, where R is —$C(CH_3)$=CH—$CH_3$ or —$CH_3$;

$R^5$ and $R^8$ are independently chosen from —H, —OH or —$OCOCH_2OH$, or $R^5$ and $R^8$ are both keto and the ring A is a p-benzoquinone ring;

$R^{14a}$ and $R^{14b}$ are both —H or one is —H and the other is —OH, —$OCH_3$ or —$OCH_2CH_3$, or $R^{14a}$ and $R^{14b}$ together form a keto group;

$R^{15}$ and $R^{18}$ are independently chosen from —H or —OH, or $R^5$ and $R^8$ are both keto and the ring A is a p-benzoquinone ring; and $R^{21}$ is —OH or —CN.

A more general formula for these class of compounds is provided below:

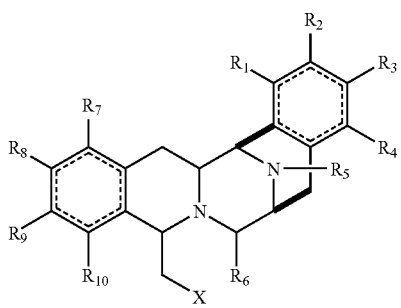

wherein the substituent groups defined by $R_1$, $R_2$, $R_3$, $R_4$, $R_5$, $R_6$, $R_7$, $R_8$, $R_9$, $R_{10}$ are each independently selected from the group consisting of H, OH, $OCH_3$, CN, =O, $CH_3$;

wherein X are the different amide or ester functionalities contained in the mentioned natural products;

wherein each dotted circle represents one, two or three optional double bonds.

Thus, according to the present invention, we now provide hemisynthetic routes for the production of intermediates including Intermediate 11 and thus for the production of the ecteinascidin compounds as well as phthalascidin and additional compounds. The hemisynthetic routes of the invention each comprise a number of transformation steps to arrive at the desired product. Each step in itself is a process in accordance with this invention. The invention is not limited to the routes that are exemplified, and alternative routes may be provided by, for example, changing the order of the transformation steps, as appropriate.

In particular, this invention involves the provision of a 21-cyano starting material of general formula (XVI):

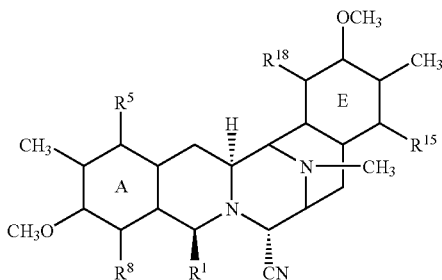

where $R^1$, $R^5$, $R^8$, $R^{14a}$, $R^{14b}$, $R^{15}$ and $R^{18}$ are as defined.

Other compounds of formula (XVI) with different substituents at the 21-position may also represent possible starting materials. In general, any derivative capable of production by nucleophilic displacement of the 21-hydroxy group of compounds of formula (XV) wherein $R^{21}$ is a hydroxy group c is a candidate. Examples of suitable 21-substituents include but are not limited to:

- a mercapto group;
- an alkylthio group (the alkyl group having from 1 to 6 carbon atoms);
- an arylthio group (the aryl group having from 6 to 10 carbon atoms and being unsubstituted or substituted by from 1 to 5 substituents selected from, for example, alkyl group having from 1 to 6 carbon atoms, alkoxy groups having from 1 to 6 carbon atoms, halogen atoms, mercapto groups and nitro groups);
- an amino group;
- a mono- or dialkylamino (the or each alkyl group having from 1 to 6 carbon atoms);
- a mono- or diarylamino group (the or each aryl group being as defined above in relation to arylthio groups);
- an α-carbonylalkyl group of formula —$C(R^a)(R^b)$—C(=O)$R^c$, where $R^a$ and $R^b$ are selected from hydrogen atoms, alkyl groups having from 1 to 20 carbon atoms, aryl groups (as defined above in relation to arylthio groups) and aralkyl groups (in which an alkyl group having from 1 to 4 carbon atoms is substituted by an aryl group a defined above in relation to arylthio groups), with the proviso that one of $R^a$ and $R^b$ is a hydrogen atom;

$R^c$ is selected from a hydrogen atom, an alkyl group having from 1 to 20 carbon atoms, aryl groups (as defined above in relation to arylthio groups), an aralkyl group (in which an alkyl group having from 1 to 4 carbon atoms is substituted by an aryl group a defined above in relation to arylthio groups), an alkoxy group having from 1 to 6 carbon atoms, an amino group or a mono- or dialkylamino group as defined above.

Thus, in a more general aspect, the present invention relates to processes where the first step is to form a 21-derivative using a nucleophilic reagent. We refer to such compounds as 21-Nuc compounds.

The presence of the 21-cyano group is required for some of the end-products, notably ecteinascidin 770 and phthalascidin, while for other end-products it acts as a protecting group which can readily be converted to another substituent, such as the 21-hydroxy group of ecteinascidin 743 or of 21-hydroxyphthalascidin. The adoption of the 21-cyano compound as the starting material effectively stabilises the molecule during the ensuing synthetic steps, until it is optionally removed. Other 21-Nuc compounds can offer this and other advantages.

In one important aspect, the present invention consists in the use of a 21-cyano compound of the general formula (XVI) in the preparation of a bis- or tris-(tetrahydroisoquinolinephenol) compounds. Products which may be prepared include intermediates such as Intermediate 11, and the ecteinascidins and phthalascidin, as well as new and known compounds of related structure.

Preferred starting materials include those compounds of formula (XV) or (XVI) where $R^{14a}$ and $R^{14b}$ are both hydrogen. Preferred starting materials also include compounds of formula (XV) or (XVI) where $R^{15}$ is hydrogen. Furthermore, the preferred starting materials include compounds of formula (XV) or (XVI) where ring E is a phenolic ring. Preferred starting materials further include compounds of formula (XV) or (XVI) where at least one, better at least two or three of $R^5$, $R^8$, $R^{15}$ and $R^{18}$ is not hydrogen.

Examples of suitable starting materials for this invention include saframycin A, saframycin B, saframycin C, saframycin G, saframycin H, saframycin S, saframycin $Y_3$, saframycin $Yd_1$, saframycin $Ad_1$, saframycin $Yd_2$, saframycin $AH_2$, saframycin $AH_2Ac$, saframycin $AH_1$, saframycin $AH_1Ac$, saframycin $AR_3$, renieramycin A, renieramycin B, renieramycin C, renieramycin D, renieramycin E, renieramycin F, xestomycin, saframycin D, saframycin F, saframycin Mx-1, saframycin Mx-2, safracin A, safracin B and saframycin R. Preferred starting materials have a cyano group in position 21, for the group $R^{21}$.

In a particularly preferred aspect, the invention involves a hemisynthetic process wherein the transformation steps are applied to safracin B:

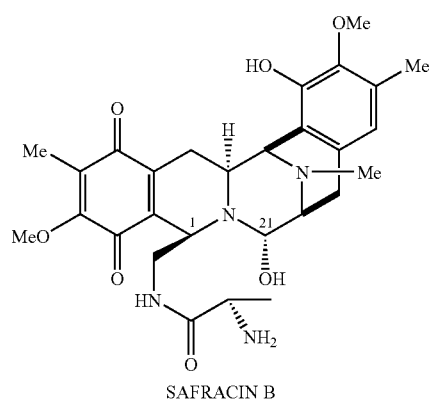

SAFRACIN B

Safracin B presents a ring system closely related to the ecteinascidins. This compound has the same pentacycle structure and the same substitution pattern in the right-hand aromatic ring, ring E. Also, safracin B presents very close similarities to some of the synthetic intermediates in the total synthesis of ET-743, particularly to the intermediate 11. Such intermediate can be transformed into Et-743 using a well established method. Synthetic conversion of safracin B into intermediate 11 will therefore provide an hemi-synthetic method to obtain ET-743.

Thus, we provide Intermediate 11 made from this compound safracin B, and compounds derived from Intermediate 11, particularly ecteinascidin compounds. We further provide phthalascidin made from safracin B. The invention also relates to use of safracin B in the production of Intermediate 11, phthalascidin, ecteinascidin compounds and the other intermediates of the invention. The invention also relates to compounds described herein derived from the other suggested starting materials, and use of those compounds in the production of such compounds.

The more preferred starting materials of this invention have a 21-cyano group. The currently most preferred compound of the present invention is the compound of Formula 2. This compound is obtained directly from safracin B and is considered a key intermediate in the hemisynthetic process.

compound 2

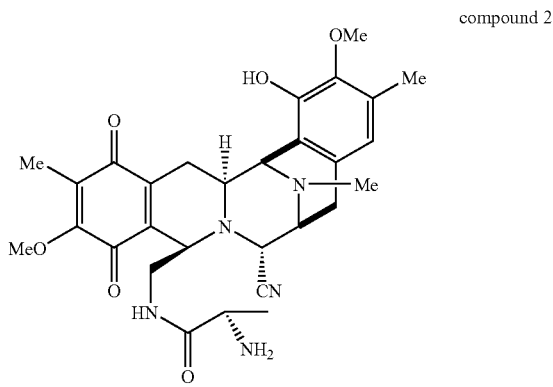

In a related aspect, we provide cyanosafracin B by fermentation of a safracin B-producing strain of *Pseudomonas fluorescens*, and working up the cultured broth using cyanide ion. The preferred strain of *Pseudomonas fluorescens* is strain A2-2, FERM BP-14, which is employed in the procedure of EP 055,299. A suitable source of cyanide ion is potassium cyanide. In a typical work-up, the broth is filtered and excess cyanide ion is added. After an appropriate interval of agitation, such as 1 hour, the pH is rendered alkaline, say pH 9.5, and an organic extraction gives a crude extract which can be further purified to give the cyanosafracin B.

For the avoidance of doubt, the stereochemistries indicated in this patent specification are based on our understanding of the correct stereochemistry of the natural products. To the extent that an error is discovered in the assigned stereochemistry, then the appropriate correction needs to be made in the formulae given throughout in this patent specification. Furthermore, to the extent that the syntheses are capable of modification, this invention extends to stereoisomers.

The products of this invention are typically of the formula (XVIIa):

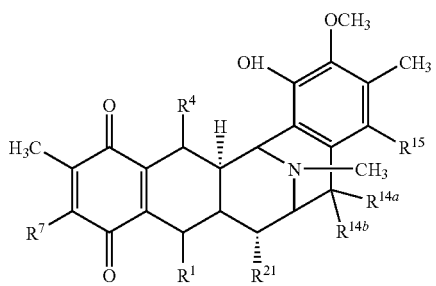

or formula (XVIIb)

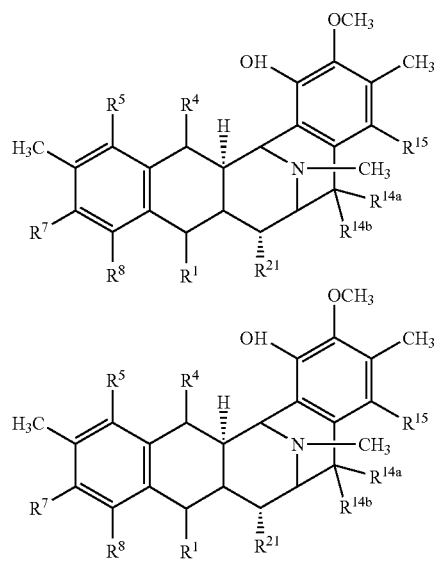

where $R^1$ is an optionally protected or derivatised aminomethylene group, an optionally protected or derivatised hydroxymethylene group, such as a group $R^1$ as defined for the formula (XV);

$R^4$ is —H; or $R^1$ and $R^4$ together form a group of formula (IV), (V) (VI) or (VII):

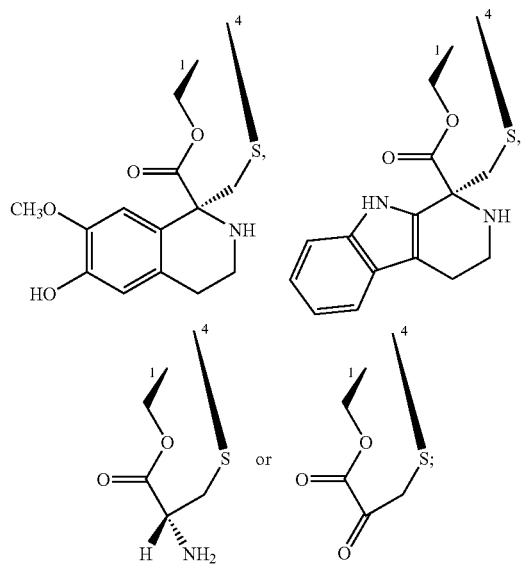

$R^5$ is —H or —OH;

$R^7$ is —OCH$_3$ and $R^8$ is —OH or $R^7$ and $R^8$ together form a group —O—CH$_2$—O—;

$R^{14a}$ and $R^{14b}$ are both —H or one is —H and the other is —OH, —OCH$_3$ or —OCH$_2$CH$_3$, or $R^{14a}$ and $R^{14b}$ together form a keto group; and $R^{15}$ is —H or —OH;

$R^{21}$ is —H, —OH or —CN;

and derivatives including acyl derivatives thereof especially where $R^5$ is acetyloxy or other acyloxy group of up to 4 carbon atoms, and including derivatives where the group —NCH$_3$— at the 12-position is replaced by —NH— or —NCH$_2$CH$_3$—, and derivatives where the —NH$_2$ group in the compound of formula (VI) is optionally derivatised.

In the formulae (XVIIa) or (XVIIb), $R^1$ is typically aminomethylene, amidomethylene or $R^1$ with $R^4$ forms a group (IV) or (V). Suitable amidomethylene groups include those of formula —CH$_2$—NH—CO—CHCH$_3$—NH$_2$ derived from alanine, and similar groups derived from other amino acids, notably, both D and L, glycine, valine, leucine, isoleucine, phenylalanine, tyrosine, tryptophan, methionine, cysteine, aspartate, asparagine, glutamatic acid, glutamine, lysine, arginine, proline, serine, threonine, histidine and hydroxyproline. A general formula for the group $R^1$ is then —CH$_2$—NH-aa, where aa indicates an acylamino acid group.

The group $R^1$ can be acylated on an —NH$_2$ group, and for example N-acyl derivatives can be formed from groups —CH$_2$NH$_2$ and —CH$_2$—NH-aa. The acyl derivatives can be N-acyl or N-thioacyl derivatives thereof, as well as cyclic amides. The acyl groups can illustratively be alkanoyl, haloalkanoyl, arylalkanoyl, alkenoyl, heterocyclylacyl, aroyl, arylaroyl, haloaroyl, nitroaroyl, or other acyl groups. The acyl groups can be of formula —CO—$R^a$, where $R^a$ can be various groups such as alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy, heterocyclyl, heterocyclyloxy, alkyl, amino or substituted amino. Other acylating agents include isothiocyanates, such as aryl isothiocyanates, notably phenyl isocyanate. The alkyl, alkoxy or alkylene groups of $R^a$ suitably have 1 to 6 or 12 carbon atoms, and can be linear, branched or cyclic. Aryl groups are typically phenyl, biphenyl or naphthyl. Heterocyclyl groups can be aromatic or partially or completely unsaturated and suitably have 4 to 8 ring atoms, more preferably 5 or 6 ring atoms, with one or more heteroatoms selected from nitrogen, sulphur and oxygen.

Without being exhaustive, typical $R^a$ groups include alkyl, haloalkyl, alkoxyalkyl, haloalkoxyalkyl, arylalkylene, haloalkylarylakylene, acyl, haloacyl, arlyalkyl, alkenyl and amino acid. For example, $R^a$—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, or trans-hexenoylcarbonyl, or alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides. Other examples may be found among the listed protecting groups.

Compounds wherein —CO—$R^a$ is derived from an amino acid and include an amino group can themselves form acyl derivatives. Suitable N-acyl commands include dipeptides which in turn can form N-acyl derivatives.

In one variation which relates to intermediate products, the ring A is modified to incorporate the substructure shown as formula (XX) or (XXI), discussed later.

In another variation relating to intermediates, the group $R^1$ can be —CH$_2$O—CO—CFu-CH$_2$—S-Prot$^3$, derived from a compound of formula (XIX), where Prot$^3$ and Fu have the indicated meanings. In such a case, $R^7$ and $R^8$ from the oxymethyleneoxy group. The group $R^{18}$ is usually protected. Usually $R^{21}$ is cyano.

Preferably $R^{14a}$ and $R^{14b}$ are hydrogen. Preferably $R^{15}$ is hydrogen. The O-acyl derivatives are suitably aliphatic O-acyl derivatives, especially acyl derivatives of 1 to 4 carbon atoms, and typically an O-acetyl group, notably at the 5-position.

Suitable protecting groups for phenols and hydroxy groups include ethers and esters, such as alkyl, alkoxyalkyl, aryloxyalkyl, alkoxyalkoxyalkyl, alkylsilylalkoxyalkyl, alkylthioalkyl, arylthioalkyl, azidoalkyl, cyanoalkyl, chloroalkyl, heterocyclic, arylacyl, haloarylacyl, cycloalkylalkyl, alkenyl, cycloalkyl, alyklarylalkyl, alkoxyarylalkyl, nitroarylalkyl, haloarylalkyl, alkylaminocarbonylarylalkyl, alkylsulfinylarylalky, alkylsilyl and other ethers, and arylacyl, aryl alkyl carbonate, aliphatic carbonate, alkylsulfinylarlyalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted with the previously mentioned groups in $R^1$.

Suitable protecting groups for amines include carbamates, amides, and other protecting groups, such as alkyl, arylalkyl, sulpho- or halo-arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, heterocyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted with the previously mentioned groups in $R^1$.

Examples of such protecting groups are given in the following tables.

| protection for —OH group | |
|---|---|
| ethers | abbreviation |
| methyl | |
| methoxymethyl | MOM |
| benzyloxymethyl | BOM |
| methoxyethoxymethyl | MEM |
| 2-(trimethylsilyl)ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |

| -continued | |
|---|---|
| 4-(dimethylamino)carbonylbenzyl | |
| 4-methylsuflinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |

| esters | |
|---|---|
| aryl formate | |
| aryl acetate | |
| aryl levulinate | |
| aryl pivaloate | ArOPv |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-OAr |
| aryl methanesulfonate | |
| aryl toluenesulfonate | |
| aryl 2-formylbenzenesulfonate | |

| protection for the —NH$_2$ group | |
|---|---|
| carbamates | abbreviation |
| methyl | |
| ethyl | |
| 9-fluorenylmethyl | Fmoc |
| 9-(2-sulfo)fluroenylmethyl | |
| 9-(2,7-dibromo)fluorenylmethyl | |
| 17-tetrabenzo[a,c,g,i]fluorenylmethyl | Tbfmoc |
| 2-chloro-3-indenylmethyl | Climoc |
| benz[f]inden-3-ylmethyl | Bimoc |
| 2,7-di-t-butyl[9-(10,10-dioxo-10,10,10-tetrahydrothioxanthyl)]methyl | DBD-Tmoc |
| 2,2,2-trichloroethyl | Troc |
| 2-trimethylsilylethyl | Teoc |
| 2-phenylethyl | hZ |
| 1-(1-adamantyl)-1-methylethyl | Adpoc |
| 2-chlooethyl | |
| 1,1-dimethyl-2-chloroethyl | |
| 1,1-dimethyl-2-bromoethyl | |
| 1,1-dimethyl-2,2-dibromoethyl | DB-t-BOC |
| 1,1-dimethyl-2,2,2-trichloroethyl | TCBOC |
| 1-methyl-1-(4-biphenyl)ethyl | Bpoc |
| 1-(3,5-di-t-butylphenyl)-1-1-methylethyl | t-Burmeoc |
| 2-(2'-and 4'-pyridyl)ethyl | Pyoc |
| 2,2-bis(4'-nitrophenyl)ethyl | Bnpeoc |
| n-(2-pivaloylamino)-1,1-dimethylethyl | |
| 2-[(2-nitrophenyl)dithio]-1-phenylethyl | NpSSPeoc |
| 2-(n,n-dicyclohexylcarboxamido)ethyl | |
| t-butyl | BOC |
| 1-adamantyl | 1-Adoc |
| 2-adamantyl | 2-Adoc |
| vinyl | Voc |
| allyl | Aloc or Alloc |
| 1-isopropylallyl | Ipaoc |
| cinnamyl | Coc |
| 4-nitrocinnamyl | Noc |
| 3-(3'-pyridyl)prop-2-enyl | Paloc |
| 8-quinolyl | |
| n-hydroxypiperidinyl | |
| alkyldithio | |
| benzyl | Cbz or Z |
| p-methoxybenzyl | Moz |
| p-nitrobenzyl | PNZ |
| p-bromobenzyl | |
| p-chlorobenzyl | |
| 2,4-dichlorobenzyl | |
| 4-methylsulfinylbenzyl | Msz |
| 9-anthrylmethyl | |
| diphenylmethyl | |
| phenothiazinyl-(10)-carbonyl | |
| n'-p-toluenesulfonylaminocarbonyl | |
| n'-phenylaminothiocarbonyl | |

| amides | |
|---|---|
| formamide | |
| acetamide | |
| chloroacetamide | |
| trifluoroacetamide | TFA |
| phenylacetamide | |
| 3-phenylpropanamide | |
| pent-4-enamide | |
| picolinamide | |
| 3-pyridylcarboxamide | |
| benzamide | |
| p-phenylbenzamide | |
| n-phthalimide | |
| n-tetrachlorophthalimide | TCP |
| 4-nitro-n-phthalimide | |
| n-dithiasuccinimide | Dts |
| n-2,3-diphenylmaleimide | |
| n-2,5-dimethylpyrrole | |
| n-2,5-bis(triisopropylsiloxyl)pyrrole | BIPSOP |
| n-1,1,4,4-tetramethyldisiliazacyclopentante adduct | STABASE |
| 1,1,3,3-tetramethyl-1,3-disilaisoindoline | BSB |

| special —NH protective groups | |
|---|---|
| n-methylamine | |
| n-t-butylamine | |
| n-allylamine | |
| n-[2-trimethylsilyl)ethoxy]methylamine | SEM |
| n-3-acetoxypropylamine | |
| n-cyanomethylamine | |
| n-(1-isopropyl-4-nitro-2-oxo-3-pyrrolin-3-yl)amine | |
| n-2,4-dimethoxybenzylamine | Dmb |
| 2-azanorbornenes | |
| n-2,4-dinitrophenylamine | |
| n-benzylamine | Bn |
| n-4-methoxybenzylamine | MPM |
| n-2,4-dimethoxybenzylamine | DMPM |
| n-2-hydroxybenzylamine | Hbn |
| n-(diphenylmethyl)amino | DPM |
| n-bis(4-methoxyphenyl)methylamine | |
| n-5-dibenzosuberylamine | DBS |
| n-triphenylmethylamine | Tr |
| n-[(4-methoxyphenyl)diphenylmethyl]amino | MMTr |
| n-9-phenylflurenylamine | Pf |
| n-ferrocenylmethylamine | Fcm |
| n-2-picolylamine n'-oxide | |
| n-1,1-dimethylthiomethyleneamine | |
| n-benzylideneamine | |
| n-p-methoxybenzylideneamine | |
| n-diphenylmethyleneamine | |
| n-(5,5-dimethyl-3-oxo-1-cyclohexenyl)amine | |
| n-nitroamine | |
| n-nitrosoamine | |
| diphenylphosphinamide | Dpp |
| dimethylthiophosphinamide | Mpt |
| diphenylthiophosphinamide | Ppt |
| dibenzyl phosphoramidate | |
| 2-nitrobenzenesulfenamide | Nps |
| n-1-(2,2,2-trifluoro-1,1-diphenyl)ethylsufenamide | TDE |
| 3-nitro-2-pyridinesulfenamide | Npys |
| p-toluenesulfonamide | Ts |
| benzenesulfonamide | |

Safracin B includes an alanyl sidechain. In one aspect of the invention, we have found that protection of the free amino group with a Boc group can give strong advantages.

Particular ecteinascidin products of this invention include compounds of the formula (XVIII):

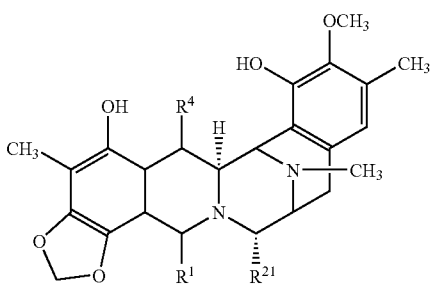

where $R^1$ and $R^4$ form a group of formula (IV), (V), (VI) or (VII):

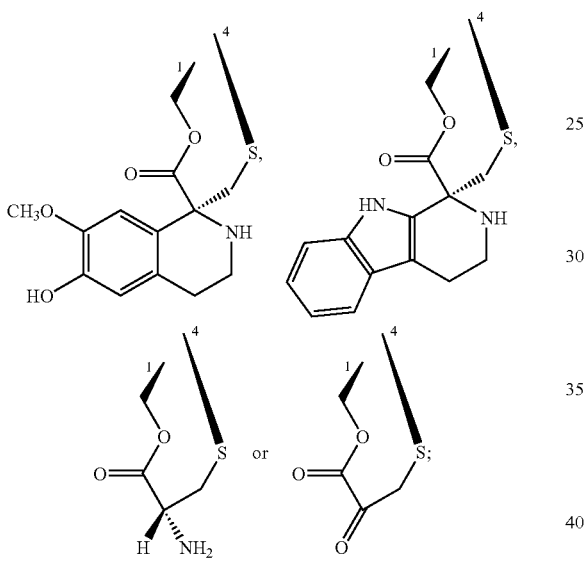

more particularly a group (IV) or (V);
$R^{21}$ is —H, —OH or —CN, more particularly —OH or —CN; and acyl derivatives thereof, more particularly 5-acyl derivatives including the 5-acetyl derivative.

Formation of Ecteinascidin 743 and Related Compounds.

In general, the conversion of the 21-cyano starting compound to an ecteinascidin product of, for example, formula (XVIII) involves:
a) conversion if necessary of a quinone system for the ring E into the phenol system
b) conversion if necessary of a quinone system for the ring A into the phenol system;
c) conversion of the phenol system for the ring A into the methylenedioxyphenol ring;
d) formation of the bridged spiro ring system of formula (IV), (VI) or (VII) across the 1-position and 4-position in ring B; and
e) derivatisation as appropriate, such as acylation.

Step (a), conversion if necessary of a quinone system for the ring E into the phenol system, can be effected by conventional reduction procedures. A suitable reagent system is hydrogen with a palladium-carbon catalyst, though other reducing systems can be employed.

Step (b), conversion if necessary of a quinone system for the ring A into the phenol system is analogous to step (a), and more detail is not needed.

Step (c), conversion of the phenol system for the ring A into the methylenedioxyphenol ring, can be effected in several ways, possibly along with step (b). For example, a quinone ring A can be demethylated in the methoxy substituent at the 7-position and reduced to a dihydroquinone and trapped with a suitable electrophilic reagent such as $CH_2Br_2$, $BrCH_2Cl$, or a similar divalent reagent directly yielding the methylenedioxy ring system, or with a divalent reagent such as thiocarbonyldiimidazol which yields a substituted methylenedioxy ring system which can be converted to the desired ring.

Step (d) is typically effected by appropriate substitution at the 1-position with a bridging reagent that can assist formation of the desired bridge, forming an exendo quinone methide at the 4-position and allowing the methide to react with the 1-substituent to bring about the bridged structure. Preferred bridging reagents are of formula (XIX)

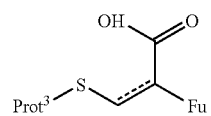

where Fu indicates a protected functional group, such as a group —NHProt$^{4a}$ or OProt$^{4b}$, Prot$^3$ is a protecting group, and the dotted line shows an optional double bond.

Suitably the methide is formed by first introducing a hydroxy group at the 10-position at the junction of rings A and B to give a partial structure of formula (XX):

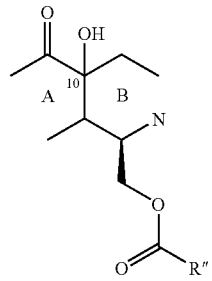

or more preferably a partial structure of formula (XXI):

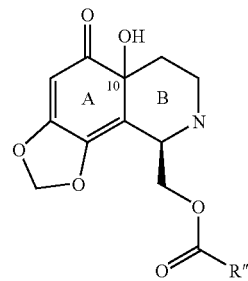

where the group R" is chosen for the desired group of formula (IV), (V), (VI) or (VII). For the first two such groups, the group R" typically takes the form —CHFu-CH$_2$—SProt$^3$. The protecting groups can then be removed and modified as appropriate to give the desired compound.

A typical procedure for step (d) is provided in U.S. Pat. No. 5,721,362 incorporated by reference. Particular reference is made to the passage at column 8, step (1) and Example 33 of the US patent, and related passages.

Derivatisation in step (e) can include acylation, for instance with a group R$^a$—CO— as well as conversion of the 12-NCH$_3$ group to 12-NH or 12-NCH$_2$CH$_3$. Such conversion can be effected before or after the other steps, using available methods.

By way of illustration, it is now feasible to transform cyanosafracin B compound of formula 2 into ET-743 resulting in a shorter and more straightforward way to make ET-743 than methods previously described. Cyanosafracin B can be transformed into Intermediate 25;

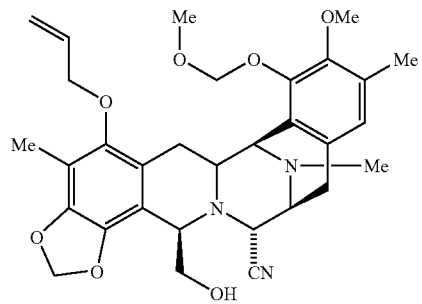

INT-25 and from this derivative it is possible to introduce a number of cysteine derivatives that can be transformed later into Et-743. Preferred cysteine derivatives are exemplified by the following two compounds:

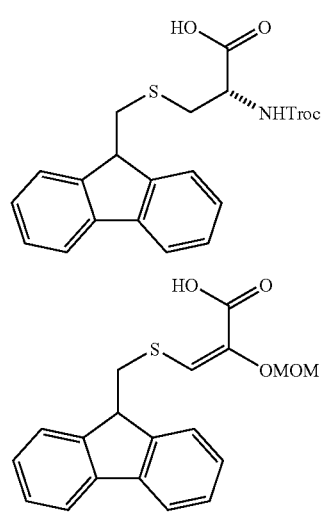

Int-29

Int-37

The retrosynthetic analysis to make ET-743 using compound 29 is depicted in scheme I.

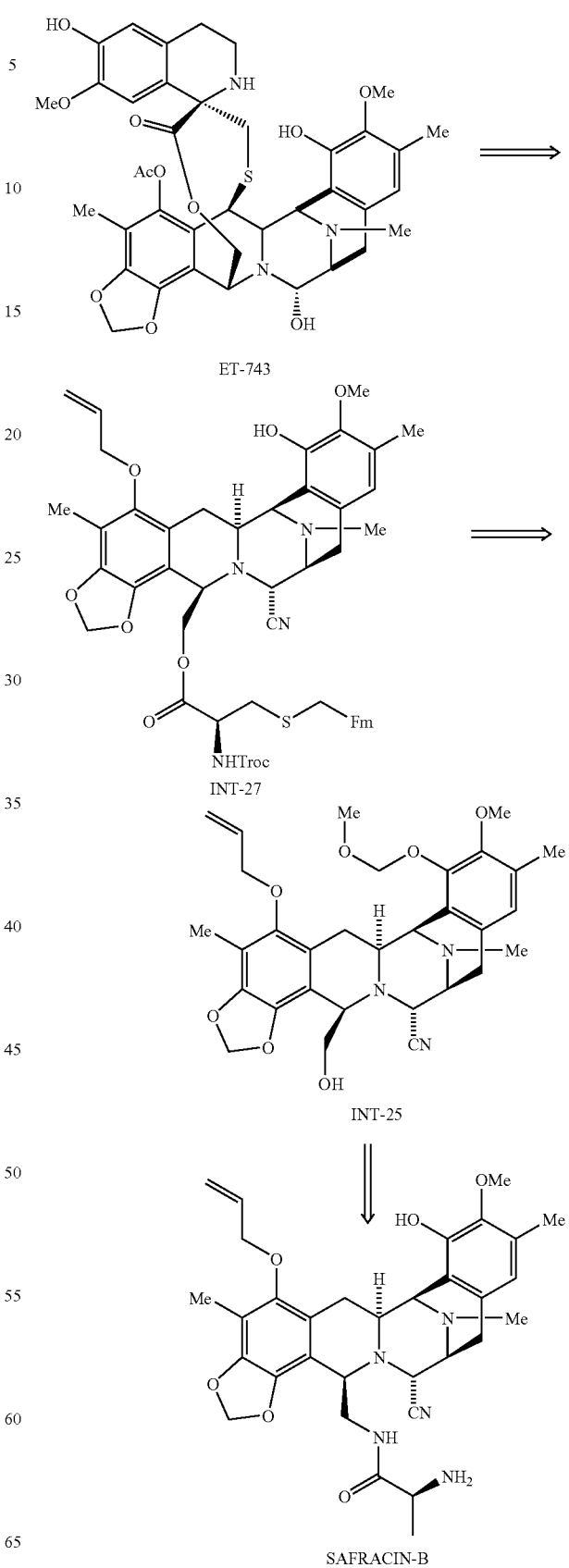

Scheme I

ET-743

INT-27

INT-25

SAFRACIN-B

Following the above scheme I it is possible to obtain ET-743 in 21 linear steps. This method transforms cyanosafracin B into intermediate 25 through a sequence of reactions that involves essentially (1) removal of methoxy group placed in ring A, (2) reduction of ring A and formation of methylene-dioxy group in one pot, (3) hydrolysis of amide function placed over carbon 1, (4) transformation of the resulting amine group into hydroxyl group. Furthermore the method avoids protection and de-protection of the primary alcohol function at the position 1 in ring B of compound 25 using directly a cysteine residue 29 to form intermediate 27. Cysteine derivative 29 is protected in the amino group with β-β-β-trichloroethoxycarbonyl protecting group in order to have compatibility with the existing allyl and MOM groups. Intermediate 27 is directly oxidized and cycled. These circumstances, together with a different de-protecting strategy in the later stages of the synthesis makes the route novel and more amenable to industrial development than the process of U.S. Pat. No. 5,721,362.

The conversion of the 2-cyano compound into Intermediate 25 usually involves the following steps (see scheme II):

formation of the protected compound of Formula 14 by reacting 2 with tert-butoxycarbonyl anhydride;

converting of 14 into the di-protected compound of Formula 15 by reacting with bromomethylmethyl ether and diisopropylethylamine in acetonitrile;

selectively elimination of the methoxy group of the quinone system in 15 to obtain the compound of Formula 16 by reacting with a methanolic solution of sodium hydroxide;

transforming of 16 into the methylene-dioxy compound of Formula 18 by employing the next preferred sequence: (1) quinone group of compound 16 is reduced with 10% Pd/C under hydrogen atmosphere; (2) the hydroquinone intermediate is converted into the methylenedioxy compound of Formula 17 by reacting with bromochloromethane and caesium carbonate under hydrogen atmosphere; (3) 17 is transformed into the compound of Formula 18 by protecting the free hydroxyl group as a OCH$_2$R group. This reaction is carried out with BrCH$_2$R and caesium carbonate, where R can be aryl, CH=CH$_2$, OR' etc.

elimination of the tert-butoxycarbonyl and the methyloxymethyl protecting groups of 18 to afford the compound of Formula 19 by reacting with a solution of HCl in dioxane. Also this reaction is achieved by mixing 18 with a solution of trifluoroacetic acid in dichloromethane;

formation of the thiourea compound of Formula 20 by reacting 19 with phenylisothiocyanate;

converting compound of Formula 20 into the amine compound of Formula 21 by reacting with a solution of hydrogen chloride in dioxane;

transforming compound of Formula 21 into the N-Troc derivative 22 by reacting with trichloroethyl chloroformate and pyridine;

formation of the protected hydroxy compound of Formula 23 by reacting 22 with bromomethylmethyl ether and diisopropylethylamine;

transforming compound of Formula 23 into the N—H derivative 24 by reacting with acetic acid and zinc;

conversion of compound of Formula 24 into the hydroxy compound of Formula 25 by reaction with sodium nitrite in acetic acid. Alternatively, it can be used nitrogen tetroxide in a mixture of acetic acid and acetonitrile followed by treatment with sodium hydroxide. Also, it can be used sodium nitrite in a mixture of acetic anhydride-acetic acid, followed by treatment with sodium hydroxide.

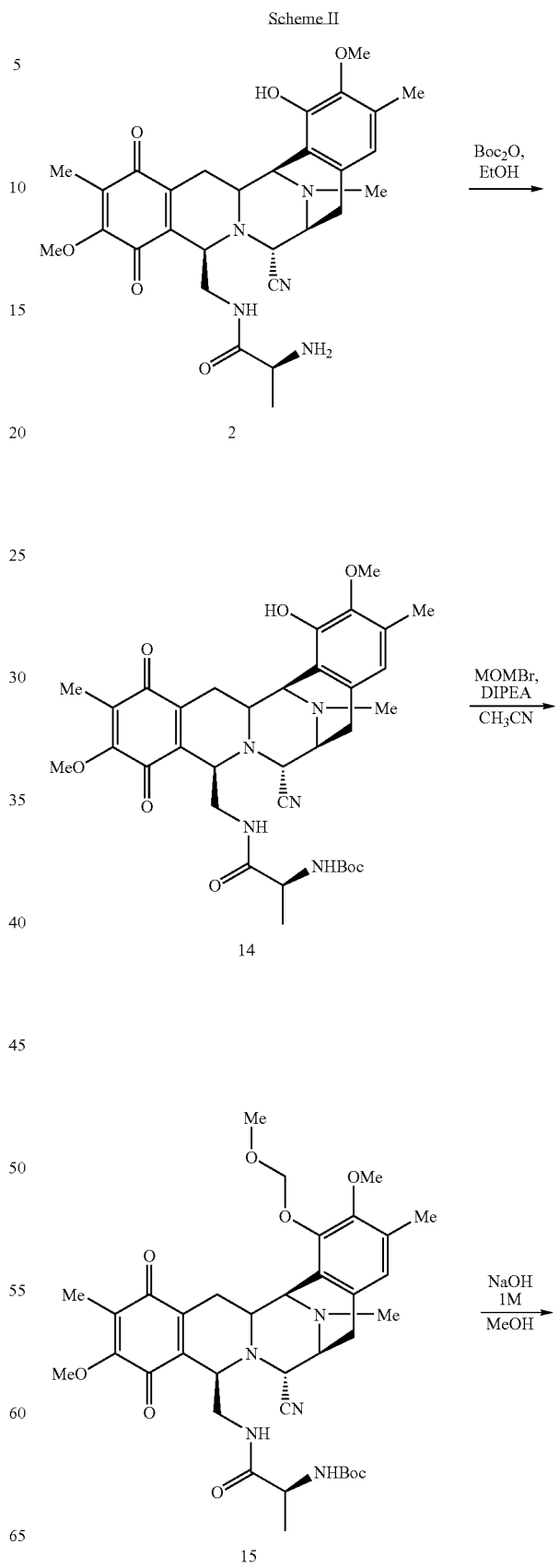

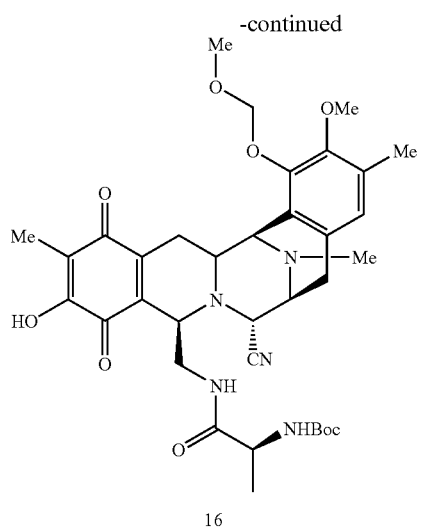
16
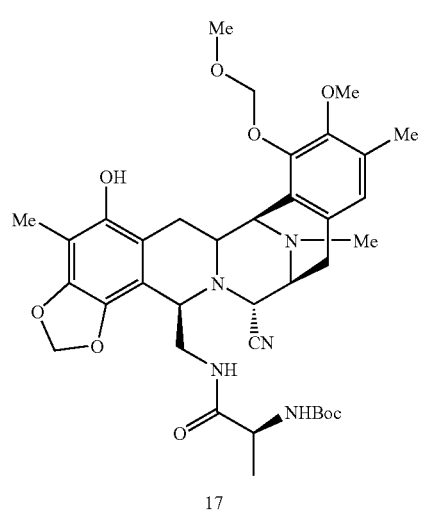
17
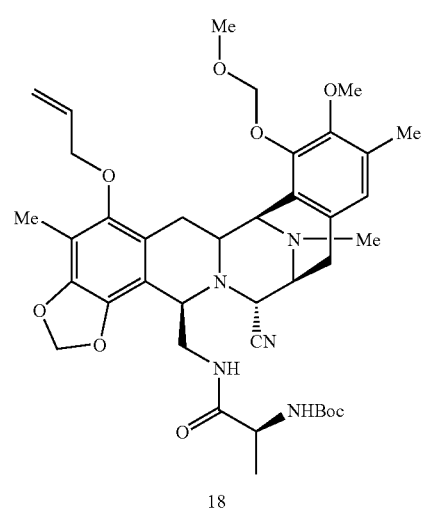
18
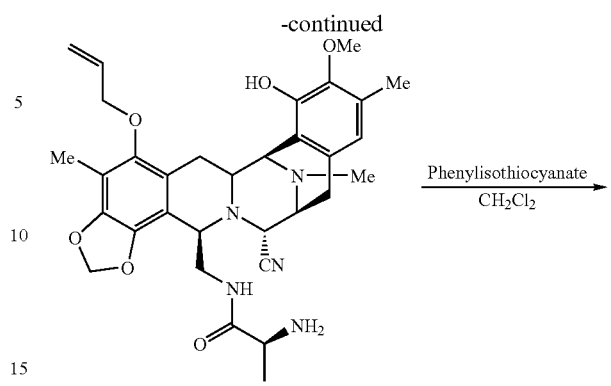
19
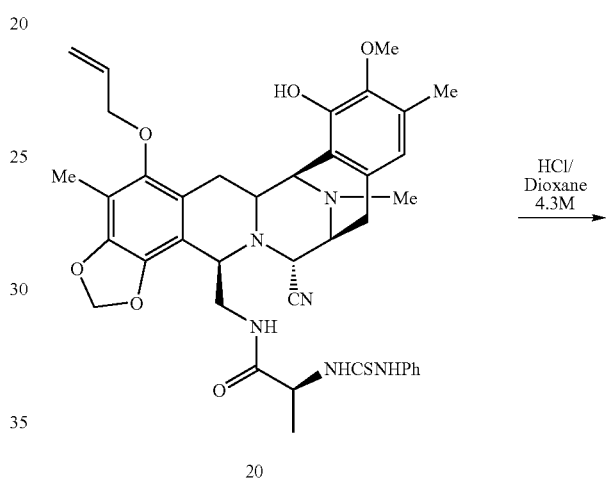
20
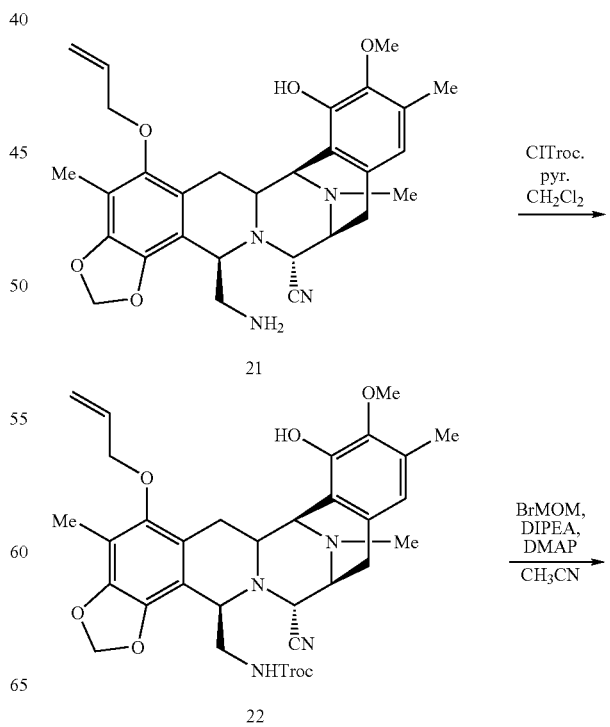
21
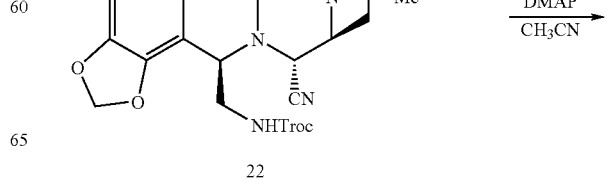
22

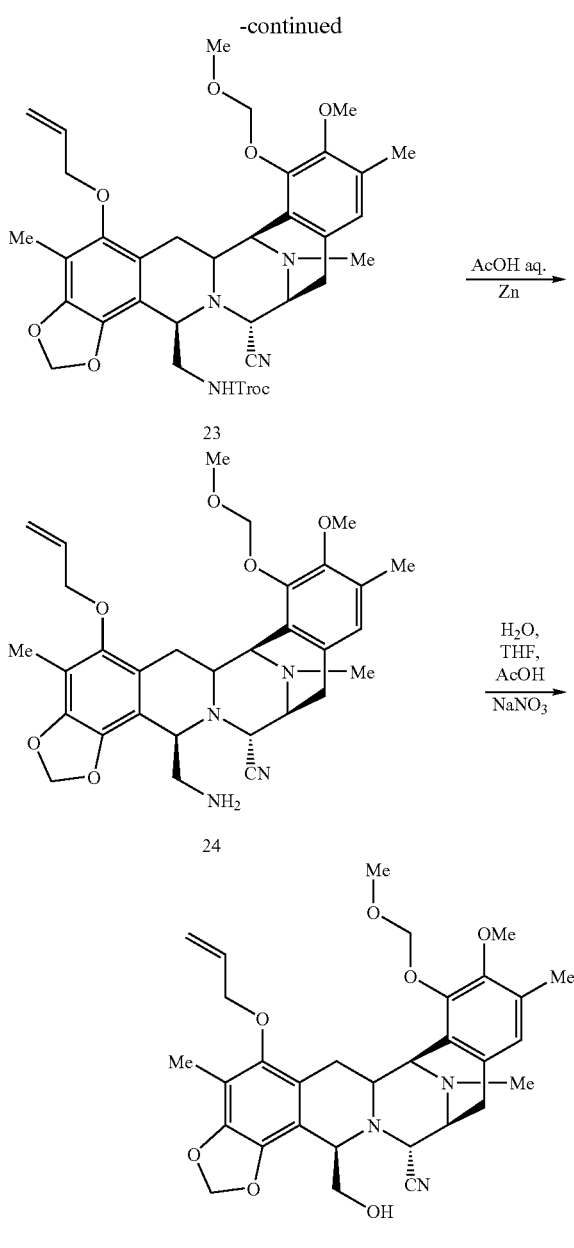

23

24

25

Scheme III

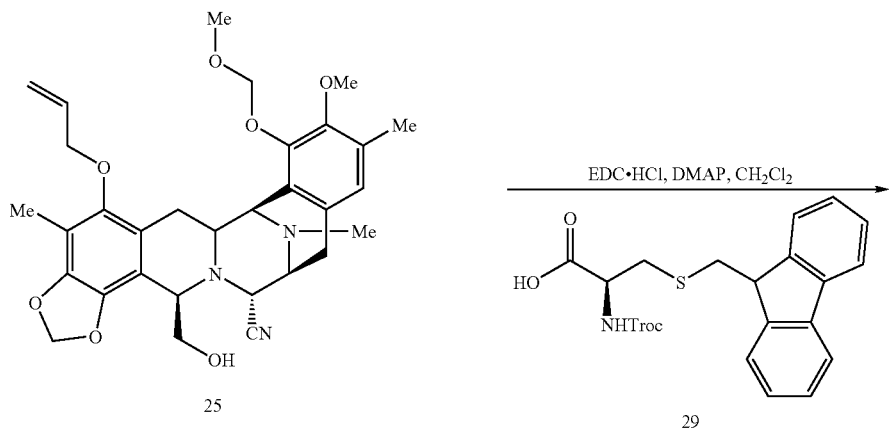

The conversion of the Intermediate 25 compound into ET-743 using cysteine derivative 29 usually involves the following steps (see scheme III):

transforming compound of formula 24 into the derivative 30 by protecting the primary hydroxyl function with (S)—N-2,2,2-trichloroethoxycarbonyl-S-(9H-fluoren-9-ylmethyl) cysteine 29;

converting the protected compound of formula 30 into the phenol derivative 31 by cleavage of the allyl group with tributyltin hydride and dichloropalladium-bis(triphenylphosphine);

transforming the phenol compound of Formula 31 into compound of formula 32 by oxidation with benzeneseleninic anhydride at low temperature;

transforming the hydroxy compound of formula 32 into the lactone 33 by the following sequence: (1) Reacting compound of formula 32 with 2 eq. of triflic anhydride and 5 eq. of DMSO. (2) followed by reaction with 8 eq. of diisopropylethylamine. (3) followed by reaction with 4 eq of t-butyl alcohol (4) followed by reaction with 7 eq of 2-tert-Butyl-1,1,3,3,tetramethylguanidine (5) followed by reaction with 10 eq of acetic anhydride;

transforming the lactone compound 33 into hydroxyl compound 34 by removal of MOM protecting group with TMSI;

cleaving the N-trichloroethoxycarbonyl group of the compound of formula 34 into compound 35 by reaction with Zn/AcOH;

transforming the amino compound 35 into the corresponding α-keto lactone compound 36 by reaction with N-methyl pyridinium carboxaldehyde chloride followed by DBU;

forming ET-770 by reacting compound of Formula 36 with 3-hydroxy-4-methoxyphenylethylamine;

transforming ET-770 into ET-743 by reaction with silver nitrate in a mixture of AcN/H$_2$O.

-continued
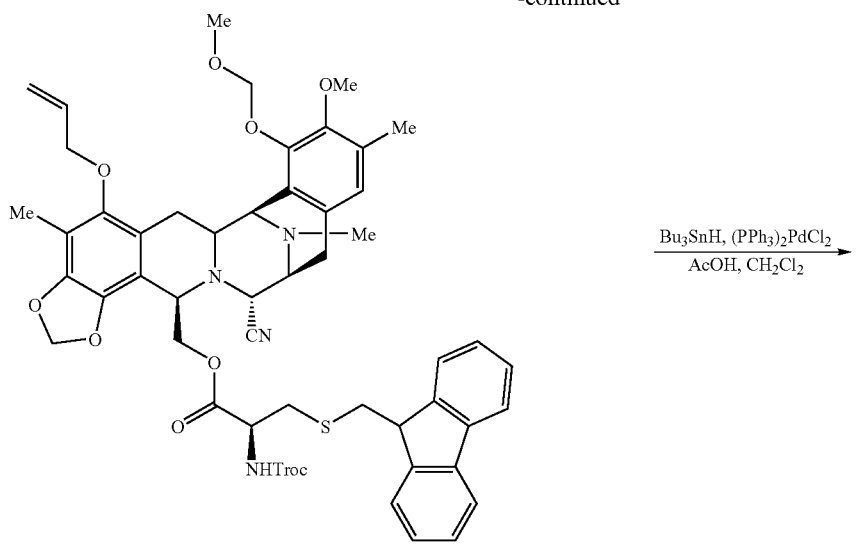
30
Bu₃SnH, (PPh₃)₂PdCl₂
———————————→
AcOH, CH₂Cl₂
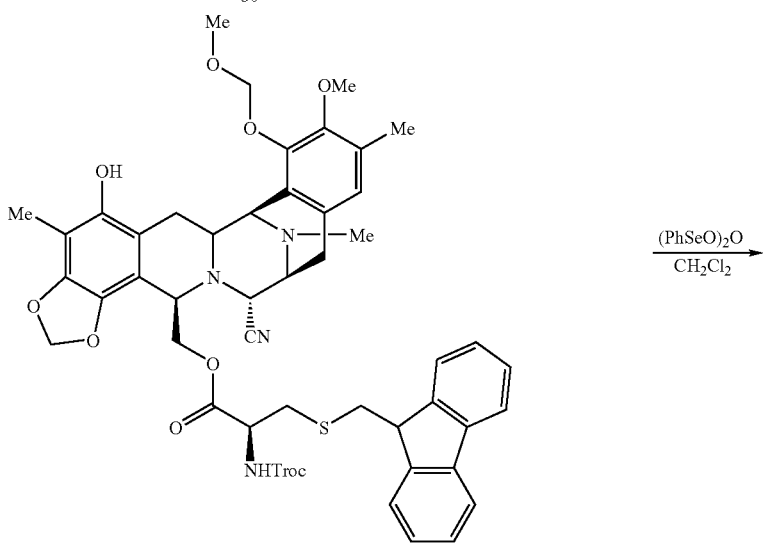
31
(PhSeO)₂O
————→
CH₂Cl₂
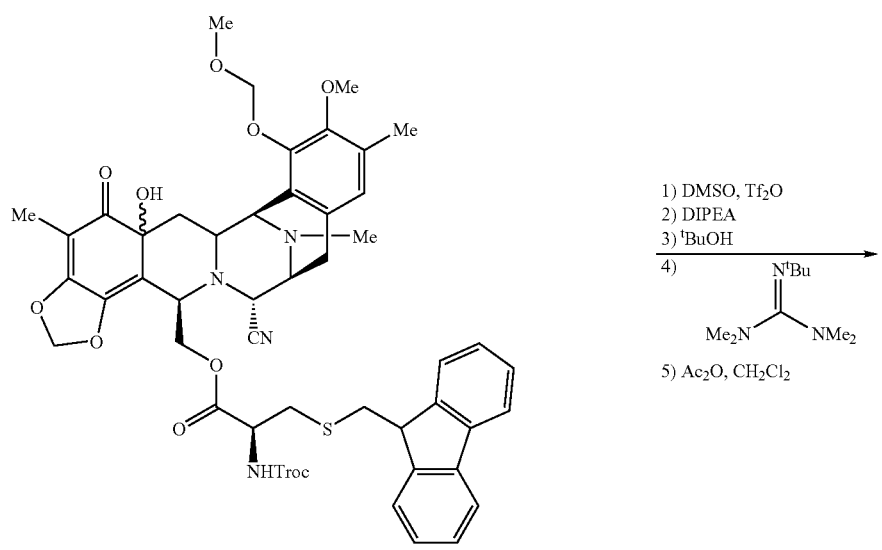
32
1) DMSO, Tf₂O
2) DIPEA
3) ᵗBuOH
4) Me₂N–C(=NᵗBu)–NMe₂
———————————→
5) Ac₂O, CH₂Cl₂

-continued
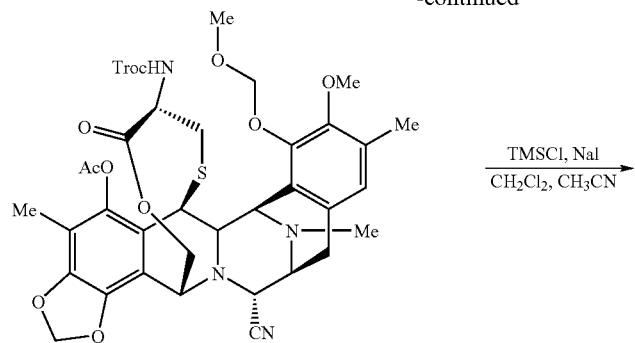
33
TMSCl, NaI
———————→
CH₂Cl₂, CH₃CN
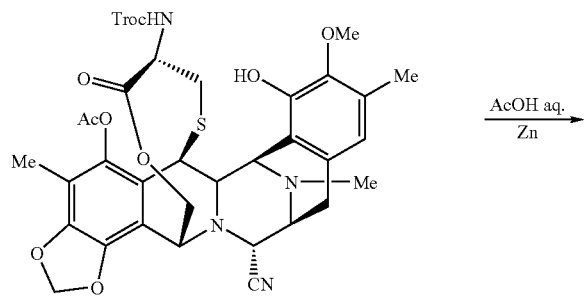
34
AcOH aq.
————→
Zn
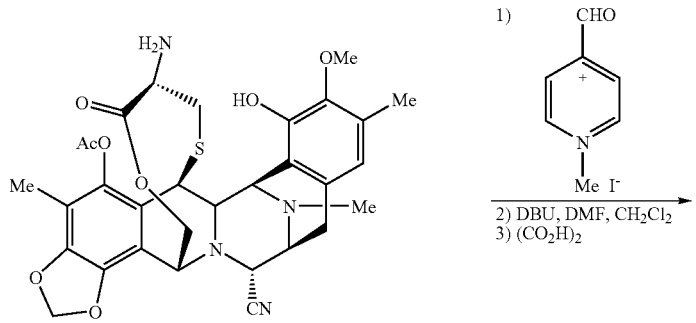
35
1) <small>pyridinium aldehyde reagent</small>
2) DBU, DMF, CH₂Cl₂
3) (CO₂H)₂
———————→
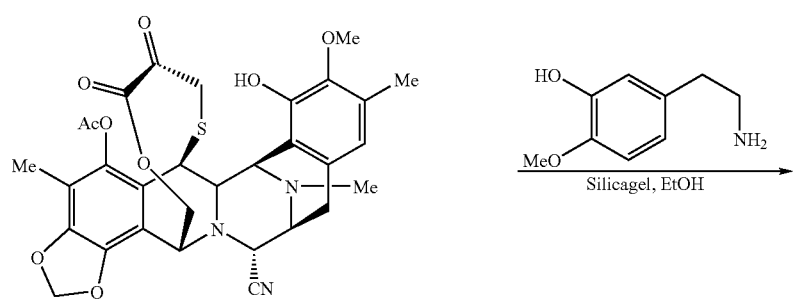
36
<small>HO-/MeO-phenethylamine</small>
————————→
Silicagel, EtOH

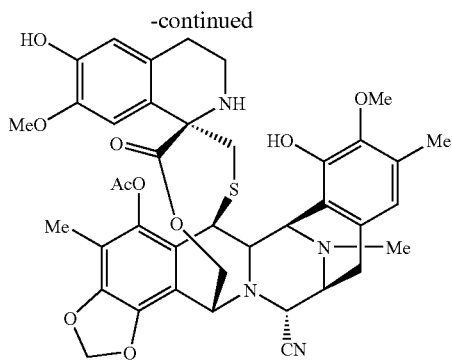
Et-770

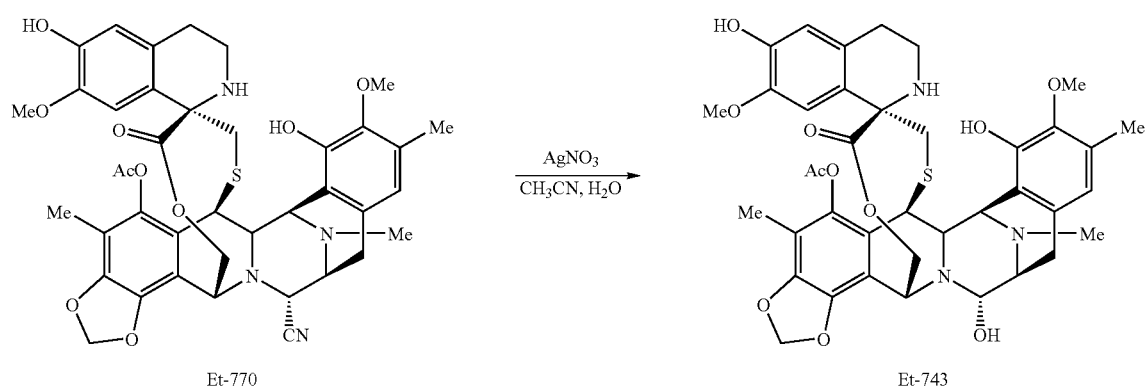
Et-770     AgNO₃ / CH₃CN, H₂O     Et-743

The route described above to transform Intermediate 25 into ET-743 can be conveniently modified using other cysteine derivatives, for example compound 37 named 2-methoxymethyloxy-3-(9H-fluoren-9-ylmethyl)-thio-propenoic acid. This compound has already incorporated a keto group in form of enol ether, while in the other cysteine analogs there is an amino that has to be transformed later into a keto group through a transamination reaction with a moderate yield of 55-60%. Therefore using compound 37 is possible to increase substantially the yield of the linear synthesis because the transamination step is avoided.

The conversion of the Intermediate compound 25 into ET-743 using cysteine derivative 37 can be made in a similar manner and with the same reagents than with cysteine derivative 29 with the exception of transformations (f) and (g). The reaction sequence is exemplified in the following scheme (Scheme IV):

Scheme IV

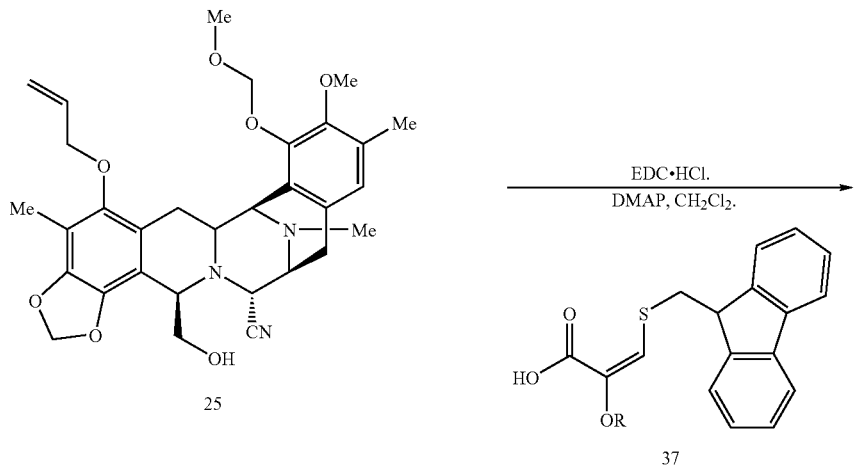

-continued
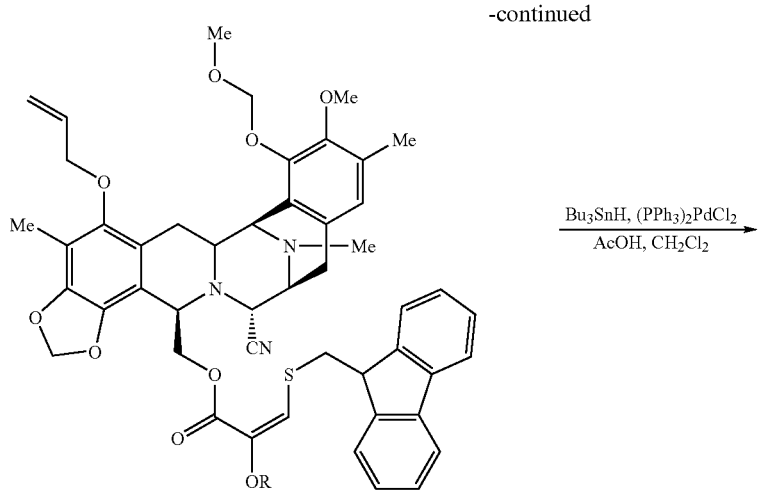
38
Bu₃SnH, (PPh₃)₂PdCl₂
———————————→
AcOH, CH₂Cl₂
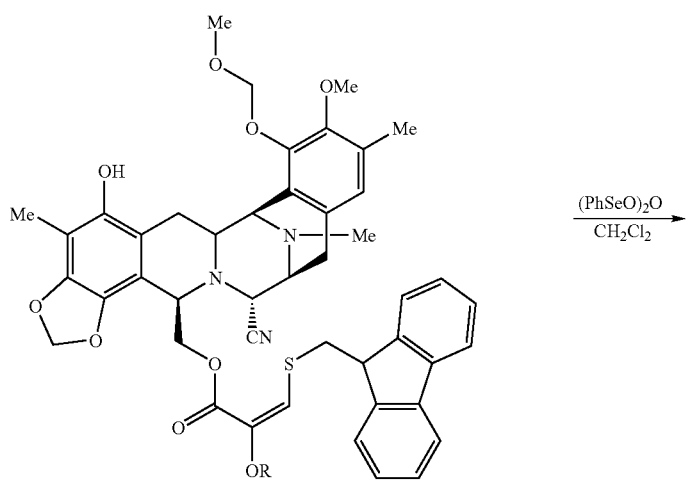
39
(PhSeO)₂O
————→
CH₂Cl₂
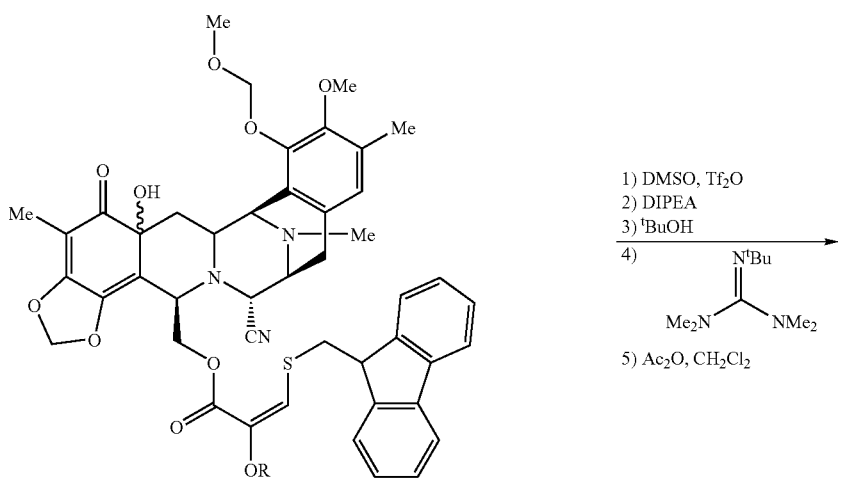
40
1) DMSO, Tf₂O
2) DIPEA
3) ᵗBuOH
4) Me₂N–C(=NᵗBu)–NMe₂
5) Ac₂O, CH₂Cl₂

-continued
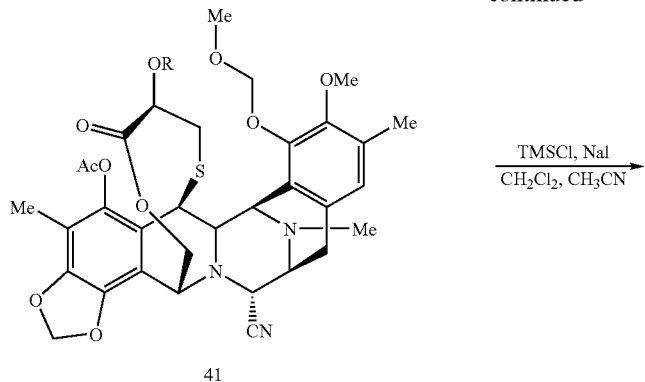
41
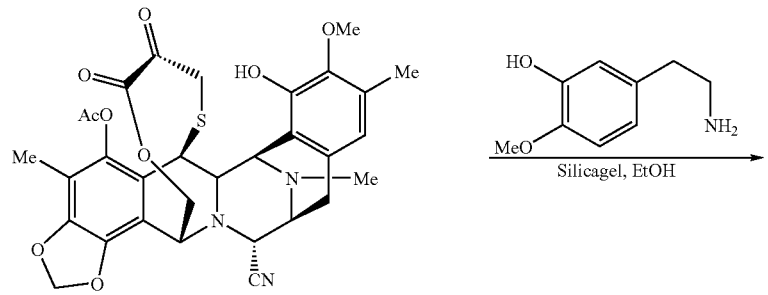
36
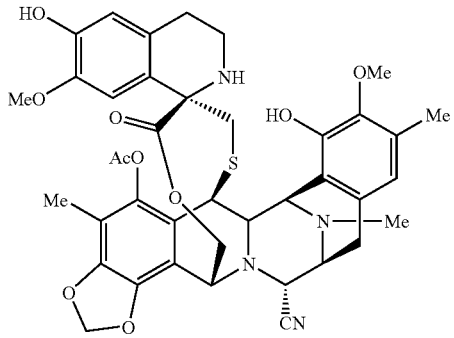
Et-770
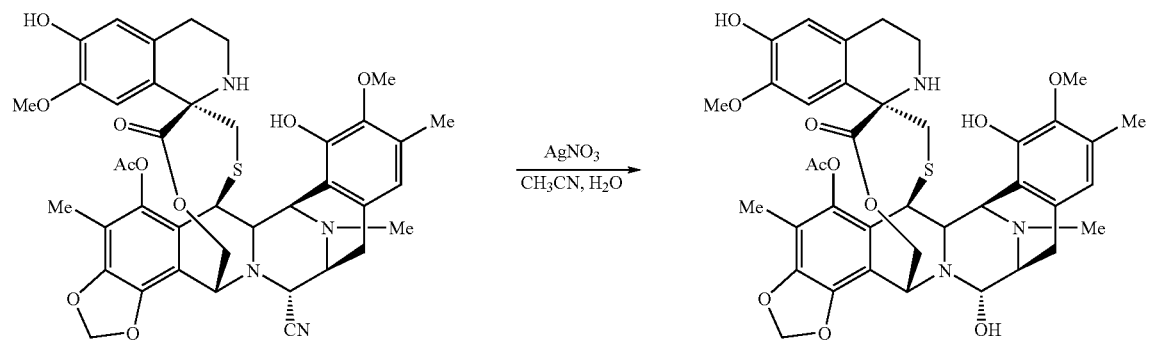
Et-770     Et-743

Compound 38 can also be formed reacting Intermediate 12 described in U.S. Pat. No. 5,721,362 with Intermediate 37 providing a improvement of the route described in that patent.

Formation of Phthalascidin and Related Compounds.

In the present invention, a key class of products includes phthalascidin and has the general formula (XX):

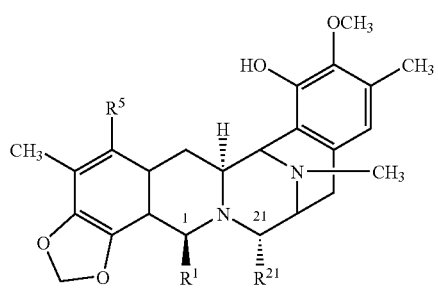

where $R^1$ is an amidomethylene group; $R^5$ is a small oxysidechain; and $R^{21}$ is a cyano group or a hydroxy group. For phthalascidin, $R^1$ is a phthalimidomethylene group; $R^5$ an acetoxy group; and $R^{21}$ is a cyano group. Other groups for $R^1$ include mono- and di-N-substituted amidomethylenes as well as other cyclic amidomethylenes, and other groups for $R^5$ include further $C_1$-$C_4$ acyl groups, as well as $C_1$-$C_4$ alkyl groups.

The conversion of the 21-cyano compound to phthalascidin or a related product of formula (XX) usually involves the following steps:

a) conversion if necessary of a quinone system for the ring E into the phenol system
b) formation of the —$R^5$ group at the 5-position in ring A;
c) formation of the $R^1$ group at the 1-position in ring B; and
d) conversion if necessary of a quinone system for the ring A into the phenol system;
e) conversion of the phenol system for the ring A into the methylenedioxyphenol ring.

These steps have many similarities with the steps given for formation of ecteinascidins. Step (c) typically involves forming a group —$CH_2NH_2$ at the 1-position and acylating it.

Phthlascidin can be made using Intermediates described in the conversion of cyanosafracin B into Intermediate 25. For example, Intermediates 21 and 17 are suitable starting materials to make Phthlascidin.

As shown above in scheme V, the process for the synthetic formation of phthlascidin starting from Intermediate 21 comprises the sequential steps of:

transforming of 21 into the compound of Formula 27 by reaction with phthalic anhydride in dichloromethane and carbonyldiimidazole.

converting of 27 into phthlascidin by reacting with tributyltin hydride and dichloro palladium-bis(triphenylphosphine) or basic media, followed by reaction with acetyl chloride.

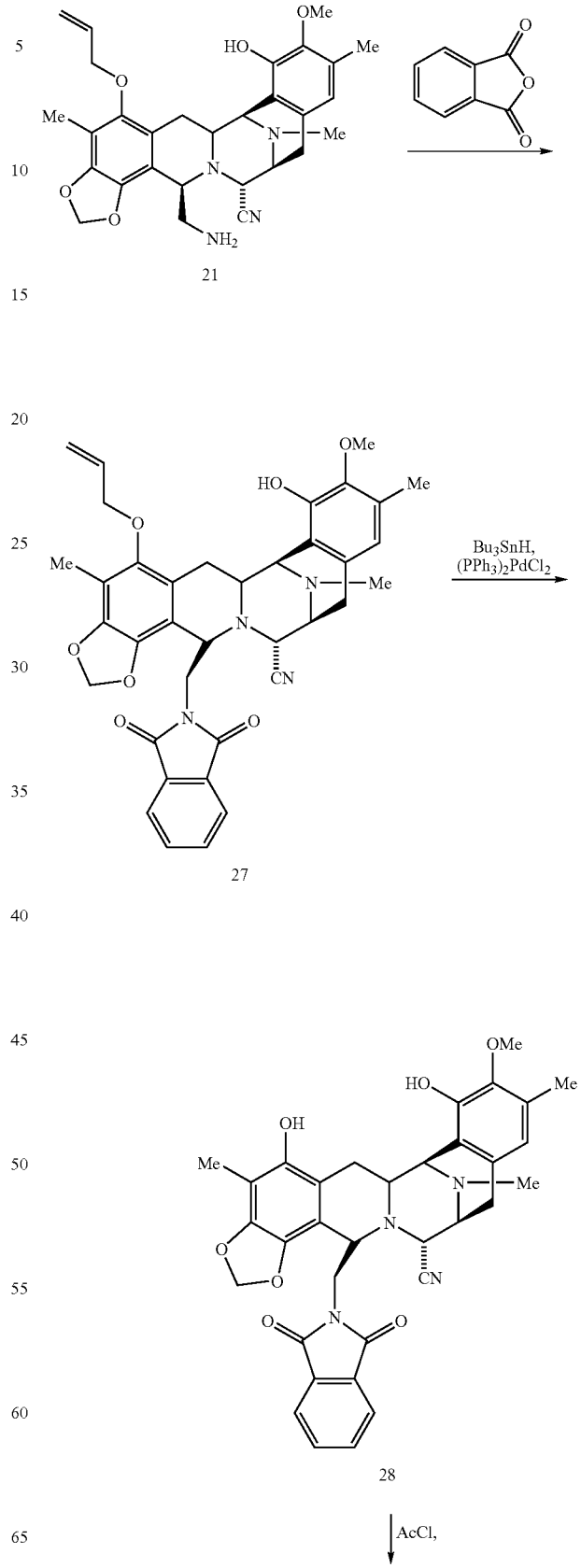

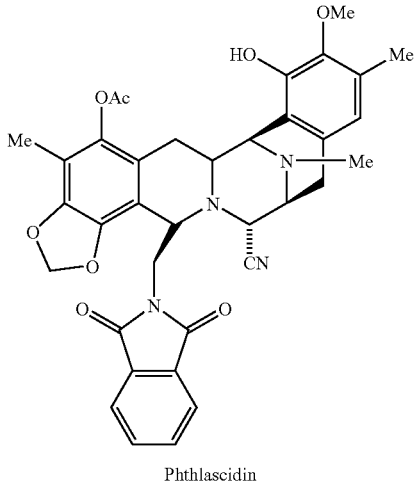

Phthlascidin

As shown above in scheme VI, the process for the synthetic formation of phthlascidin starting from Intermediate 17 comprises the sequential steps of:

acetylation of the hydroxyl group of compound of formula 17 with acetyl chloride and pyridine to give the acetylated intermediate compound of formula 42;

removal of the tert-butoxycarbonyl and the methyloxymethyl protecting groups of 42 to afford the compound of Formula 43 by reacting with a solution of HCl in dioxane. Also this reaction is achieved by mixing 42 with a solution of trifluoroacetic acid in dichloromethane;

formation of the thiourea compound of Formula 44 by reacting 43 with phenylisothiocyanate;

converting compound of Formula 44 into the amine compound of Formula 45 by reacting with a solution of hydrogen chloride in dioxane;

transforming of 45 into Phthlascidin by reaction with phthalic anhydride in dichloromethane and carbonyldiimidazole.

Scheme VI

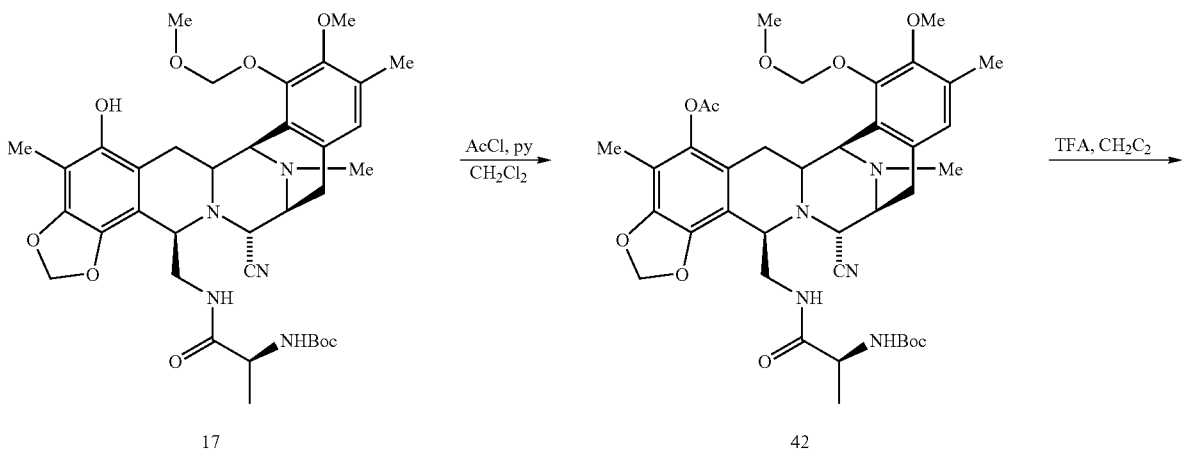

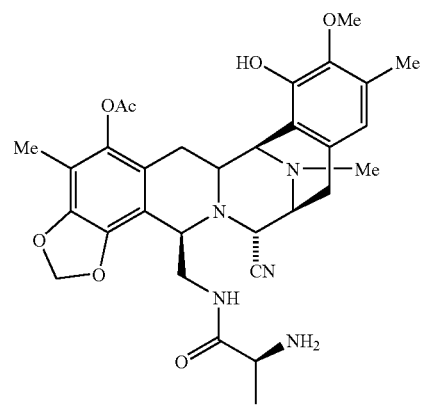

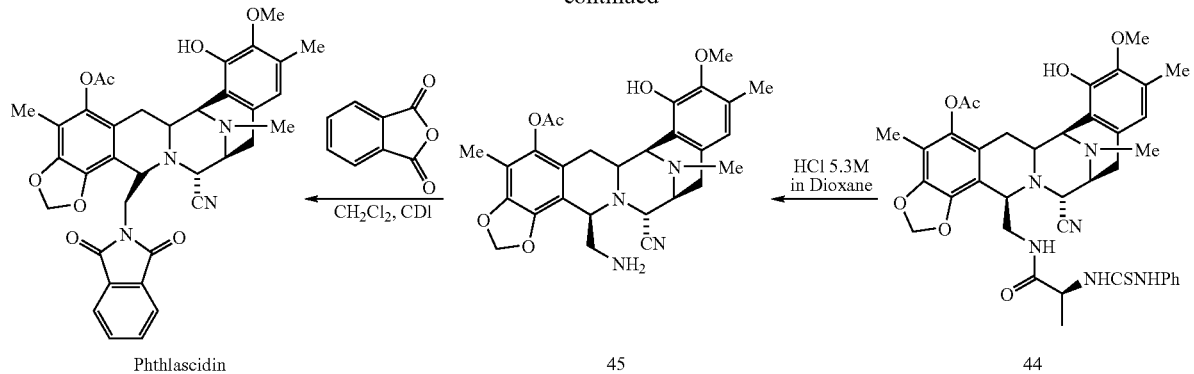

Formation of Intermediate 11 and Related Intermediates.

The retrosynthetic analysis is described in the following sequence.

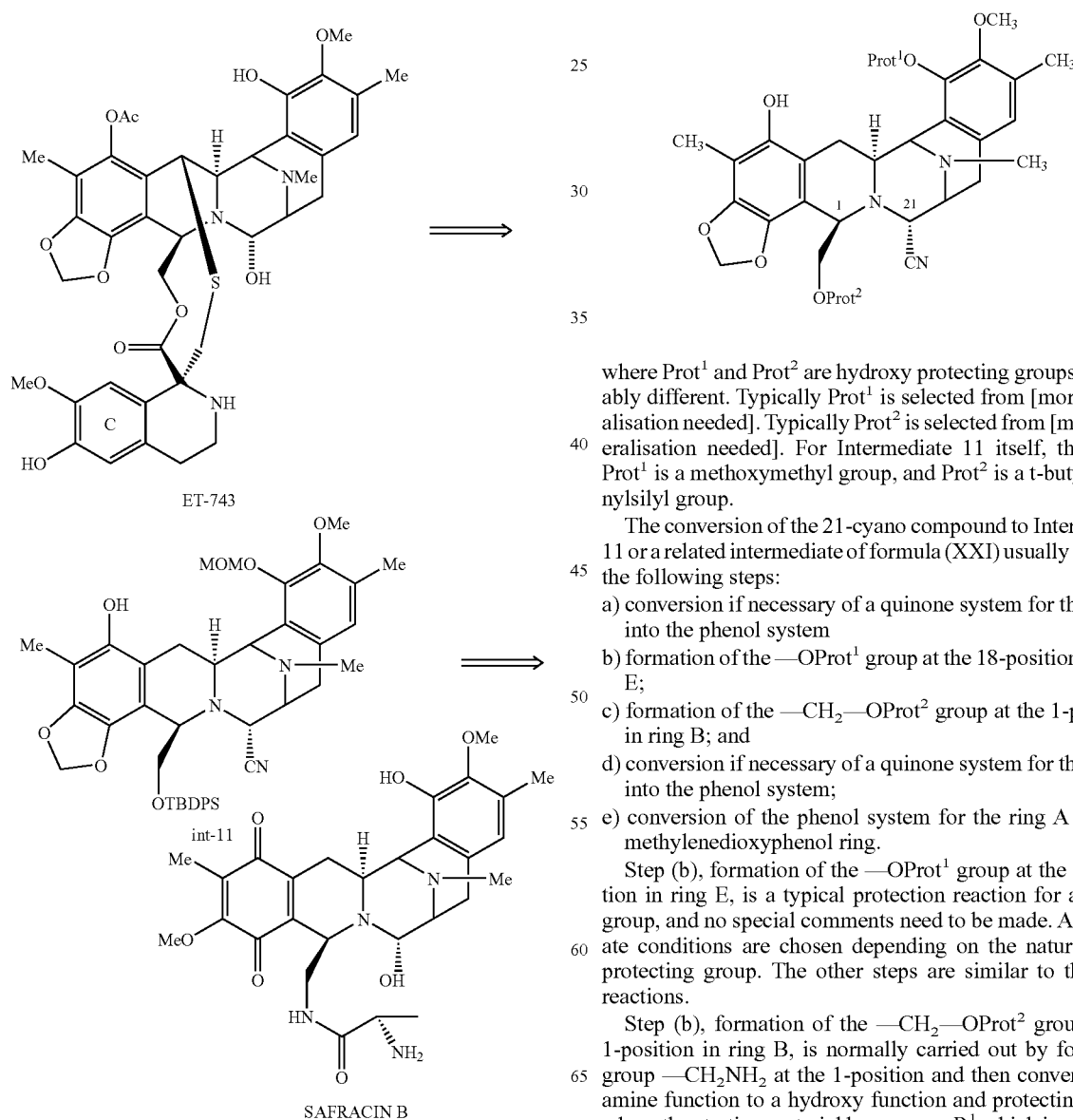

In the present invention, a key class of intermediate includes Intermediate 11 and has the general formula (XXI):

where $Prot^1$ and $Prot^2$ are hydroxy protecting groups, preferably different. Typically $Prot^1$ is selected from [more generalisation needed]. Typically $Prot^2$ is selected from [more generalisation needed]. For Intermediate 11 itself, the group $Prot^1$ is a methoxymethyl group, and $Prot^2$ is a t-butyldiphenylsilyl group.

The conversion of the 21-cyano compound to Intermediate 11 or a related intermediate of formula (XXI) usually involves the following steps:

a) conversion if necessary of a quinone system for the ring E into the phenol system
b) formation of the —$OProt^1$ group at the 18-position, in ring E;
c) formation of the —$CH_2$—$OProt^2$ group at the 1-position, in ring B; and
d) conversion if necessary of a quinone system for the ring A into the phenol system;
e) conversion of the phenol system for the ring A into the methylenedioxyphenol ring.

Step (b), formation of the —$OProt^1$ group at the 18-position in ring E, is a typical protection reaction for a phenol group, and no special comments need to be made. Appropriate conditions are chosen depending on the nature of the protecting group. The other steps are similar to the other reactions.

Step (b), formation of the —$CH_2$—$OProt^2$ group at the 1-position in ring B, is normally carried out by forming a group —$CH_2NH_2$ at the 1-position and then converting the amine function to a hydroxy function and protecting. Thus, where the starting material has a group $R^1$ which is —$CH_2$—

NH—CO—CR$^{25a}$R$^{25b}$R$^{25c}$ then it is matter of removing the N-acyl group. Where the starting material has a group R$^1$ which is —CH$_2$—O—CO—R then no change may be needed for an ecteinascidin product where the substituent R$^1$ is the same. For other products, it is matter of removing the O-acyl group. Various procedures are available for such deacylations. In one variation, the deacylation and conversion to a hydroxy function are performed in one step. Thereafter, the hydroxy group can be acylated or otherwise converted to give the appropriate R$^1$ group.

U.S. Pat. No. 5,721,362 describe synthetic methods to make ET-743 through a long multistep synthesis. One of the Intermediates of this synthesis is Intermediate 11. Using cyanosafracin B as starting material it is possible to reach Intermediate 11 providing a much shorter way to make such Intermediate and therefor improving the method to make ET-743

Cyanosafracin B can be converted into Intermediate 25 by the methods described above. From Intermediate 25 is possible to reach Intermediate 11 using the following steps, see scheme VII.

formation of the protected hydroxy compound of Formula 26 by reacting 25 with tert-butyldiphenylsilyl chloride in the presence of a base;

final cleavage of the allyl group with tributyltin hydride and dichloropalladium-bis(triphenylphosphine) in 26 that leads to the formation of the intermediate 11.

Scheme VII

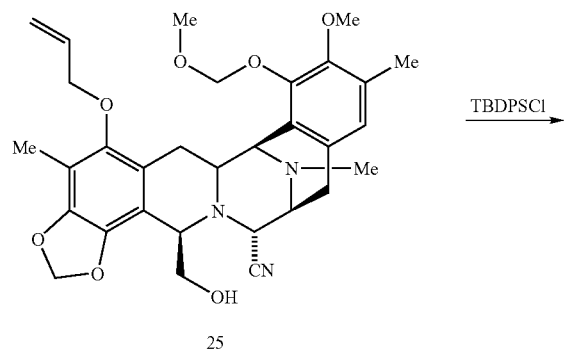

25

TBDPSCl

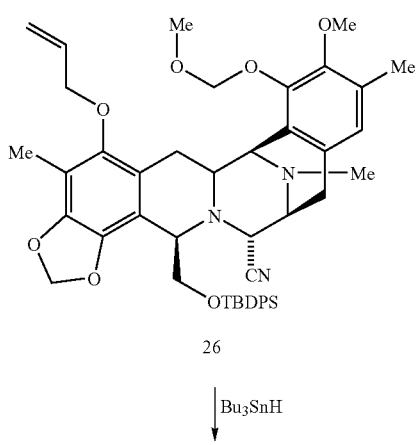

26

Bu$_3$SnH

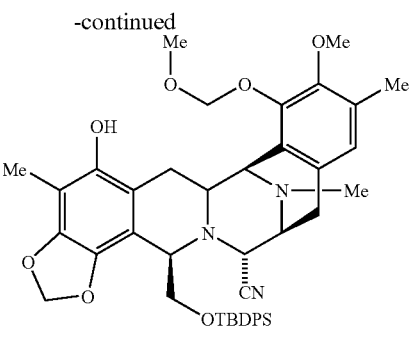

Int-11

One embodiment of the synthetic process of the present invention to transform safracin B into intermediate 11 is a modification and extension of Scheme VIII and comprises the sequential steps of:

stereospecifically converting the compound of Formula 1 (Safracin B) to the compound of Formula 2 by selective replacement of OH by CN by reacting with KCN in acid media;

forming the thiourea compound of Formula 3 by reacting compound of Formula 2 with phenyl isothiocyanate;

converting the thiourea compound of Formula 3 into the acetamide of Formula 5 by an hydrolysis in acid media followed by addition of acetic anhydride; The intermediate amine compound of Formula 4 can be isolated by quenching the hydrolysis in acid media with sodium bicarbonate, but this intermediate is highly unstable, and is transformed quickly into a five member cyclic imine, named compound 6;

forming the protected compound of Formula 7 by reacting with bromomethylmethyl ether and diisopropylethylamine in dichloromethane;

selectively de-methylating the methoxy group of the quinone system of compound of Formula 7 into the compound of Formula 8 by reacting with methanolic solution of sodium hydroxide;

transforming the compound of Formula 8 into methylenedioxy-compound of Formula 9 by the preferred following sequence: (1) quinone group of compound 8 is reduced with 10% Pd/C under hydrogen atmosphere; (2) the hydroquinone intermediate is converted into the methylenedioxy compound of Formula 9 by reacting with bromochloromethane and cesium carbonate under hydrogen atmosphere; (3) compound of Formula 9 is transformed into compound of Formula 10 by protecting the free hydroxyl group as a OCH$_2$R group, by reacting with BrCH$_2$R and cesium carbonate, where R can be aryl, CH═CH$_2$, OR' etc.;

converting the acetamide group of compound of Formula 10 into the corresponding hydroxyl group of Formula 11 by reaction with nitrogen tetroxide in a mixture of acetic acid and acetic acetate followed by treatment with sodium hydroxide; alternatively can be used sodium nitrite in a mixture of acetic anhydride acetic acid, followed by treatment with sodium hydroxide;

alternatively the acetamide group of compound of Formula 10 can be converted into the primary amine group by reacting with hydrazine or with Boc$_2$O, DMAP followed by hydrazine; such primary amine can be converted into the corresponding hydroxyl group (compound of Formula 11) by an oxidative conversion of the primary amine into the corresponding aldehyde with 4-formyl-1-methylpyridinium benzenesulphonate or other pyridinium ion, followed by DBU or other base treatment and further hydrolization, and followed by the reduction of the aldehyde to the corresponding hydroxyl group with lithium aluminium hydride or other reducing agent;

forming the protected compound of Formula 26 by reacting with t-butyldiphenylsilyl chloride and dimethylaminopyridine in dichloromethane;

transforming the silylated compound of Formula 26 into the intermediate 11 by deprotection of the OCH$_2$R protecting group, by reacting under reductive conditions or acid conditions. Typical procedures are with palladium black under hydrogen atmosphere, or aqueous TFA, or tributyltin hydride and dichlorobis(triphenylphosphine palladium).

In yet another preferred modification, the cyano compound of Formula 2 can be transformed into Intermediate 11 using an extension of the scheme II, involving the further steps of:

formation of the protected hydroxy compound of Formula 26 by reacting 25 with tert-butyldiphenylsilyl chloride in the presence of a base;

final cleavage of the allyl group with tributyltin hydride and dichloropalladium-bis(triphenylphosphine) in 26 that leads to the formation of the intermediate 11.

Formation of Active Compounds

It is possible to transform cyanosafracin B into a number of intermediates and derivatives with potential antitumor therapeutic activity. These intermediates can be made starting from already described compounds, or using alternative routes.

Intermediates described herein comprise compound 47, and a numbers of amide derivatives made using compounds 45 or 43.

In Scheme VIII is described formation of compound 47 using the following sequence:

forming the thiourea compound of Formula 3 by reacting compound of Formula 2 with phenyl isothiocyanate;

converting the thiourea compound of Formula 3 into the acetamide of Formula 5 by an hydrolysis in acid media followed by addition of acetic anhydride; The intermediate amine compound of Formula 4 can be isolated by quenching the hydrolysis in acid media with sodium bicarbonate, but this intermediate is highly unstable, and is transformed quickly into a five member cyclic imine, named compound 6;

forming the protected compound of Formula 7 by reacting with bromomethylmethyl ether and diisopropylethylamine in dichloromethane;

selectively de-methylating the methoxy group of the quinone system of compound of Formula 7 into the compound of Formula 8 by reacting with methanolic solution of sodium hydroxide;

transforming the compound of Formula 8 into methylenedioxy-compound of Formula 10 by the preferred following sequence: (1) quinone group of compound 8 is reduced with 10% Pd/C under hydrogen atmosphere; (2) the hydroquinone intermediate is converted into the methylenedioxy compound of Formula 9 by reacting with bromochloromethane and cesium carbonate under hydrogen atmosphere; (3) compound of Formula 9 is transformed into compound of Formula 10 by protecting the free hydroxyl group as a allyloxy group, by reacting with allylbromide and cesium carbonate;

transforming the compound of formula 9 into acetyl-derivative 46 by reaction with acetyl chloride in pyridine;

transforming compound of formula 46 into de-protected compound 47 by reaction with hydrochloric acid in dioxane.

Scheme VIII

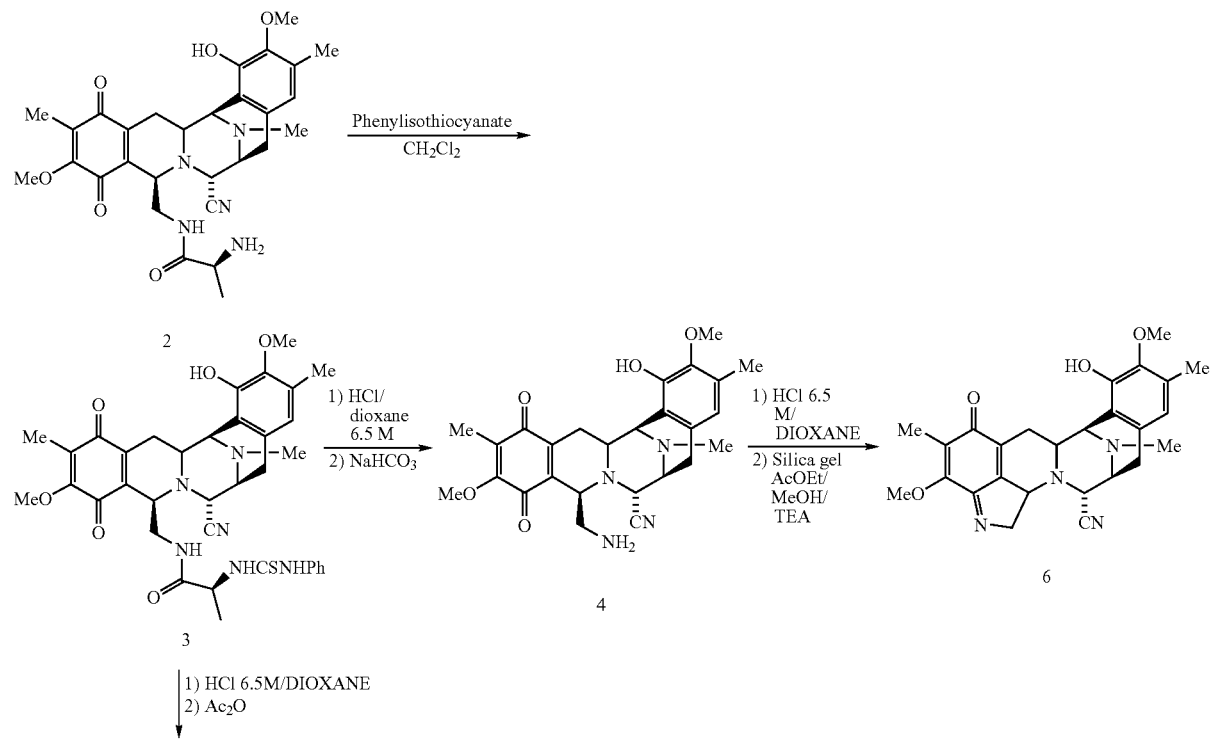

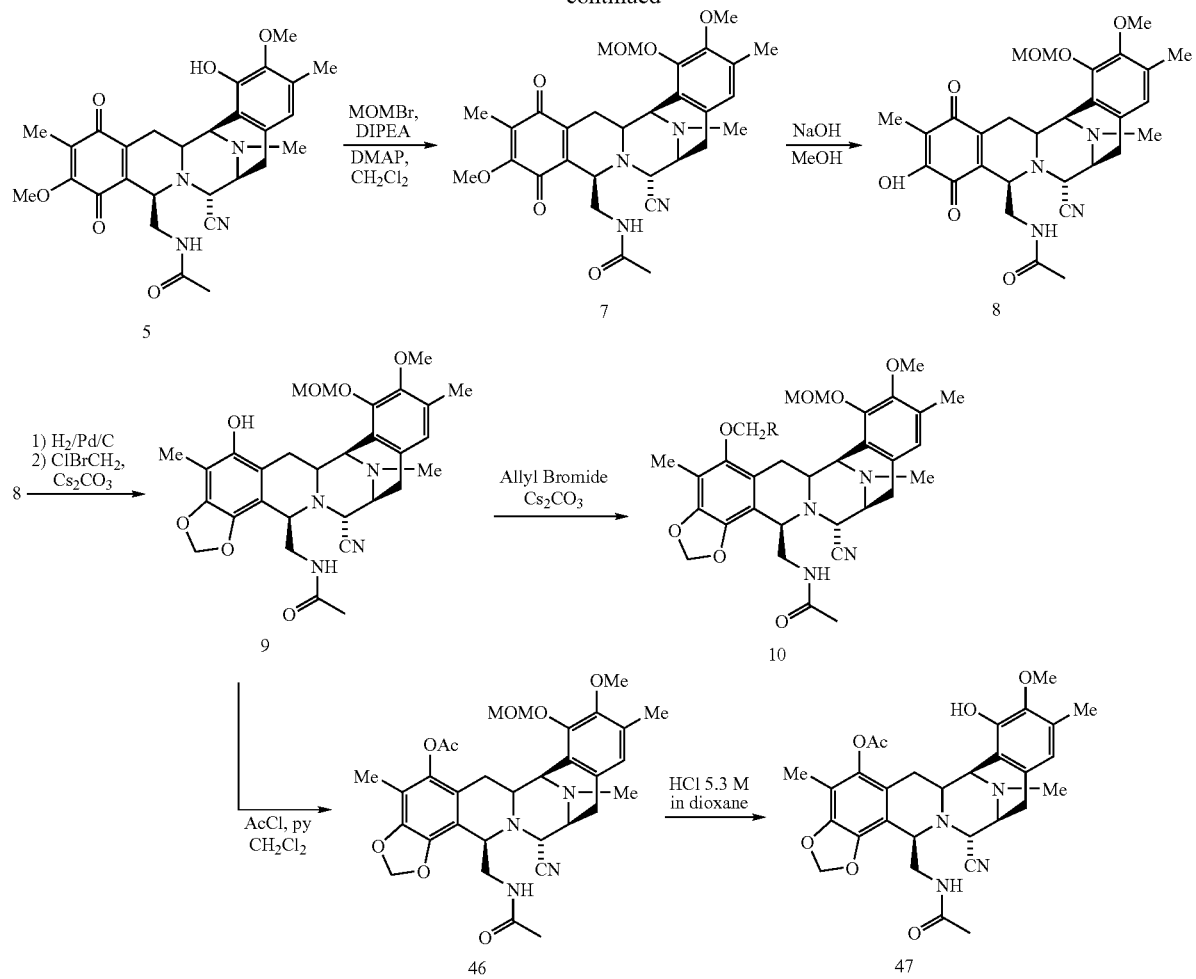
Other useful amide intermediate derivatives are made starting from already described intermediate 45 using the next scheme:
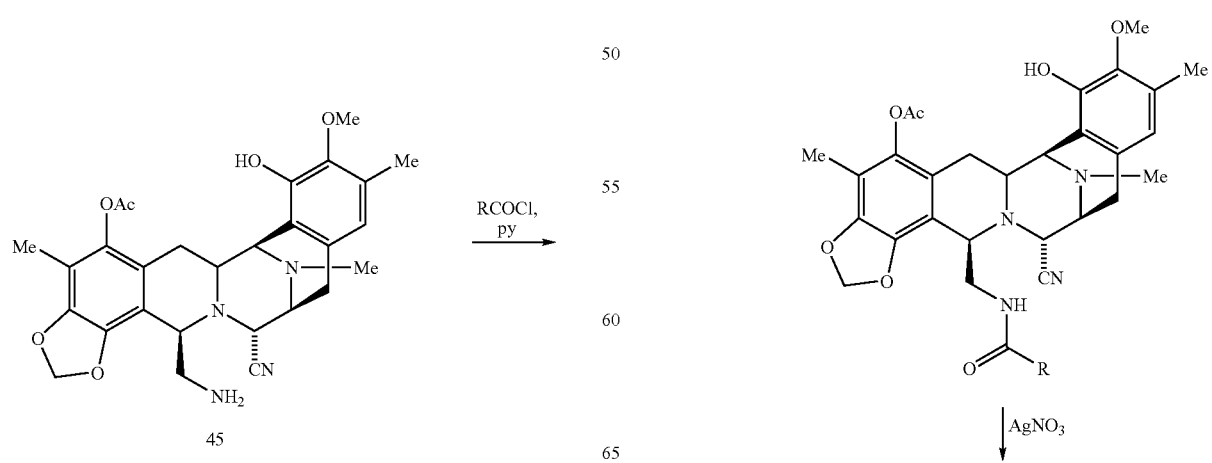

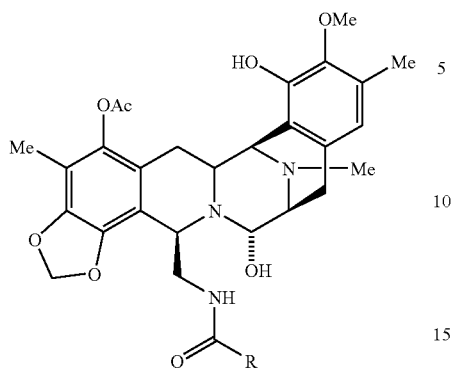

The second step is optional. This process is an important part of the invention, particularly where the group R is a group $R^a$ as previously defined. Furthermore, the Scheme VIII can be readily broadened to enable preparation of compounds of formula (XXIII), by inclusion in the starting material of a different group at the 5-position, either a group directly intended for the product or a group which can be removed or otherwise modified to give the desired group.

Scheme IX

From compound 45 can be made a group of analogs through the following sequence:

acylation in the amino group of compound of Formula 45 by a wide range of acyl derivatives to provide the corresponding amides, where preferred acyl groups are acetyl, cinnamoyl chloride, p-trifluorocinnamoyl chloride, isovaleryl chloride phenylisothiocyanate or aminoacids, or the other examples previously given of groups $R^aCO—$.

transforming the CN group into an OH group by reaction with silver nitrate in a mixture $AcN/H_2O$.

Other useful amide intermediate derivatives are made starting from already described intermediate 43 using the next scheme:

Scheme X

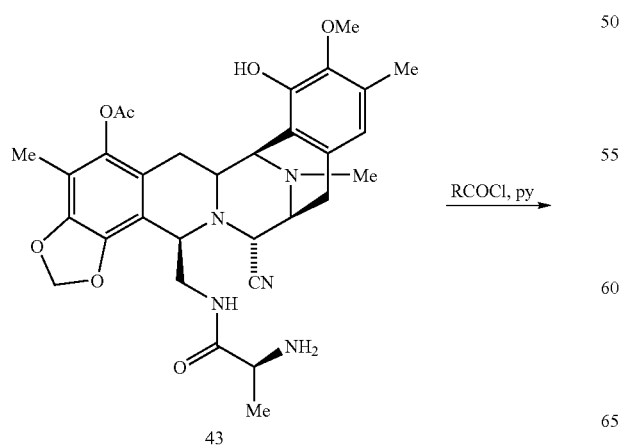

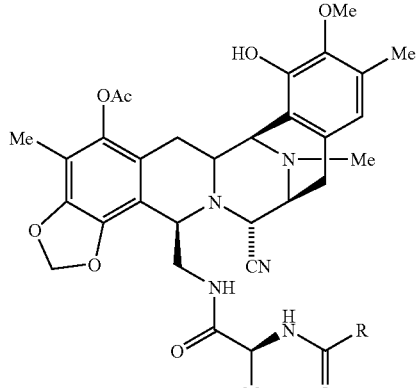

From Compound 43 can be obtained another group of interesting derivatives using the following sequence:

(a) acylation in the amino group of compound of Formula 43 by a wide range of acyl derivatives to provide the corresponding amides, where preferred acyl groups are acetyl, cinnamoyl chloride, p-trifluorocinnamoyl chloride, isovaleryl chloride or aminoacids, or the other examples previously given of groups $R^aCO—$.

(b) transforming the CN group into an OH group by reaction with silver nitrate in a mixture $AcN/H_2O$ Novel Intermediate Compounds In the light of the preceding explanations, it can be seen that the present invention provides novel intermediate compounds. Depending on ring A, the intermediates are of formula (XXIIa):

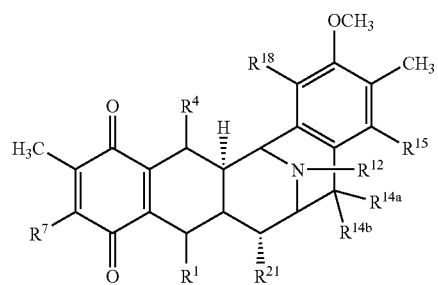

or of formula (XXIIb):

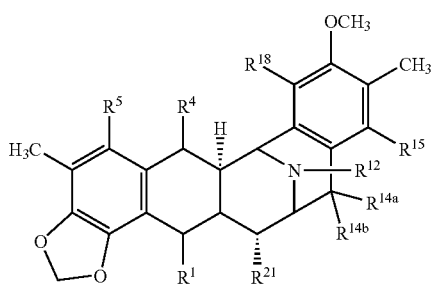

where:
$R^1$ is —CH$_2$NH$_2$ or —CH$_2$OH, or a protected or derivatised version of such a group and $R^4$ is —H; or
$R^{1a}$ and $R^4$ together form a group of formula (IV), (VI) or (VII):

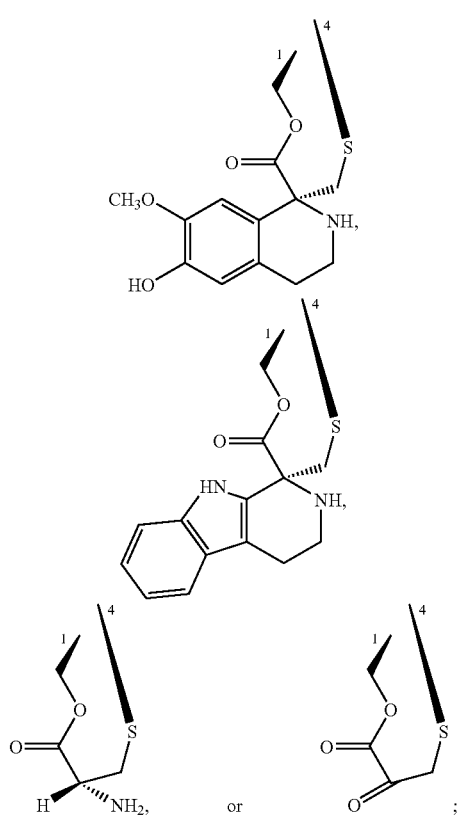

$R^5$ is —OH or a protected or derivatised version of such a group;
$R^{14a}$ and $R^{14b}$ are both —H or one is —H and the other is —OH or a protected or derivatised version of such a group, —OCH$_3$ or —OCH$_2$CH$_3$, or $R^{14a}$ and $R^{14b}$ together form a keto group;
$R^{12}$ is —NH—, —NCH$_3$— or —NCH$_2$CH$_3$—;
$R^{15}$ is —OH or a protected or derivatised version of such a group; and
$R^{18}$ is —OH or a protected or derivatised version of such a group.

In one embodiment, preferably at least of $R^1$, $R^5$, $R^{14a}$, $R^{14b}$, $R^{15}$ or $R^{18}$ is a protected or derivatised group.

In one variation of this invention, the group $R^1$ is not a 3,5-t-butyldiphenylsilyl substituent and/or the group $R^{18}$ is not a methoxymethyl group.

Preferably $R^1$ is —CH$_2$NH$_2$ or —CH$_2$OH, or a protected or derivatised version of such a group and $R^4$ is —H; or
$R^{1a}$ and $R^4$ together form a group:

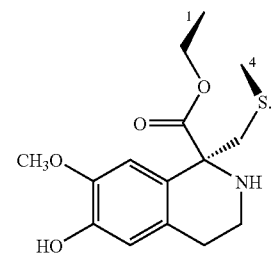

Preferably $R^{14a}$ and $R^{14b}$ are both —H.
One preferred class of intermediates includes the compound which we identify as compound 25, of formula:

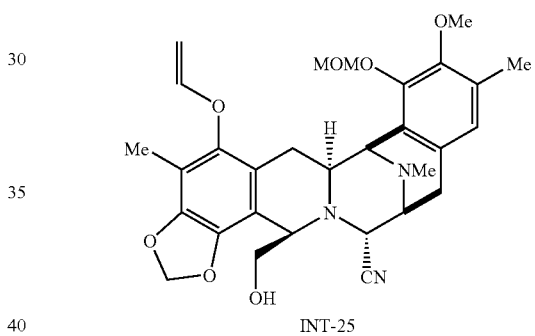

INT-25

The preferred class is thus of the general formula where the group MOM is replaced by any other protecting group.

Other preferred intermediates includes the compounds which we identify as compound 45 and 47. Other N-acyl derivatives may readily be made from compound 45 and are an important part of this invention. Suitable acyl groups include those previously mentioned. The corresponding 21-hydroxy compounds are also useful and are among the active compounds which we have found.

Novel Active Compounds

We have additionally found that certain of the compounds of the invention which we initially prepared as intermediates have exceptional activity in the treatment of cancers, such as leukaemias, lung cancer, colon cancer, kidney cancer and melanoma.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
b) antimetabolite drugs such as 5-fluorouracil, cytarabine, gemcitabine, purine analogues such as pentostatin, methotrexate);
c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably the didemnins such as aplidine;
m) steroid analogues, in particular dexamethasone;
n) anti-inflammatory drugs, in particular dexamethasone; and
o) anti-emetic drugs, in particular dexamethasone.

The present invention also extends to the compounds of the invention for use in a method of treatment, and to the use of the compounds in the preparation of a composition for treatment of cancer.

Cytotoxic Activity

Cell Cultures. Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin-G+streptomycin sulfate.

A simple screening procedure has been carried out to determine and compare the antitumour activity of these compounds, using an adapted form of the method described by Bergeron et al (1984). The tumour cell line employed have been P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cell were seeded into 16 mm wells at $1 \times 10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 were seeded into 16 mm wells at $2 \times 10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

1. Raymond J. Bergeron, Paul F. Cavanaugh, Jr., Steven J. Kline. Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121(3), 848-854.

2. Alan C. Schroeder, Robert G. Hughes, Jr. and Alexander Bloch. Effects of Acyclic Pyrimidine Nucleoside Analoges. *J. Med. Chem.* 1981, 24 1078-1083.

Cytotoxic Activity
| Compound | IC$_{50}$ (μM) | | | | | |
|---|---|---|---|---|---|---|
| | P-388 | A-549 | HT-29 | MEL-28 | CV-1 | DU-145 |
| 2 | 0.009 | 0.018 | 0.018 | 0.018 | 0.023 | |
| 14 | 0.15 | >0.15 | 0.15 | >0.15 | | |
| 15 | 1.44 | 1.44 | 1.44 | 1.44 | | |
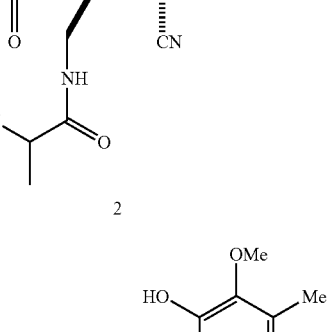
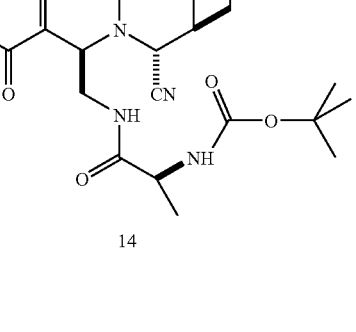
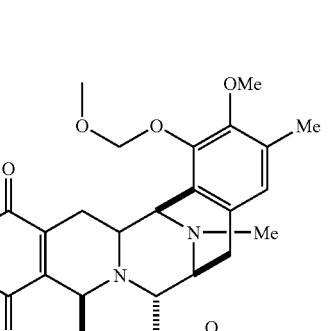

-continued

| Compound | IC$_{50}$ (μM) | | | | | |
|---|---|---|---|---|---|---|
| | P-388 | A-549 | HT-29 | MEL-28 | CV-1 | DU-145 |
| 16 | >1.5 | >1.5 | >1.5 | >1.5 | | |
| 17 | 1.4 | 1.4 | 1.4 | 1.4 | | |
| 18 | 0.01 | 0.01 | 0.01 | 0.01 | | |

| Compound | IC$_{50}$ (μM) | | | | | |
|---|---|---|---|---|---|---|
| | P-388 | A-549 | HT-29 | MEL-28 | CV-1 | DU-145 |
| 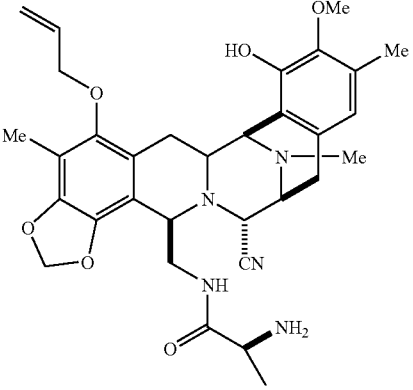 19 | 0.08 | 0.16 | 0.01 | 0.16 | | |
| 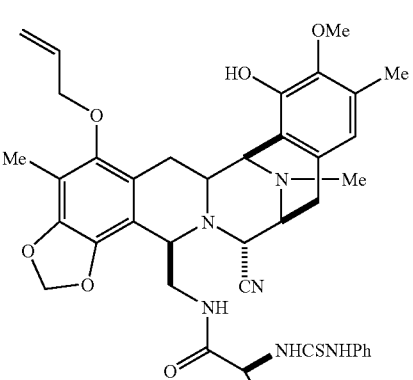 20 | 0.01 | 0.01 | 0.01 | 0.01 | | |
| 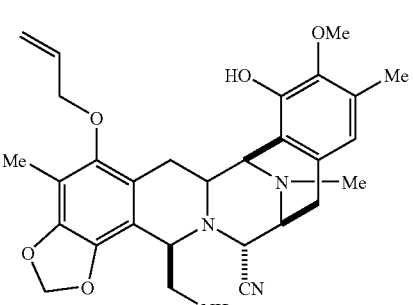 21 | 0.019 | 0.019 | 0.019 | 0.019 | | |

-continued
| Compound | IC$_{50}$ (μM) | | | | | |
|---|---|---|---|---|---|---|
| | P-388 | A-549 | HT-29 | MEL-28 | CV-1 | DU-145 |
| 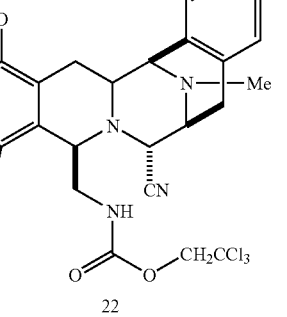 22 | 0.014 | 0.014 | 0.014 | 0.014 | 0.014 | 0.014 |
| 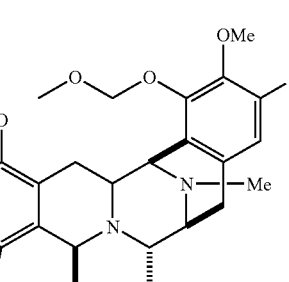 23 | 0.13 | 0.13 | 0.13 | 0.13 | 0.13 | 0.13 |
| 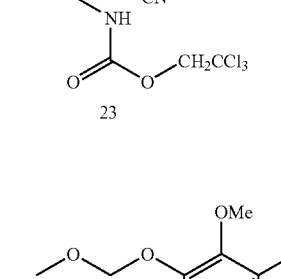 24 | 0.18 | 1.8 | 1.8 | 1.8 | 1.8 | 1.8 |
| 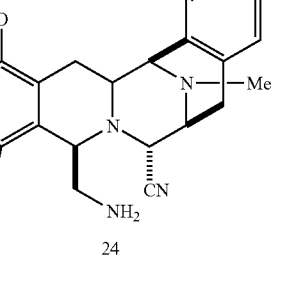 25 | 0.2 | 0.2 | 0.2 | 0.2 | | 0.2 |

| Compound | IC$_{50}$ (μM) | | | | | |
|---|---|---|---|---|---|---|
| | P-388 | A-549 | HT-29 | MEL-28 | CV-1 | DU-145 |
| 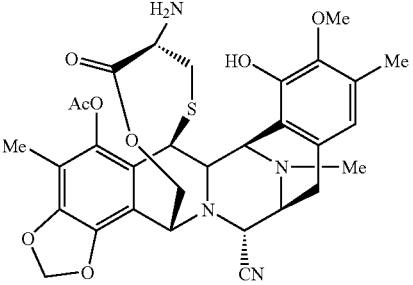 35 | 0.008 | 0.008 | 0.008 | 0.008 | | |
| 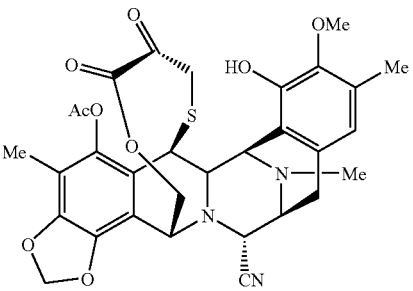 36 | 0.01 | 0.01 | 0.01 | 0.01 | | |
| 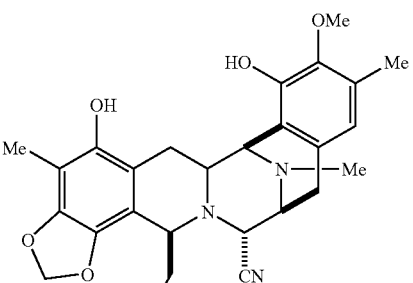 28 | 0.001 | 0.001 | 0.001 | 0.001 | 0.001 | 0.001 |
| 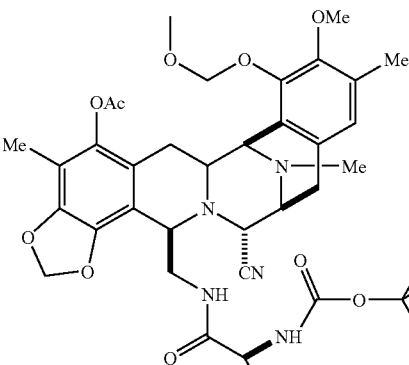 42 | 0.13 | 0.13 | 0.13 | 0.13 | | 0.13 |

-continued
| Compound | IC$_{50}$ (μM) | | | | | |
|---|---|---|---|---|---|---|
| | P-388 | A-549 | HT-29 | MEL-28 | CV-1 | DU-145 |
| 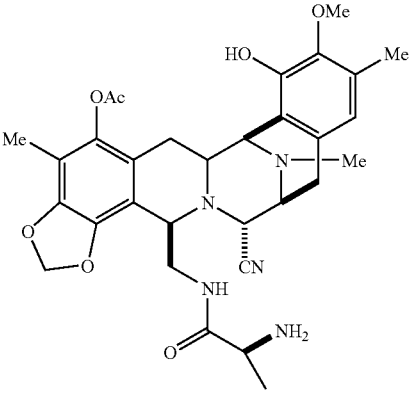 43 | 0.008 | 0.016 | 0.008 | 0.008 | | 0.016 |
| 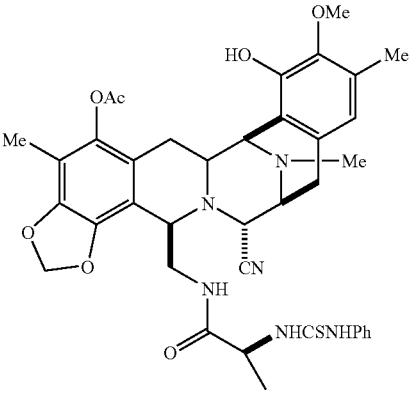 44 | 0.001 | 0.001 | 0.001 | 0.001 | | 0.001 |
| 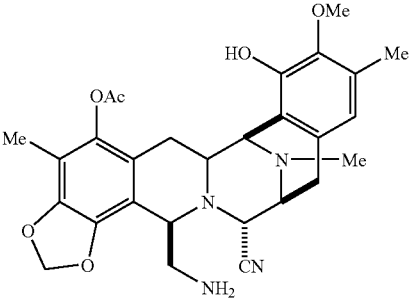 45 | 0.01 | 0.01 | 0.01 | 0.01 | | 0.01 |

-continued
| Compound | IC₅₀ (μM) | | | | | |
|---|---|---|---|---|---|---|
| | P-388 | A-549 | HT-29 | MEL-28 | CV-1 | DU-145 |
| 3 | 0.015 | 0.015 | 0.015 | 0.015 | 0.018 | |
| 6 | 2.171 | 2.171 | 2.171 | 2.171 | 2.171 | |
| 5 | 0.005 | 0.005 | 0.005 | 0.005 | | |
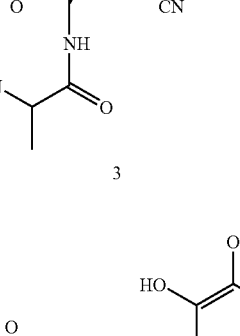
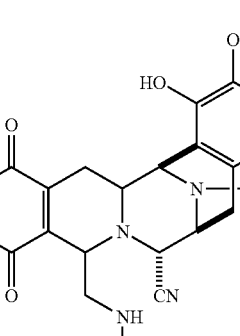

-continued

| Compound | IC$_{50}$ (μM) | | | | | |
|---|---|---|---|---|---|---|
| | P-388 | A-549 | HT-29 | MEL-28 | CV-1 | DU-145 |
| 7 | 0.22 | 0.22 | 0.22 | 0.22 | 0.22 | |
| 8 | >9 | >18.1 | >18.1 | >18.1 | >18.1 | |
| 9 | >1.77 | >1.77 | >1.77 | >1.77 | | >1.77 |

| Compound | IC₅₀ (μM) | | | | | |
|---|---|---|---|---|---|---|
| | P-388 | A-549 | HT-29 | MEL-28 | CV-1 | DU-145 |
| 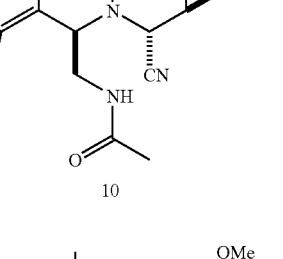 10 | >1.65 | >1.65 | >1.65 | >1.65 | | >1.65 |
| 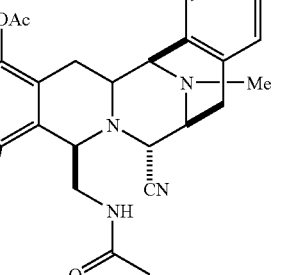 46 | 0.016 | 0.016 | 0.016 | 0.016 | | 0.016 |
| 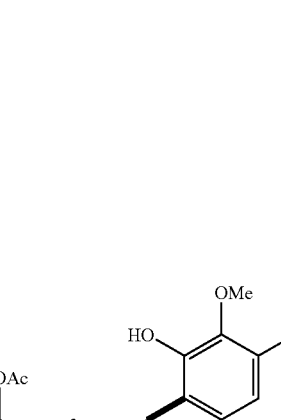 47 | 0.001 | 0.001 | 0.001 | 0.001 | | 0.001 |

-continued

| Compound | IC$_{50}$ (μM) | | | | | |
|---|---|---|---|---|---|---|
| | P-388 | A-549 | HT-29 | MEL-28 | CV-1 | DU-145 |
| 48 | 0.0008 | 0.001 | 0.0008 | 0.0008 | | 0.001 |
| 49 | 0.007 | 0.007 | 0.007 | 0.007 | | 0.007 |
| 50 | 0.0001 | 0.0001 | 0.0001 | 0.0001 | | 0.0001 |

| Compound | IC$_{50}$ (μM) | | | | | |
|---|---|---|---|---|---|---|
| | P-388 | A-549 | HT-29 | MEL-28 | CV-1 | DU-145 |
| 51 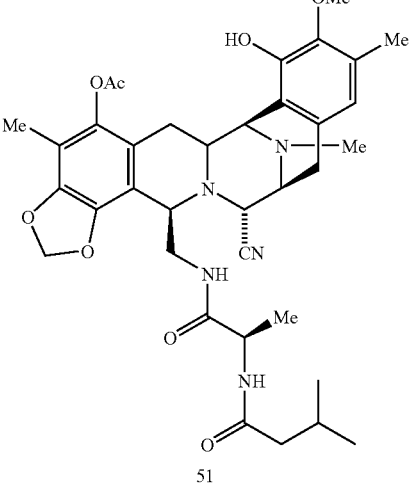 | 0.0001 | 0.0001 | 0.0001 | 0.0001 | | 0.0001 |
| 52 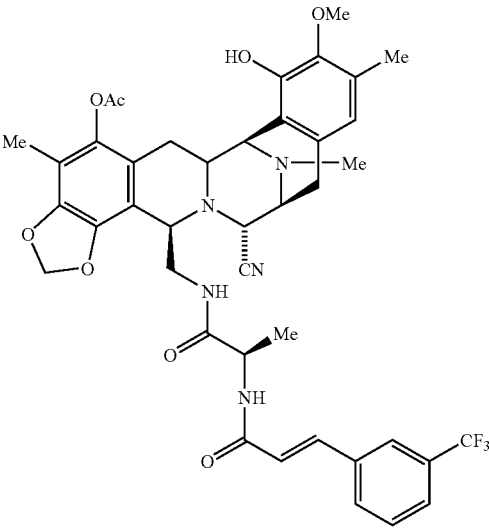 | 0.001 | 0.001 | 0.001 | 0.001 | | 0.001 |
| 53 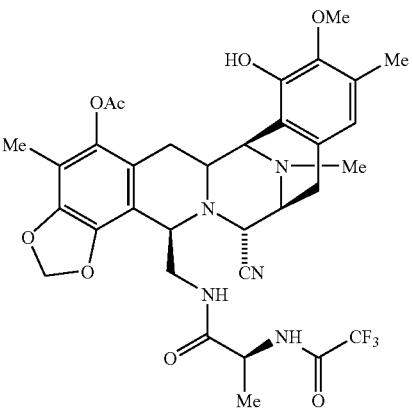 | 0.0001 | 0.0001 | 0.0001 | 0.0001 | | 0.0001 |

-continued
| Compound | IC$_{50}$ (μM) | | | | | |
|---|---|---|---|---|---|---|
| | P-388 | A-549 | HT-29 | MEL-28 | CV-1 | DU-145 |
| 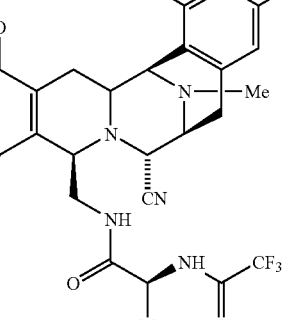 54 | 0.001 | 0.001 | 0.001 | 0.001 | | 0.001 |
| 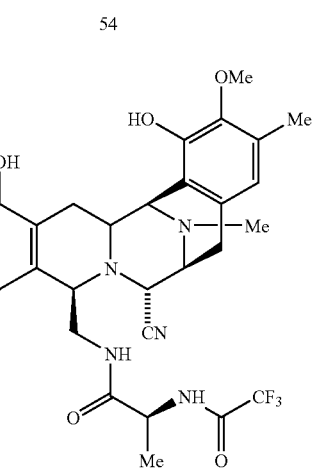 55 | 0.01 | 0.01 | 0.01 | 0.01 | | 0.01 |
| 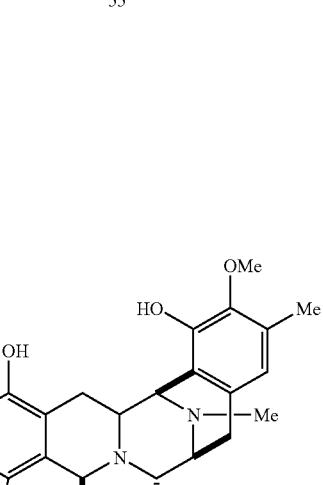 56 | 0.18 | 0.9 | 0.18 | 0.8 | | 0.9 |

-continued

| Compound | IC$_{50}$ (μM) | | | | | |
|---|---|---|---|---|---|---|
| | P-388 | A-549 | HT-29 | MEL-28 | CV-1 | DU-145 |
| 57 | 0.14 | 0.14 | 0.14 | 0.14 | | 0.14 |
| 58 | 0.001 | 0.001 | 0.001 | 0.001 | | 0.001 |
| 60 | 0.001 | 0.001 | 0.0005 | 0.001 | | 0.0005 |

-continued

| Compound | IC$_{50}$ (μM) | | | | | |
|---|---|---|---|---|---|---|
| | P-388 | A-549 | HT-29 | MEL-28 | CV-1 | DU-145 |
| 61 | 0.001 | 0.001 | 0.001 | 0.001 | | 0.001 |
| 62 | 0.001 | 0.001 | 0.0005 | 0.0005 | | 0.001 |
| 63 | 0.0001 | 0.0001 | 0.0001 | 0.0001 | | 0.0001 |

-continued
| Compound | IC$_{50}$ (μM) | | | | | |
|---|---|---|---|---|---|---|
| | P-388 | A-549 | HT-29 | MEL-28 | CV-1 | DU-145 |
| 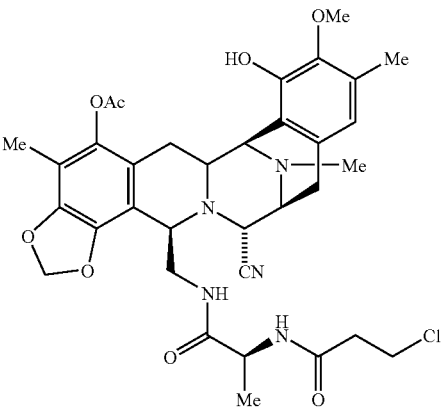 64 | 0.001 | 0.001 | 0.001 | 0.001 | | 0.001 |
| 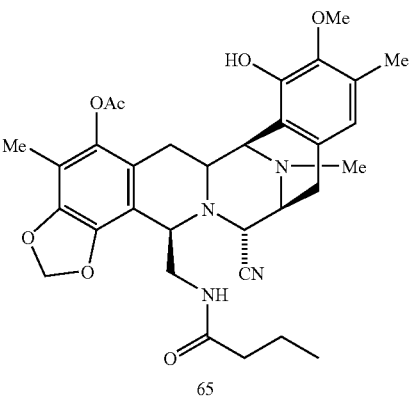 65 | 0.0001 | 0.0005 | 0.0001 | 0.0001 | | 0.0005 |
| 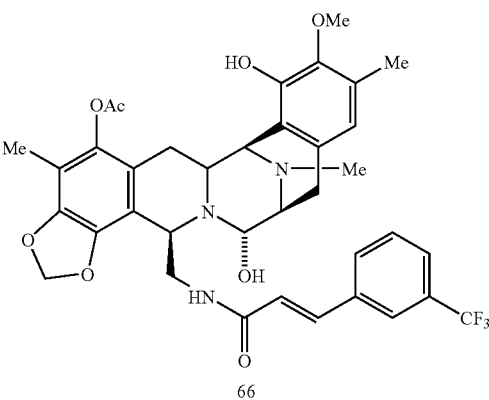 66 | 0.0001 | 0.0001 | 0.0001 | 0.0001 | | 0.0001 |

-continued

| Compound | IC$_{50}$ (μM) | | | | | |
|---|---|---|---|---|---|---|
| | P-388 | A-549 | HT-29 | MEL-28 | CV-1 | DU-145 |
| 67 | 0.0001 | 0.0001 | 0.0001 | 0.0001 | | 0.0001 |

From this activity data and other considerations, it can be seen that the active compounds of this invention include a preferred class of compounds of the general formula (XXIII):

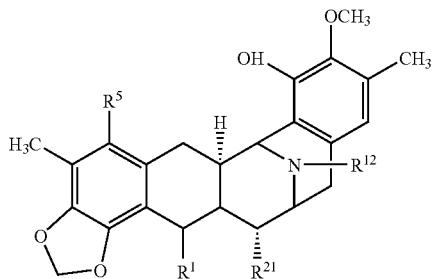

where $R^1$ is as previously defined for formula (XVIIb) and is preferably a derivatised aminomethylene group of moderate bulk;

$R^5$ is as previously defined for formula (XVIIb) and is preferably a derivatised hydroxy group of low bulk;

$R^{12}$ is as previously defined and is preferably —NCH$_3$— and $R^{21}$ is a hydroxy or cyano group.

$R^1$ is suitably a hydrophobic group and which thus lacks free amino, hydroxy or other hydrophilic function. Typically $R^1$ is a group —CH$_2$—NH$_2$—CO—R$^a$, where R$^a$ is as defined but preferably has a linear chain length of less than 20 atoms, more preferably less than 15 or 10 atoms, where a 1,4-phenyl is counted as a chain length of four atoms and similar considerations apply to other cyclic groups (for example, 1,2-cyclohexyl is chain length of two), and the linear chain of less than 10, 15 or 20 atoms can itself be substituted. In particular, the data suggests there is a balance to be achieved between having no such group R$^a$—CO— and having a large, bulky group.

In one variation, we prefer that $R^1$ is free from cyclic groups, especially aromatic groups. In a related variation, the present invention does not prepare the compounds which are described in the article Proc. Natl. Acad. Sci. USA, 96, 3496-3501, 1999, incorporated by reference. Our preferred groups for $R^1$ exclude the corresponding substituents CH$_2$R$_2$ shown in Table 1 of that article, specifically the groups A, B, C and D for R$_2$.

$R^5$ is preferably an acetyl group.

In particularly preferred compounds, the group $R^1$ is acylated on an —NH$_2$ group, and for example N-acyl derivatives can be formed from groups —CH$_2$NH$_2$ and —CH$_2$—NH-aa. The acyl derivatives can be N-acyl or N-thioacyl derivatives thereof. The acyl groups can be of formula —CO—R$^a$, where R$^a$ is as defined and is chosen to meet the indicated criteria. Suitable acyl groups include alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other amino acid acyl groups. Such amino acid acyl groups are preferred derivatised on the amino group to give hydrophobicity.

In a variation, the group $R^1$ is a derivatised hydroxymethylene group. Similar considerations apply as with the derivatised aminomethylene group.

Reflecting the active compounds, an important process in accordance with this invention is as follows:

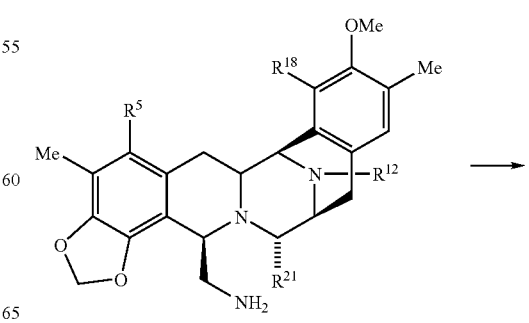

-continued

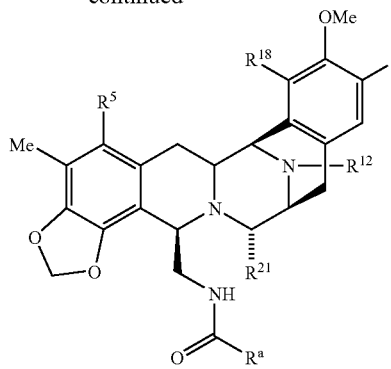

where $R^5$ for the end product is as defined for the compound (XXXII) and may be different in the starting material and converted thereto as part of the process, $R^{18}$ is a hydroxy group in the end product but may be a protected hydroxy group in the starting material and converted thereto as part of the process, $R^{12}$ for the end product may be the same as in the starting material or may be converted thereto as part of the process, $R^{21}$ for the end product is as defined and if a hydroxy group may be formed from a cyano group as part of the process, $R^a$ is as defined, and may be further acylated as part of the process to give an end product with an acylated $R^a$ group as discussed.

$R^5$ is preferably acetyl or other small acyl group in the starting material and is not changed in the reaction. $R^{18}$ is preferably a hydroxy group in the starting material and is not changed in the reaction. $R^{12}$ is preferably —$NCH_3$— in the starting material and is not changed in the reaction. $R^{21}$ the end product is as defined and if a hydroxy group may be formed from a cyano group as part of the process. $R^a$ is in the final product is preferably as defined in relation to the compound of formula (XXIII).

Another important method of this invention includes the reaction:

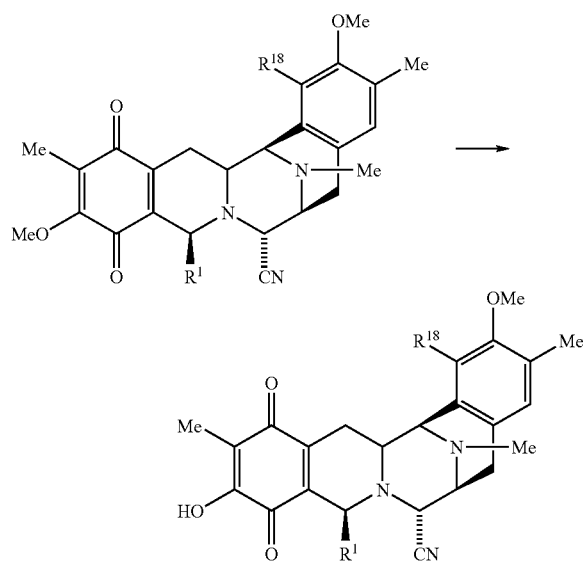

Another important method of this invention includes the reaction:

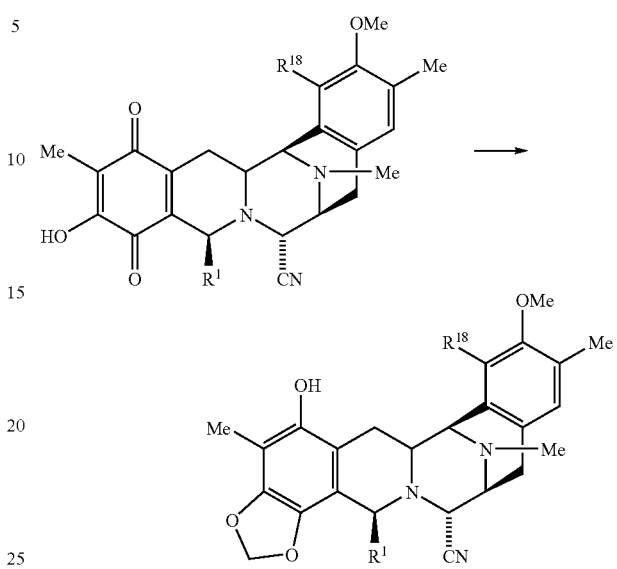

Another important method of this invention includes the reaction includes the reaction where a group $R^1$ is aminomethylene is converted to a hydroxymethylene group.

Another important method of this invention includes the reaction wherein a compound with a group $R^1$ which is hydroxymethylene is reacted with a reagent of the formula (XIX)

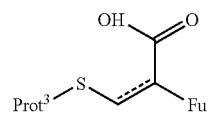

where Fu indicates a protected functional group, $Prot^3$ is a protecting group, and the dotted line shows an optional double bond.

Another important method of this invention includes the reaction for preparing a 21-cyano compound of formula (XVI) which comprises reacting a compound of formula (XV):

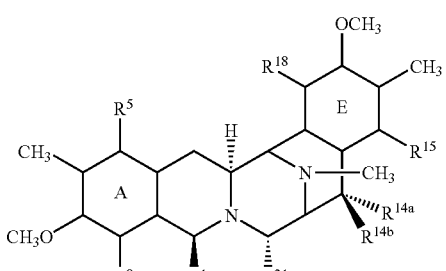

where $R^1$, $R^5$, $R^8$, $R^{14a}$, $R^{14b}$, $R^{15}$ and $R^{18}$ are as defined and $R^{21}$ is a hydroxy group, with a source of cyanide ion, to give the desired 21-cyano compound.

In addition, processes using other nucleophile-containing compounds, to produce similar compounds of formula (XVI) wherein the 21-position is protected by another nucleophilic group, a 21-Nuc group, are also envisaged. For example, a 21-Nuc compound of formula (XVI) with an alkylamino substituent at the 21-position can be produced by reacting the compound of formula (XV) wherein $R^{21}$ is a hydroxy group with a suitable alkylamine. A 21-Nuc compound of formula (XVI) with an alkylthio substituent at the 21-position can also be produced by reacting the compound of formula (XV) wherein $R^{21}$ is a hydroxy group with a suitable alkanethiol. Alternatively, a 21-Nuc compound of formula (XVI) with an α-carbonylalkyl substituent at the 21-position can be produced by reacting the compound of formula (XV) wherein $R^{21}$ is a hydroxy group with a suitable carbonyl compound, typically in the presence of a base. Other synthetic routes are available for other 21-Nuc compounds.

Another important reaction of this invention involves treatment of a 21-cyano product of this invention to form a 21-hydroxy compound. Such compounds have interesting in vivo properties.

EXAMPLES

Example 1

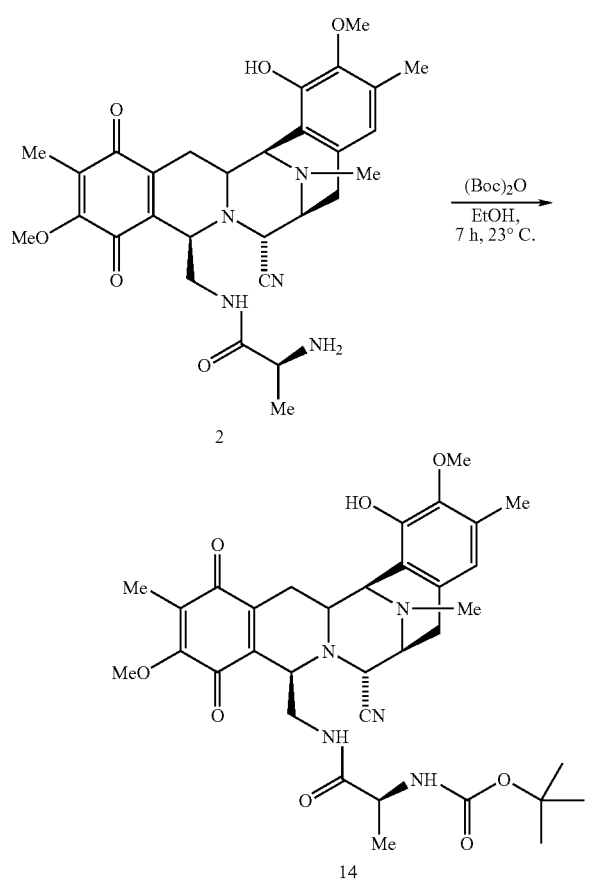

To a solution of 2 (21.53 g, 39.17 ml) in ethanol (200 ml), tert-butoxycarbonyl anhydride (7.7 g, 35.25 ml) was added and the mixture was stirred for 7 h at 23° C. Then, the reaction was concentrated in vacuo and the residue was purified by flash column chromatography ($SiO_2$, hexane:ethyl acetate 6:4) to give 14 (20.6 g, 81%) as a yellow solid.

Rf: 0.52 (ethyl acetate:$CHCl_3$ 5:2).

$^1H$ NMR (300 MHz, $CDCl_3$): δ 6.49 (s, 1H), 6.32 (bs, 1H), 5.26 (bs, 1H), 4.60 (bs, 1H), 4.14 (d, J=2.4 Hz, 1H), 4.05 (d, J=2.4 Hz, 1H), 3.94 (s, 3H), 3.81 (d, J=4.8 Hz, 1H), 3.7 (s, 3H), 3.34 (br d, J=7.2 Hz, 1H), 3.18-3.00 (m, 5H), 2.44 (d, J=18.3 Hz, 1H), 2.29 (s, 3H), 2.24 (s, 3H), 1.82 (s, 3H), 1.80-1.65 (m, 1H), 1.48 (s, 9H), 0.86 (d, J=5.7 Hz, 3H)

$^{13}C$ NMR (75 MHz, $CDCl_3$): δ 185.5, 180.8, 172.7, 155.9, 154.5, 147.3, 143.3, 141.5, 135.3, 130.4, 129.2, 127.5, 120.2, 117.4, 116.9, 80.2, 60.7, 60.3, 58.5, 55.9, 55.8, 54.9, 54.4, 50.0, 41.6, 40.3, 28.0, 25.3, 24.0, 18.1, 15.6, 8.5.

ESI-MS m/z: Calcd. for $C_{34}H_{43}N_5O_8$: 649.7. Found $(M+H)^+$: 650.3.

Example 2

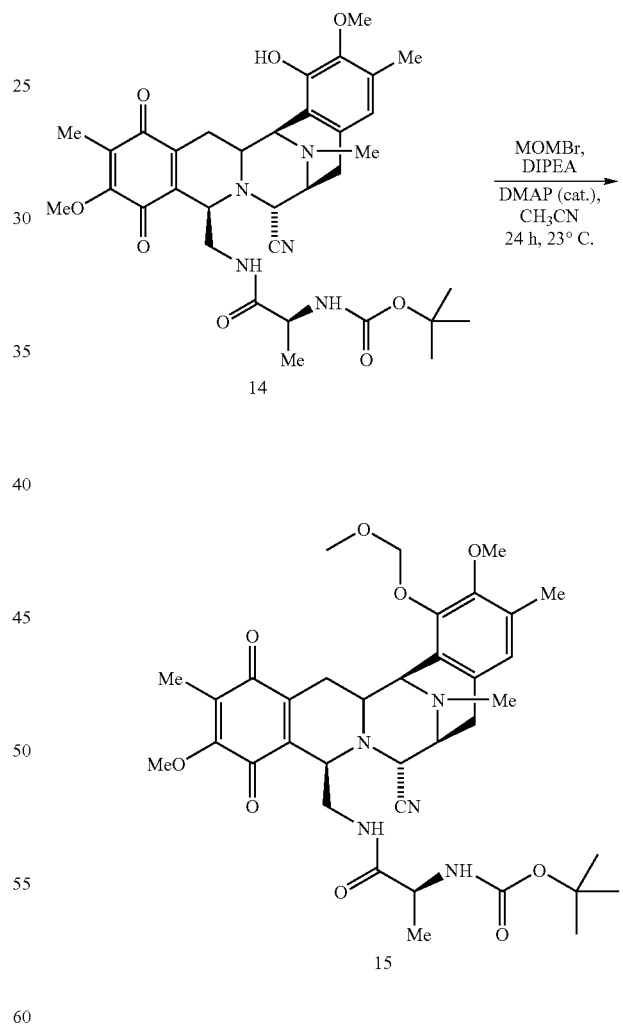

To a stirred solution of 14 (20.6 g, 31.75 ml) in $CH_3CN$ (159 ml), diisopropylethylamine (82.96 ml, 476.2 ml), methoxymethylene bromide (25.9 ml, 317.5 ml) and dimethylaminopyridine (155 mg, 1.27 ml) were added at 0° C. The mixture was stirred at 23° C. for 24 h. The reaction was quenched at 0° C. with aqueous 0.1N HCl (750 ml) (pH=5), and extracted with $CH_2Cl_2$ (2×400 ml). The organic phase was dried (so dium sulphate) and concentrated in vacuo. The residue was purified by flash column chromatography (SiO$_2$, gradient hexane:ethyl acetate 4:1 to hexane:ethyl acetate 3:2) to give 15 (17.6 g, 83%) as a yellow solid.

Rf: 0.38 (hexane:ethyl acetate 3:7).

$^1$H NMR (300 MHz, CDCl$_3$): δ 6.73 (s, 1H), 5.35 (bs, 1H), 5.13 (s, 2H), 4.50 (bs, 1H), 4.25 (d, J=2.7 Hz, 1H), 4.03 (d, J=2.7 Hz, 1H), 3.97 (s, 3H), 3.84 (bs, 1H), 3.82-3.65 (m, 1H), 3.69 (s, 3H), 3.56 (s, 3H), 3.39-3.37 (m, 1H), 3.20-3.00 (m, 5H), 2.46 (d, J=18 Hz, 1H), 2.33 (s, 3H), 2.23 (s, 3H), 1.85 (s, 3H), 1.73-1.63 (m, 1H), 1.29 (s, 9H), 0.93 (d, J=5.1 Hz, 3H)

$^{13}$C NMR (75 MHz, CDCl$_3$): δ 185.4, 180.9, 172.4, 155.9, 154.5, 149.0, 148.4, 141.6, 135.1, 131.0, 129.9, 127.6, 124.4, 123.7, 117.3, 99.1, 79.3, 60.7, 59.7, 58.4, 57.5, 56.2, 55.9, 55.0, 54.2, 50.0, 41.5, 39.9, 28.0, 25.2, 24.0, 18.1, 15.6, 8.5.

ESI-MS m/z: Calcd. for C$_{36}$H$_{47}$N$_5$O$_9$: 693.8. Found (M+H)$^+$: 694.3.

Example 3

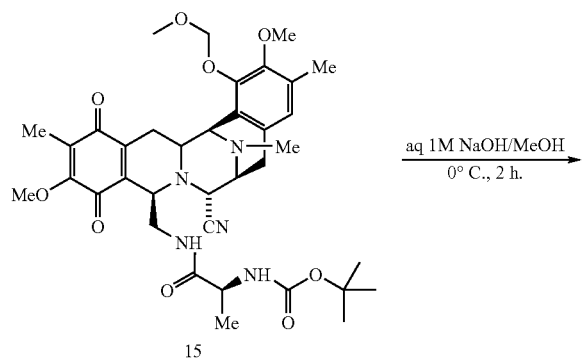

15

To a flask containing 15 (8 g, 1.5 ml) in methanol (1.6 l) an aqueous solution of 1M sodium hydroxide (3.2 l) was added at 0° C. The reaction was stirred for 2 h at this temperature and then, quenched with 6M HCl to pH=5. The mixture was extracted with ethyl acetate (3×1 l) and the combined organic layers were dried over sodium sulphate and concentrated in vacuo. The residue was purified by flash column chromatography (SiO$_2$, gradient CHCl$_3$ to CHCl$_3$:ethyl acetate 2:1) to afford 16 (5.3 mg, 68%).

Rf: 0.48 (CH$_3$CN:H$_2$O 7:3, RP-C18)

$^1$H NMR (300 MHz, CDCl$_3$): δ 6.73 (s, 1H), 5.43 (bs, 1H), 5.16 (s, 2H), 4.54 (bs, 1H), 4.26 (d, J=1.8 Hz, 1H), 4.04 (d, J=2.7 Hz 1H), 3.84 (bs, 1H), 3.80-3.64 (m, 1H), 3.58 (s, 3H), 3.41-3.39 (m, 1H), 3.22-3.06 (m, 5H), 2.49 (d, J=18.6 Hz 1H), 2.35 (s, 3H), 2.30-2.25 (m, 1H), 2.24 (s, 3H), 1.87 (s, 3H), 1.45-1.33 (m, 1H), 1.19 (s, 9H), 1.00 (br d, J=6.6 Hz 3H)

$^{13}$C NMR (75 MHz, CDCl$_3$): δ 184.9, 180.9, 172.6, 154.7, 151.3, 149.1, 148.6, 144.7, 132.9, 131.3, 129.8, 124.5, 123.7, 117.3, 116.8, 99.1, 79.4, 59.8, 58.6, 57.7, 56.2, 55.6, 54.9, 54.5, 50.1, 41.6, 40.1, 28.0, 25.3, 24.4, 18.1, 15.7, 8.0.

ESI-MS m/z: Calcd. for C$_{35}$H$_{45}$N$_5$O$_9$: 679.7. Found (M+H)$^+$: 680.3.

Example 4

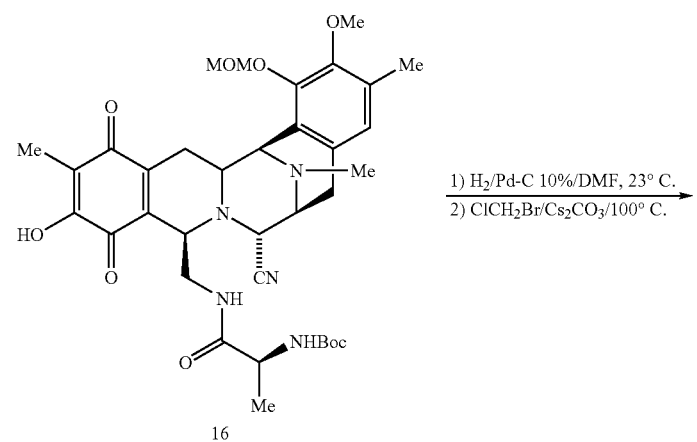

16

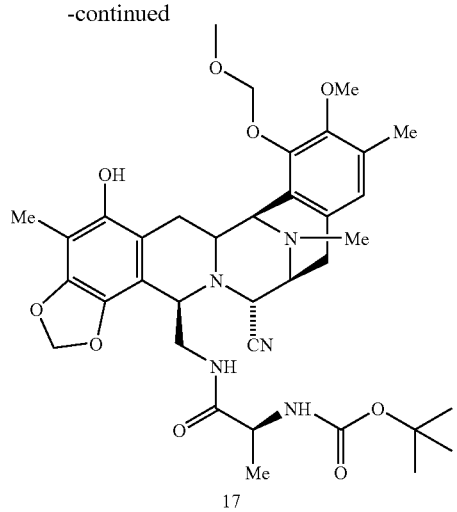

17

To a degassed solution of compound 16 (1.8 g, 2.64 ml) in DMF (221 ml) 10% Pd/C (360 mg) was added and stirred under H$_2$ (atmospheric pressure) for 45 min. The reaction was filtered through celite under argon, to a flask containing anhydrous Cs$_2$CO$_3$ (2.58 g, 7.92 ml). Then, bromochloromethane (3.40 ml 52.8 ml), was added and the tube was sealed and stirred at 100° C. for 2 h. The reaction was cooled, filtered through a pad of celite and washed with CH$_2$Cl$_2$. The organic layer was concentrated and dried (sodium sulphate) to afford 17 as a brown oil that was used in the next step with no further purification.

Rf: 0.36 (hexane:ethyl acetate 1:5, SiO$_2$).

$^1$H NMR (300 MHz, CDCl$_3$): δ 6.68 (s, 1H), 6.05 (bs, 1H), 5.90 (s, 1H), 5.79 (s, 1H), 5.40 (bs, 1H), 5.31-5.24 (m, 2H), 4.67 (d, J=8.1 Hz, 1H), 4.19 (d, J=2.7 Hz, 1H), 4.07 (bs, 1H), 4.01 (bs, 1H), 3.70 (s, 3H), 3.67 (s, 3H), 3.64-2.96 (m, 5H), 2.65 (d, J=18.3 Hz, 1H), 2.33 (s, 3H), 2.21 (s, 3H), 2.04 (s, 3H), 2.01-1.95 (m, 1H), 1.28 (s, 9H), 0.87 (d, J=6.3 Hz, 3H)

$^{13}$C NMR (75 MHz, CDCl$_3$): δ 172.1, 162.6, 154.9, 149.1, 145.7, 135.9, 130.8, 130.7, 125.1, 123.1, 117.8, 100.8, 99.8, 76.6, 59.8, 59.2, 57.7, 57.0, 56.7, 55.8, 55.2, 49.5, 41.6, 40.1, 36.5, 31.9, 31.6, 29.7, 28.2, 26.3, 25.0, 22.6, 18.2, 15.8, 14.1, 8.8.

ESI-MS m/z: Calcd. for C$_{36}$H$_{47}$N$_5$O$_9$: 693.34. Found (M+H)$^+$: 694.3.

Example 5

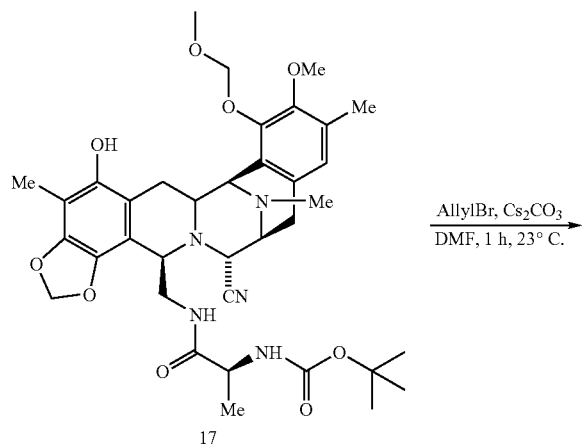

17

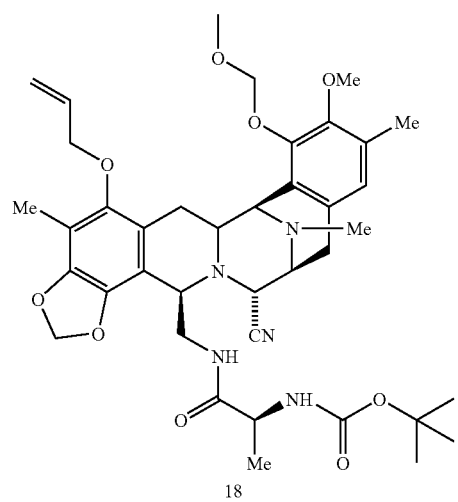

18

To a flask containing a solution of 17 (1.83 g, 2.65 ml) in DMF (13 ml), Cs$_2$CO$_3$ (2.6 g, 7.97 ml), and allyl bromide (1.15 ml, 13.28 ml) were added at 0° C. The resulting mixture was stirred at 23° C. for 1 h. The reaction was filtered through a pad of celite and washed with CH$_2$Cl$_2$. The organic layer was dried and concentrated (sodium sulphate). The residue was purified by flash column chromatography (SiO$_2$, CHCl$_3$: ethyl acetate 1:4) to afford 18 (1.08 mg, 56%) as a white solid.

Rf: 0.36 (CHCl$_3$:ethyl acetate 1:3).

$^1$H NMR (300 MHz, CDCl$_3$): δ 6.70 (s, 1H), 6.27-6.02 (m, 1H), 5.94 (s, 1H), 5.83 (s, 1H), 5.37 (dd, J$_1$=1.01 Hz, J$_2$=16.8 Hz, 1H), 5.40 (bs, 1H), 5.25 (dd, J$_1$=1.0 Hz, J$_2$=10.5 Hz, 1H), 5.10 (s, 2H), 4.91 (bs, 1H), 4.25-4.22 (m, 1H), 4.21 (d, J=2.4 Hz, 1H), 4.14-4.10 (m, 1H), 4.08 (d, J=2.4 Hz, 1H), 4.00 (bs, 1H), 3.70 (s, 3H), 3.59 (s, 3H), 3.56-3.35 (m, 2H), 3.26-3.20 (m, 2H), 3.05-2.96 (dd, J$_1$=8.1 Hz, J$_2$=18 Hz, 1H), 2.63 (d, J=18 Hz, 1H), 2.30 (s, 3H), 2.21 (s, 3H), 2.09 (s, 3H), 1.91-1.80 (m, 1H), 1.24 (s, 9H), 0.94 (d, J=6.6 Hz, 3H)

$^{13}$C NMR (75 MHz, CDCl$_3$): δ 172.0, 154.8, 148.8, 148.6, 148.4, 144.4, 138.8, 133.7, 130.9, 130.3, 125.1, 124.0, 120.9, 117.8, 117.4, 112.8, 112.6, 101.1, 99.2, 73.9, 59.7, 59.3, 57.7, 56.9, 56.8, 56.2, 55.2, 40.1, 34.6, 31.5, 28.1, 26.4, 25.1, 22.6, 18.5, 15.7, 14.0, 9.2.

ESI-MS m/z: Calcd. for $C_{39}H_5N_5O_9$: 733.4. Found (M+H)$^+$: 734.4.

Example 6

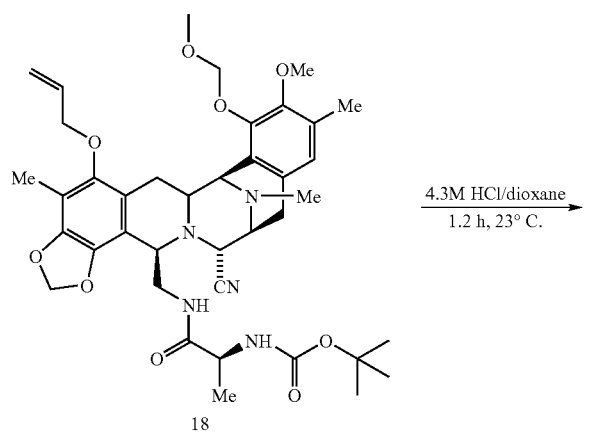

To a solution of 18 (0.1 g, 0.137 ml) in dioxane (2 ml), 4.2M HCl/dioxane (1.46 ml) was added and the mixture was stirred for 1.2 h at 23° C. The reaction was quenched at 0° C. with sat. Aqueous sodium bicarbonate (60 ml) and extracted with ethyl acetate (2×70 ml). The organic layers were dried (sodium sulphate) and concentrated in vacuo to afford 19 (267 mg, 95%) as a white solid that was used in subsequent reactions with no further purification.

Rf: 0.17 (ethyl acetate:methanol 10:1, SiO$_2$)

$^1$H NMR (300 MHz, CDCl$_3$): δ 6.49 (s, 1H), 6.12-6.00 (m, 1H), 5.94 (s, 1H), 5.86 (s, 1H), 5.34 (dd, J=1.0 Hz, J=17.4 Hz, 1H), 5.25 (dd, J=1.0 Hz, J=10.2 Hz, 1H), 4.18-3.76 (m, 5H), 3.74 (s, 3H), 3.71-3.59 (m, 1H), 3.36-3.20 (m, 4H), 3.01-2.90 (m, 1H), 2.60 (d, J=18.0 Hz, 1H), 2.29 (s, 3H), 2.24 (s, 3H), 2.11 (s, 3H), 1.97-1.86 (m, 1H), 0.93 (d, J=8.7 Hz, 3H)

$^{13}$C NMR (75 MHz, CDCl$_3$): δ 175.5, 148.4, 146.7, 144.4, 142.4, 138.9, 133.7, 131.3, 128.3, 120.8, 117.9, 117.4, 113.8, 112.4, 101.1, 74.2, 60.5, 59.1, 56.5, 56.1, 56.3, 56.0, 55.0, 50.5, 41.6, 39.5, 29.5, 26.4, 24.9, 21.1, 15.5, 9.33.

ESI-MS m/z: Calcd. for $C_{32}H_{39}N_5O_6$: 589. Found (M+H)$^+$: 590.

Example 7

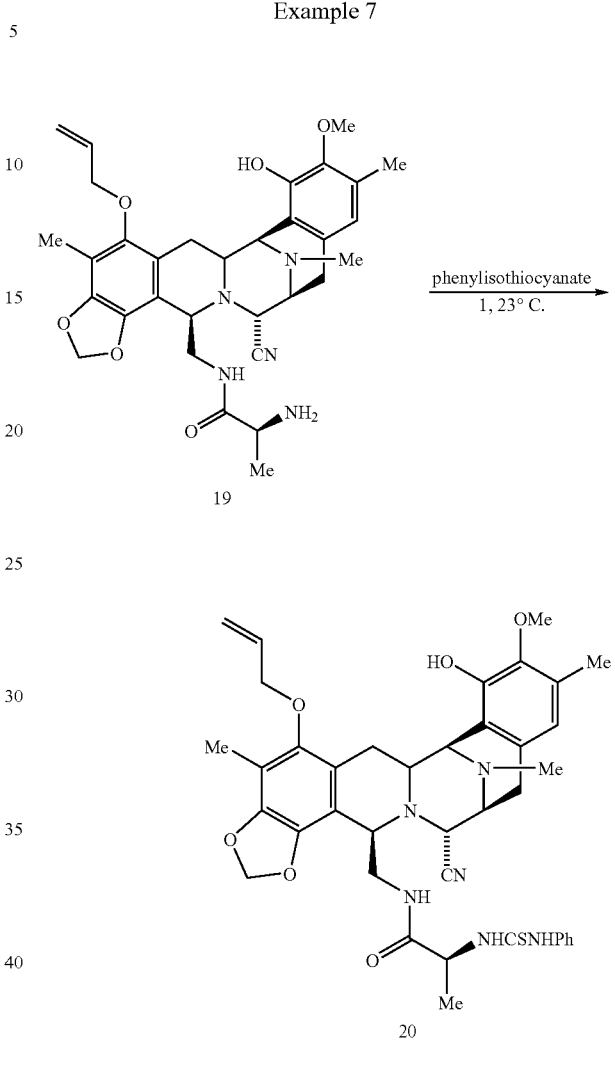

To a solution of 19 (250 mg, 0.42 ml) in CH$_2$Cl$_2$ (1.5 ml), phenyl isothiocyanate (0.3 ml, 2.51 ml) was added and the mixture was stirred at 23° C. for 1 h. The reaction was concentrated in vacuo and the residue was purified by flash column chromatography (SiO$_2$, gradient Hexane to 5:1 hexane: ethyl acetate) to afford 20 (270 mg, 87%) as a white solid.

Rf: 0.56 (CHCl$_3$:ethyl acetate 1:4).

$^1$H NMR (300 MHz, CDCl$_3$): δ 8.00 (bs, 1H), 7.45-6.97 (m, 4H), 6.10 (s, 1H), 6.08-6.00 (m, 1H), 5.92 (s, 1H), 5.89 (s, 1H), 5.82 (s, 1H), 5.40 (dd, J=1.5 Hz, J=17.1 Hz, 1H), 3.38 (bs, 1H), 5.23 (dd, J=1.5 Hz, J=10.5 Hz, 1H), 4.42-4.36 (m, 1H), 4.19-4.03 (m, 5H), 3.71 (s, 3H), 3.68-3.17 (m, 4H), 2.90 (dd, J=7.8 Hz, J=18.3 Hz, 1H), 2.57 (d, J=18.3 Hz, 1H), 2.25 (s, 3H), 2.12 (s, 3H), 2.10 (s, 3H), 1.90 (dd, J=12.3 Hz, J=16.5 Hz, 1H), 0.81 (d, J=6.9 Hz, 3H).

$^{13}$C NMR (75 MHz, CDCl$_3$): δ 178.4, 171.6, 148.6, 146.8, 144.3, 142.7, 138.7, 136.2, 133.6, 130.7, 129.8, 126.6, 124.2, 124.1, 120.9, 120.5, 117.7, 117.4, 116.7, 112.6, 112.5, 101.0, 74.0, 60.6, 59.0, 57.0, 56.2, 56.1, 55.0, 53.3, 41.4, 39.7, 26.3, 24.8, 18.3, 15.5, 9.2.

ESI-MS m/z: Calcd. for $C_{39}H_{44}N_6O_6S$: 724.8 Found (M+H)$^+$: 725.3.

ESI-MS m/z: Calcd. for $C_{29}H_{34}N_4O_5$: 518.3. Found (M+H)$^+$: 519.2.

Example 8

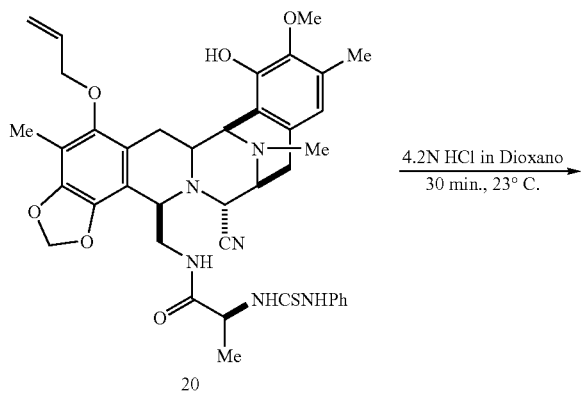

Example 9

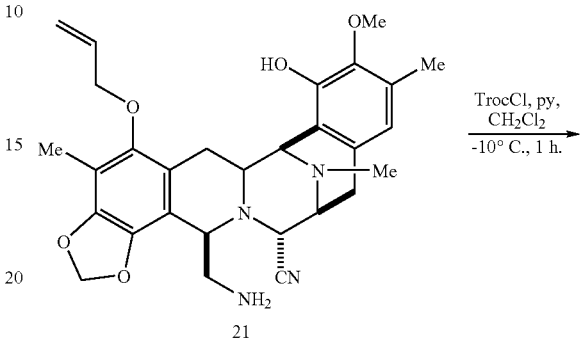

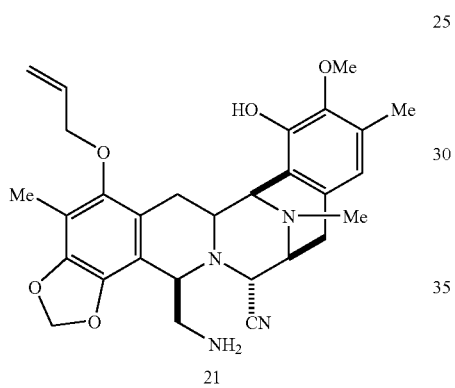

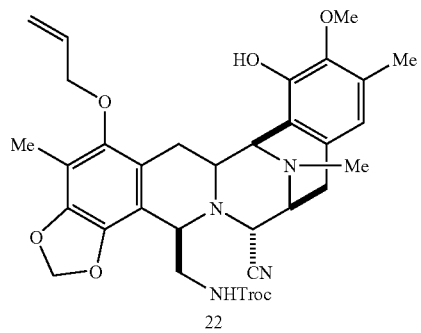

To a solution of 20 (270 mg, 0.37 ml) in dioxane (1 ml), 4.2N HCl/dioxane (3.5 ml) was added and the reaction was stirred at 23° C. for 30 min. Then, ethyl acetate (20 ml) and H$_2$O (20 ml) were added and the organic layer was decanted. The aqueous phase was basified with saturated aqueous sodium bicarbonate (60 ml) (pH=8) at 0° C. and then, extracted with CH$_2$Cl$_2$ (2×50 ml). The combined organic extracts were dried (sodium sulphate), and concentrated in vacuo. The residue was purified by flash column chromatography (SiO$_2$, ethyl acetate:methanol 5:1) to afford compound 21 (158 mg, 82%) as a white solid.

Rf: 0.3 (ethyl acetate:methanol 1:1).

$^1$H NMR (300 MHz, CDCl$_3$): δ 6.45 (s, 1H), 6.12-6.03 (m, 1H), 5.91 (s, 1H), 5.85 (s, 1H), 5.38 (dd, J$_1$=1.2 Hz, J$_2$=17.1 Hz, 1H), 5.24 (dd, J$_1$=1.2 Hz, J$_2$=10.5 Hz, 1H), 4.23-4.09 (m, 4H), 3.98 (d, J=2.1 Hz, 1H), 3.90 (bs, 1H), 3.72 (s, 3H), 3.36-3.02 (m, 5H), 2.72-2.71 (m, 2H), 2.48 (d, J=18.0 Hz, 1H), 2.33 (s, 3H), 2.22 (s, 3H), 2.11 (s, 3H), 1.85 (dd, J$_1$=11.7 Hz, J$_2$=15.6 Hz, 1H)).

$^{13}$C NMR (75 MHz, CDCl$_3$): δ 148.4, 146.7, 144.4, 142.8, 138.8, 133.8, 130.5, 128.8, 121.5, 120.8, 118.0, 117.5, 116.9, 113.6, 112.2, 101.1, 74.3, 60.7, 59.9, 58.8, 56.6, 56.5, 55.3, 44.2, 41.8, 29.7, 26.5, 25.7, 15.7, 9.4.

To a solution of 21 (0.64 g, 1.22 ml) in CH$_2$Cl$_2$ (6.13 ml), pyridine (0.104 ml, 1.28 ml) and 2,2,2-trichloroethyl chloroformate (0.177 ml, 1.28 ml) were added at −10° C. The mixture was stirred at this temperature for 1 h and then, the reaction was quenched by addition of 0.1N HCl (10 ml) and extracted with CH$_2$Cl$_2$ (2×10 ml). The organic layer was dried over sodium sulphate and concentrated in vacuo. The residue was purified by flash column chromatography (SiO$_2$, (hexane:ethyl acetate 1:2) to afford 22 (0.84 g, 98%) as a white foam solid.

Rf: 0.57 (ethyl acetate:methanol 5:1).

$^1$H NMR (300 MHz, CDCl$_3$): δ 6.50 (s, 1H), 6.10-6.00 (m, 1H), 6.94 (d, J=1.5 Hz, 1H), 5.87 (d, J=1.5 Hz, 1H), 5.73 (bs, 1H), 5.37 (dq, J$_1$=1.5 Hz, J$_2$=17.1 Hz, 1H), 5.26 (dq, J$_1$=1.8 Hz, J$_2$=10.2 Hz, 1H), 4.60 (d, J=12 Hz, 1H), 4.22-4.10 (m, 4H), 4.19 (d, J=12 Hz, 1H), 4.02 (m, 2H), 3.75 (s, 3H), 3.37-3.18 (m, 5H), 3.04 (dd, J$_1$=8.1 Hz, J$_2$=18 Hz, 1H), 2.63 (d, J=18 Hz, 1H), 2.31 (s, 3H), 2.26 (s, 3H), 2.11 (s, 3H), 1.85 (dd, J$_1$=12.3 Hz, J$_2$=15.9 Hz, 1H).

$^{13}$C NMR (75 MHz, CDCl$_3$) δ 154.3, 148.5, 146.7, 144.5, 142.8, 139.0, 133.8, 130.7, 128.7, 121.3, 120.8, 117.8, 117.7, 116.8, 112.7, 101.2, 77.2, 74.3, 60.7, 59.9, 57.0, 56.4, 55.3, 43.3, 41.7, 31.6, 26.4, 25.3, 22.6, 15.9, 14.1, 9.4.

ESI-MS m/z: Calcd. for $C_{32}H_{35}Cl_3N_4O_7$: 694.17. Found (M+H)$^+$: 695.2.

ESI-MS m/z: Calcd. for $C_{34}H_{39}Cl_3N_4O_8$: 738.20. Found (M+H)$^+$: 739.0.

Example 10

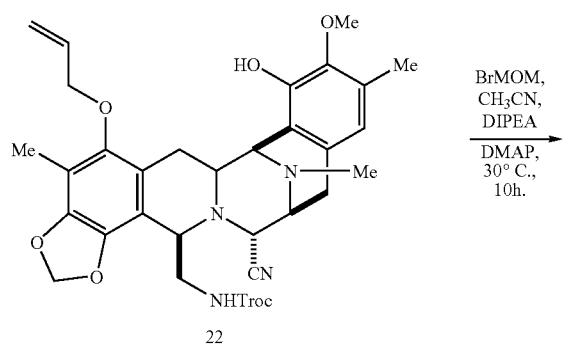

22

BrMOM, CH$_3$CN, DIPEA
DMAP,
30° C.,
10h.
→

Example 11

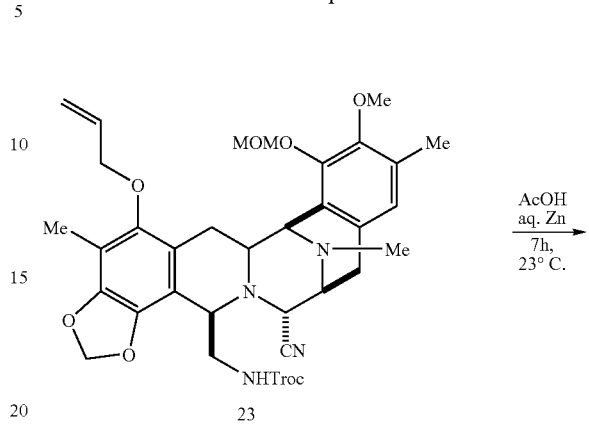

23

AcOH aq. Zn
7h,
23° C.
→

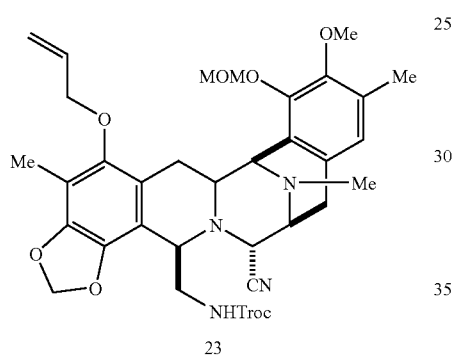

23

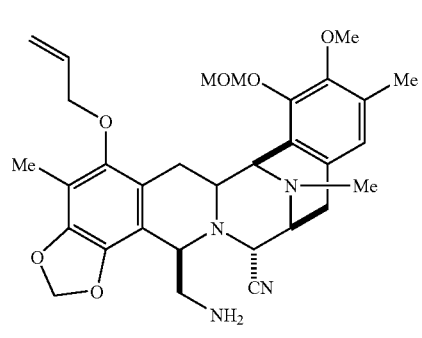

24

To a solution of 22 (0.32 g, 0.46 ml) in CH$_3$CN (2.33 ml), diisopropylethylamine (1.62 ml, 9.34 ml), bromomethyl methyl ether (0.57 ml, 7.0 ml) and dimethylaminopyridine (6 mg, 0.046 ml) were added at 0° C. The mixture was heated at 30° C. for 10 h. Then, the reaction was diluted with dichloromethane (30 ml) and poured in an aqueous solution of HCl at pH=5 (10 ml). The organic layer was dried over sodium sulphate and the solvent was eliminated under reduced pressure to give a residue which was purified by flash column chromatography (SiO$_2$, hexane:ethyl acetate 2:1) to afford 23 (0.304 g, 88%) as a white foam solid.

Rf: 0.62 (hexane:ethyl acetate 1:3).

$^1$H NMR (300 MHz, CDCl$_3$): δ 6.73 (s, 1H), 6.10 (m, 1H), 5.94 (d, J=1.5 Hz, 1H), 5.88 (d, J=1.5 Hz, 1H), 5.39 (dq, $J_1$=1.5 Hz, $J_2$=17.1 Hz, 1H), 5.26 (dq, $J_1$=1.8 Hz, $J_2$=10.2 Hz, 1H), 5.12 (s, 2H), 4.61 (d, J=12 Hz, 1H), 4.55 (t, J=6.6 Hz, 1H), 4.25 (d, J=12 Hz, 1H), 4.22-4.11 (m, 4H), 4.03 (m, 2H), 3.72 (s, 3H), 3.58 (s, 3H), 3.38-3.21 (m, 5H), 3.05 (dd, $J_1$=8.1 Hz, $J_2$=18 Hz, 1H), 2.65 (d, J=18 Hz, 1H), 2.32 (s, 3H), 2.23 (s, 3H), 2.12 (s, 3H), 1.79 (dd, $J_1$=12.3 Hz, $J_2$=15.9 Hz, 1H);

$^{13}$C NMR (75 MHz, CDCl$_3$) δ 154.3, 148.6, 148.4, 144.5, 139.0, 133.6, 130.6, 130.1, 125.07, 124.7, 124.0, 121.1, 117.7, 112.6, 101.2, 99.2, 77.2, 74.4, 74.1, 59.9, 59.8, 57.7, 57.0, 56.8, 56.68, 55.3, 43.2, 41.5, 26.4, 25.2, 15.9, 9.3.

To a suspension of 23 (0.304 g, 0.41 ml) in 90% aqueous acetic acid (4 ml), powder zinc (0.2 g, 6.17 ml) was added and the reaction was stirred for 7 hour at 23° C. The mixture was filtered through a pad of celite which was washed with CH$_2$Cl$_2$. The organic layer was washed with an aqueous sat. solution of sodium bicarbonate (pH=9) (15 ml) and dried over sodium sulphate. The solvent was eliminated under reduced pressure to give 24 (0.191 g, 83%) as a white solid.

Rf: 0.3 (ethyl acetate:methanol 5:1).

$^1$H NMR (300 MHz, CDCl$_3$): δ 6.68 (s, 1H), 6.09 (m, 1H), 5.90 (d, J=1.5 Hz, 1H), 5.83 (d, J=1.5 Hz, 1H), 5.39 (dq, $J_1$=1.5 Hz, $J_2$=17.1 Hz, 1H), 5.25 (dq, $J_1$=1.5 Hz, $J_2$=10.2 Hz, 1H), 5.10 (s, 2H), 4.22-4.09 (m, 3H), 3.98 (d, J=2.4 Hz, 1H), 3.89 (m, 1H), 3.69 (s, 3H), 3.57 (s, 3H), 3.37-3.17 (m, 3H), 3.07 (dd, $J_1$=8.1 Hz, $J_2$=18 Hz, 1H), 2.71 (m, 2H), 2.48 (d, J=18 Hz, 1H), 2.33 (s, 3H), 2.19 (s, 3H), 2.17 (s, 3H), 1.80 (dd, $J_1$=12.3 Hz, $J_2$=15.9 Hz, 1H)

$^{13}$C NMR (75 MHz, CDCl$_3$): δ 148.5, 148.2, 144.3, 138.7, 133.7, 130.7, 129.9, 125.0, 123.9, 121.3, 117.9, 117.5, 113.6, 112.0, 101.0, 99.2, 74.0, 59.8, 59.7, 58.8, 57.6, 57.0, 56.2, 55.2, 44.2, 41.5, 31.5, 26.4, 25.6, 22.5, 16.7, 14.0, 9.2.

ESI-MS m/z: Calcd. for $C_{31}H_{38}N_4O_6$: 562.66. Found $(M+H)^+$: 563.1.

Example 12

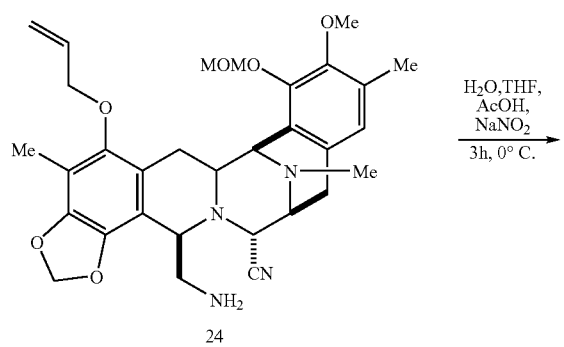

24

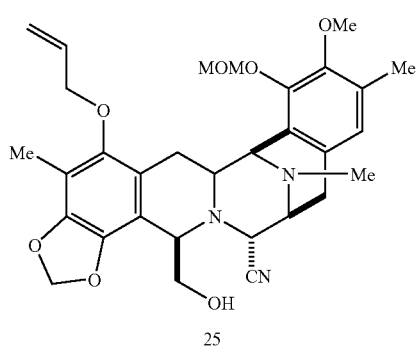

25

To a solution of 24 (20 mg, 0.035 ml), in $H_2O$ (0.7 ml) and THF (0.7 ml), $NaNO_2$ (12 mg, 0.17 ml) and 90% aqueous AcOH (0.06 ml) were added at 0° C. and the mixture was stirred at 0° C. for 3 h. After dilution with $CH_2Cl_2$ (5 ml), the organic layer was washed with water (1 ml), dried over sodium sulphate and concentrated in vacuo. The residue was purified by flash column chromatography ($SiO_2$, hexane: ethyl acetate 2:1) to afford 25 (9.8 mg, 50%) as a white solid.

Rf: 0.34 (hexane:ethyl acetate 1:1).

$^1$H NMR (300 MHz, $CDCl_3$): δ 6.71 (s, 1H), 6.11 (m, 1H), 5.92 (d, J=1.5 Hz, 1H), 5.87 (d, J=1.5 Hz, 1H), 5.42 (dq, $J_1$=1.5 Hz, $J_2$=17.1 Hz, 1H), 5.28 (dq, $J_1$=1.5 Hz, $J_2$=10.2 Hz, 1H), 5.12 (s, 2H), 4.26-4.09 (m, 3H), 4.05 (d, J=2.4 Hz, 1H), 3.97 (t, J=3.0 Hz, 1H), 3.70 (s, 3H), 3.67-3.32 (m, 4H), 3.58 (s, 3H), 3.24 (dd, $J_1$=2.7 Hz, $J_2$=15.9 Hz, 1H), 3.12 (dd, $J_1$=8.1 Hz, $J_2$=18.0 Hz, 1H), 2.51 (d, J=18 Hz, 1H), 2.36 (s, 3H), 2.21 (s, 3H), 2.12 (s, 3H), 1.83 (dd, $J_1$=12.3 Hz, $J_2$=15.9 Hz, 1H)

$^{13}$C NMR (75 MHz, $CDCl_3$) δ 148.7, 148.4, 138.9, 133.7, 131.1, 129.4, 125.1, 123.9, 120.7, 117.6, 117.5, 113.2, 112.3, 101.1, 99.2, 74.0, 63.2, 59.8, 59.7, 57.9, 57.7, 57.0, 56.5, 55.2, 41.6, 29.6, 26.1, 25.6, 22.6, 15.7, 9.2.

ESI-MS m/z: Calcd. for $C_{31}H_{37}N_3O_7$: 563.64. Found $(M+H)^+$: 564.1.

Example 13

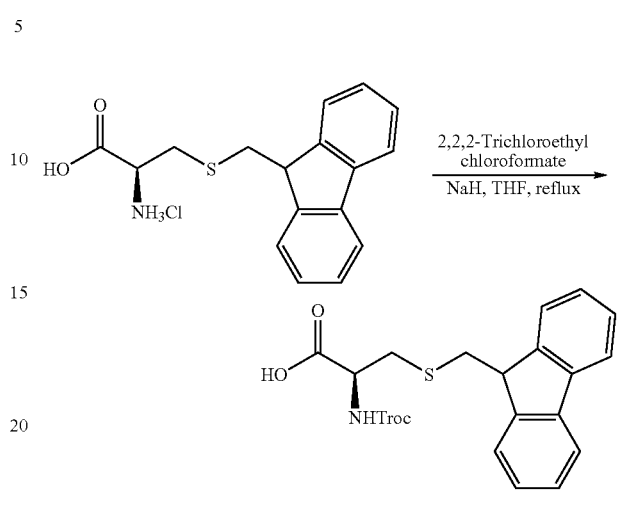

29

The starting material (2.0 g, 5.90 ml) was added to a suspension of sodium hydride (354 mg, 8.86 ml) in THF (40 ml) at 23° C., following the suspension was treated with allyl chloroformate (1.135 ml, 8.25 ml) at 23° C. and then refluxed for 3 hours. The suspension was cooled, filtered off, the solid washed with ethyl acetate (100 ml), and the filtrate was concentrated. The oil crude was ground with hexane (100 ml) and kept at 4° C. overnight. After, the solvent was decanted and the light yellow slurry was treated with $CH_2Cl_2$ (20 ml), and precipitated with hexane (100 ml). After 10 minutes, the solvent was decanted again. The operation was repeated until appearing a white solid. The white solid was filtered off and dried to afford compound 29 (1.80 g, 65%) as a white solid.

$^1$H-NMR (300 MHz, $CDCl_3$): δ 7.74 (d, J=7.5 Hz, 2H), 7.62 (d, J=6.9 Hz, 2H), 7.33 (t, J=7.5 Hz, 2H), 7.30 (t, J=6.3 Hz, 2H), 5.71 (d, J=7.8 Hz, 1H), 4.73 (d, J=7.8 Hz, 2H), 4.59 (m, 1H), 4.11 (t, J=6.0 Hz, 1H), 3.17 (dd, J=6.0 Hz, J=2.7 Hz, 2H), 3.20 (dd, J=5.4 Hz, J=2.1 Hz, 2H).

$^{13}$C-NMR (75 MHz, $CDCl_3$): δ 173.6, 152.7, 144.0, 139.7, 137.8, 126.0, 125.6, 123.4, 118.3, 73.4, 52.4, 45.5, 35.8, 33.7.

ESI-MS m/z: Calcd. for $C_{20}H_{18}Cl_3NO_4S$: 474.8. Found $(M+Na)^+$: 497.8

Example 14

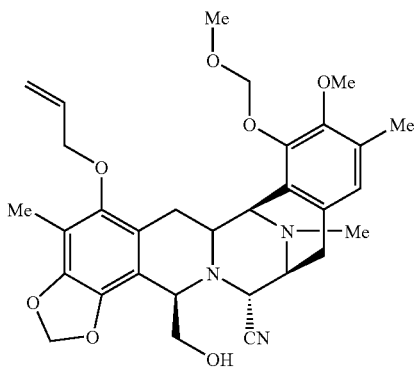

A mixture of compound 25 (585 mg, 1.03 ml) and compound 29 (1.47 mg, 3.11 ml) were azeotroped with anhydrous toluene (3×10 ml). To a solution of 25 and 29 in anhydrous $CH_2Cl_2$ (40 ml) was added DMAP (633 mg, 5.18 ml) and EDC-HCl (994 mg, 5.18 ml) at 23° C. The reaction mixture was stirred at 23° C. for 3 hours. The mixture was partitioned with saturated aqueous solution of sodium bicarbonate (50 ml) and the layers were separated. The aqueous layer was washed with $CH_2Cl_2$ (50 ml). The combined organic layers were dried over sodium sulphate, filtered and concentrated. The crude was purified by flash column chromatography (ethyl acetate/hexane 1:3) to obtain 30 (1.00 g, 95%) as a pale cream yellow solid.

$^1$H-NMR (300 MHz, $CDCl_3$): δ 7.72 (m, 2H), 7.52 (m, 2H), 7.38 (m, 2H), 7.28 (m, 2H), 6.65 (s, 1H), 6.03 (m, 1H), 5.92 (d, J=1.5 Hz, 1H), 5.79 (d, J=1.5 Hz, 1H), 5.39 (m, 1H), 5.29 (dq, J=10.3 Hz, J=1.5 Hz, 1H), 5.10 (s, 2H), 4.73 (d, J=11.9 Hz, 1H), 4.66 (d, J=11.9 Hz, 1H), 4.53 (m, 1H), 4.36-3.96 (m, 9H), 3.89 (t, J=6.4 Hz, 1H), 3.71 (s, 3H), 3.55 (s, 3H), 3.33 (m, 1H), 3.20 (m, 2H), 2.94 (m, 3H), 2.59 (m, 1H), 2.29 (s, 3H), 2.23 (s, 3H), 2.02 (s, 3H), 1.83 (dd, J=16.0 Hz, J=11.9 Hz, 1H).

$^{13}$C-NMR (75 MHz, $CDCl_3$): δ 169.7, 154.0, 148.8, 148.4, 145.7, 144.5, 140.9, 139.0, 133.7, 130.9, 130.6, 127.6, 127.0, 124.8, 124.6, 124.1, 120.8, 119.9, 118.2, 117.7, 117.3, 112.7, 112.1, 101.3, 99.2, 74.7, 73.9, 64.4, 59.8, 57.7, 57.0, 56.8, 55.4, 53.3, 46.7, 41.4, 36.5, 34.7, 31.5, 26.4, 24.9, 22.6, 15.7, 14.0, 9.1.

ESI-MS m/z: Calcd. for $C_{51}H_{53}Cl_3N_4O_{10}S$: 1020.4. Found (M+H)$^+$: 1021.2

To a solution of 30 (845 mg, 0.82 ml), acetic acid (500 mg, 8.28 ml) and $(PPh_3)_2PdCl_2$ (29 mg, 0.04 ml) in anhydrous $CH_2Cl_2$ 20 ml at 23° C. was added, dropwise, $Bu_3SnH$ (650 mg, 2.23 ml). The reaction mixture was stirred at this temperature for 15 min., bubbling was. The crude was quenched with water (50 ml) and extracted with $CH_2Cl_2$ (3×50 ml). The organic layers were dried over sodium sulphate, filtered and concentrated. The crude was purified by flash column chromatography (ethyl acetate/hexane in gradient from 1:5 to 1:3) to obtain compound 31 (730 mg, 90%) as a pale cream yellow solid.

$^1$H-NMR (300 MHz, $CDCl_3$): δ 7.72 (m, 2H), 7.56 (m, 2H), 7.37 (m, 2H), 7.30 (m, 2H), 6.65 (s, 1H), 5.89 (s, 1H), 5.77 (s, 1H), 5.74 (s, 1H), 5.36 (d, J=5.9 Hz, 1H), 5.32 (d, J=5.9 Hz, 1H), 5.20 (d, J=9.0, 1H), 4.75 (d, J=12.0 Hz, 1H), 4.73 (m, 1H), 4.48 (d, J=11.9 Hz, 1H), 4.08 (m, 4H), 3.89 (m, 1H), 3.86, (t, J=6.2 Hz, 1H), 3.70 (s, 3H), 3.69 (s, 3H), 3.38 (m, 1H), 3.25 (m, 1H), 3.02-2.89 (m, 4H), 2.67 (s, 1H), 2.61 (s, 1H), 2.51 (dd, J=14.3 Hz, J=4.5 Hz, 1H), 2.29 (s, 3H), 2.23 (s, 3H), 1.95 (s, 3H), 1.83 (m, 1H).

$^{13}$C-NMR (75 MHz, $CDCl_3$): δ 168.2, 152.5, 148.1, 146.2, 144.4, 144.3, 143.3, 139.6, 134.6, 129.7, 129.6, 126.2, 125.6, 123.4, 123.3, 121.6, 118.5, 116.3, 110.7, 110.2, 105.1, 99.4, 98.5, 75.2, 73.3, 61.7, 58.4, 57.9, 56.3, 56.1, 55.1, 54.7, 53.9, 51.9, 45.2, 40.1, 35.6, 33.3, 24.8, 23.3, 14.5, 7.3.

ESI-MS m/z: Calcd. for $C_{48}H_{49}Cl_3N_4O_{10}S$: 980.3. Found (M+H)$^+$: 981.2

Example 15

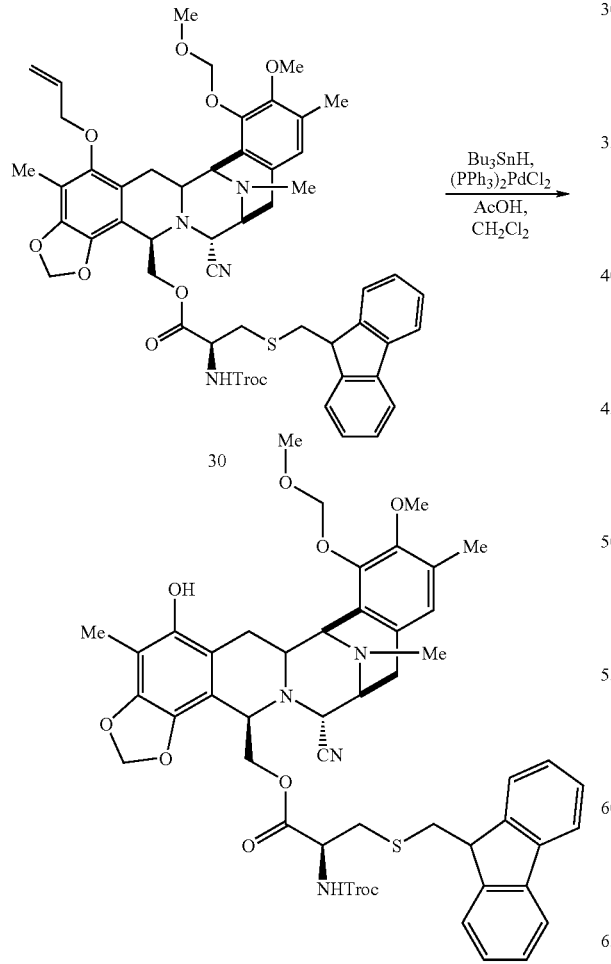

Example 16

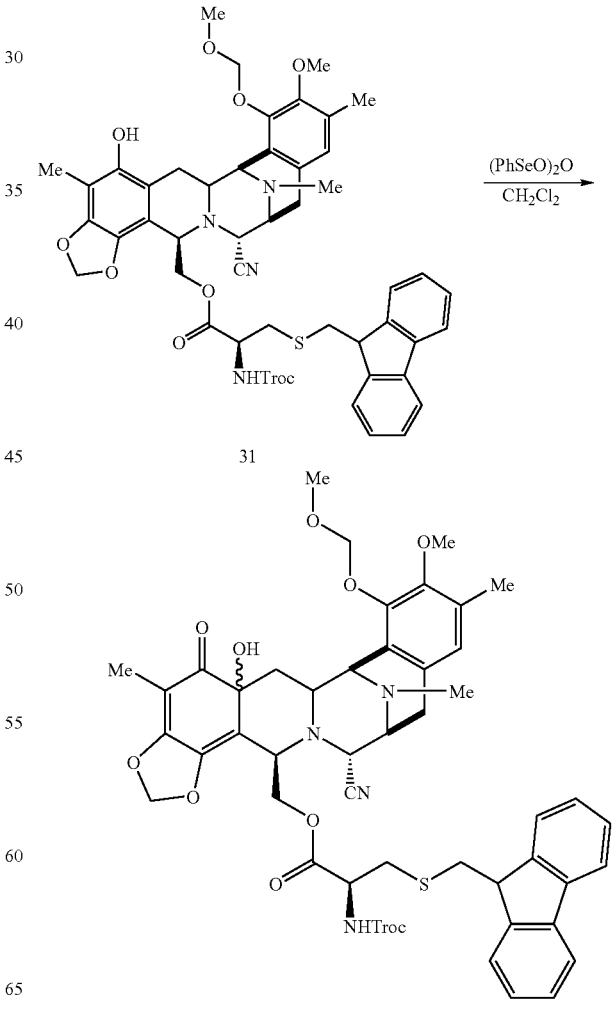

To a solution of 31 (310 mg, 0.32 ml), in anhydrous $CH_2Cl_2$ (15 ml) at −10° C. was added a solution of benzeneseleninic anhydride 70% (165 mg, 0.32 ml), in anhydrous $CH_2Cl_2$ (7 ml), via cannula, keeping the temperature at −10° C. The reaction mixture was stirred at −10° C. for min. A saturated solution of sodium bicarbonate (30 ml) was added at this temperature. The aqueous layer was washed with more $CH_2Cl_2$ (40 ml). The organic layers were dried over sodium sulphate, filtered and concentrated. The crude was purified by flash column chromatography (ethyl acetate/hexane in gradient from 1:5 to 1:1) to obtain 32 (287 mg, 91%, HPLC: 91.3%) as a pale cream yellow solid and as a mixture of two isomers (65:35) which were used in the next step.

$^1$H-NMR (300 MHz, $CDCl_3$): δ (Mixture of isomers) 7.76 (m, 4H), 7.65 (m, 4H), 7.39 (m, 4H), 7.29 (m, 4H), 6.62 (s, 1H), 6.55 (s, 1H), 5.79-5.63 (m, 6H), 5.09 (s, 1H), 5.02 (d, J=6.0 Hz, 1H), 4.99 (d, J=6.0 Hz, 1H), 4.80-4.63 (m, 6H), 4.60 (m, 1H), 4.50 (m, 1H), 4.38 (d, J=12.8 Hz, J=7.5 Hz, 1H), 4.27 (dd, J=12.8 Hz, J=7.5 Hz, 1H), 4.16-3.90 (m, 10H), 3.84 (s, 3H), 3.62 (s, 3H), 3.50 (s, 3H), 3.49 (s, 3H), 3.33-2.83 (m, 14H), 2.45-2.18 (m, 2H), 2.21 (s, 6H), 2.17 (s, 6H), 1.77 (s, 6H), 1.67 (m, 2H).

$^{13}$C-NMR (75 MHz, $CDCl_3$): δ (Mixture of isomers) 168.6, 168.4, 158.6, 154.8, 152.8, 152.5, 147.3, 147.2, 146.8, 144.1, 144.0, 140.8, 139.7, 137.1, 129.8, 129.3, 128.4, 128.7, 126.5, 125.5, 123.7, 123.6, 123.5, 123.4, 122.2, 121.3, 118.3, 115.8, 115.5, 110.2, 106.9, 103.5, 103.2, 100.1, 99.6, 97.9, 97.7, 93.8, 73.4, 70.9, 69.2, 64.9, 62.5, 59.3, 58.9, 58.4, 56.7, 56.3, 56.2, 55.4, 55.2, 55.1, 54.9, 54.7, 54.3, 54.1, 53.8, 52.8, 45.5, 40.5, 40.0, 39.8, 35.8, 35.5, 33.9, 33.7, 30.1, 28.8, 24.2, 24.1, 21.2, 14.5, 14.4, 12.7, 6.0, 5.7.

ESI-MS m/z: Calcd. for $C_{48}H_{49}Cl_3N_4O_{11}S$: 996.3. Found $(M+H)^+$: 997.2

Example 17 lents.) in anhydrous $CH_2Cl_2$ (4.5 ml) was dropwise added triflic anhydride (37.3 ml, 0.22 ml, 2 equivalents.) at −78° C. The reaction mixture was stirred at −78° C. for 20 minutes, then a solution of 32 (110 mg, 0.11 ml, HPLC: 91.3%) in anhydrous $CH_2Cl_2$ (1 ml, for the main addition and 0.5 ml for wash) at −78° C. was added, via cannula. During the addition the temperature was kept at −78° C. in both flasks and the colour changed from yellow to brown. The reaction mixture was stirred at −40° C. for 35 minutes. During this period of time the solution was turned from yellow to dark green. After this time, $^iPr_2NEt$ (153 ml, 0.88 ml, 8 equivalents.) was dropwise added and the reaction mixture was kept at 0° C. for 45 minutes, the colour of the solution turned to brown during this time. Then t-butanol (41.6 ml, 0.44 ml, 4 equivalents.) and 2-$^t$Butyl-1,1,3,3-tetramethylguanidine (132.8 ml, 0.77 ml, 7 equivalents.) were dropwise added and the reaction mixture was stirred at 23° C. for 40 minutes. After this time, acetic anhydride (104.3 ml, 1.10 ml, 10 equivalents.) was dropwise added and the reaction mixture was kept at 23° C. for 1 hour more. Then the reaction mixture was diluted with $CH_2Cl_2$ (20 ml) and washed with aqueous saturated solution of $NH_4Cl$ (50 ml), sodium bicarbonate (50 ml), and sodium chloride (50 ml). The combined organic layers were dried over sodium sulphate, filtered and concentrated. The residue was purified by flash column chromatography (eluent:ethyl acetate/hexane gradient from 1:3 to 1:2) to afford compound 33 (54 mg, 58%) as a pale yellow solid.

$^1$H-NMR (300 MHz, $CDCl_3$): δ 6.85 (s, 1H), 6.09 (s, 1H), 5.99 (s, 1H), 5.20 (d, J=5.8 Hz, 1H), 5.14 (d, J=5.3 Hz, 1H), 5.03 (m, 1H), 4.82 (d, J=12.2 Hz, 1H), 4.63 (d, J=12.0 Hz, 1H), 4.52 (m, 1H), 4.35-4.17 (m, 4H), 3.76 (s, 3H), 3.56 (s, 3H), 3.45 (m, 2H), 2.91 (m, 2H), 2.32 (s, 3H), 2.28 (s, 3H), 2.21 (s, 3H), 2.12 (m, 2H), 2.03 (s, 3H).

$^{13}$C-NMR (75 MHz, $CDCl_3$): δ 168.5, 167.2, 152.7, 148.1, 147.1, 144.5, 139.6, 139.1, 130.5, 129.0, 123.7, 123.5, 123.3,

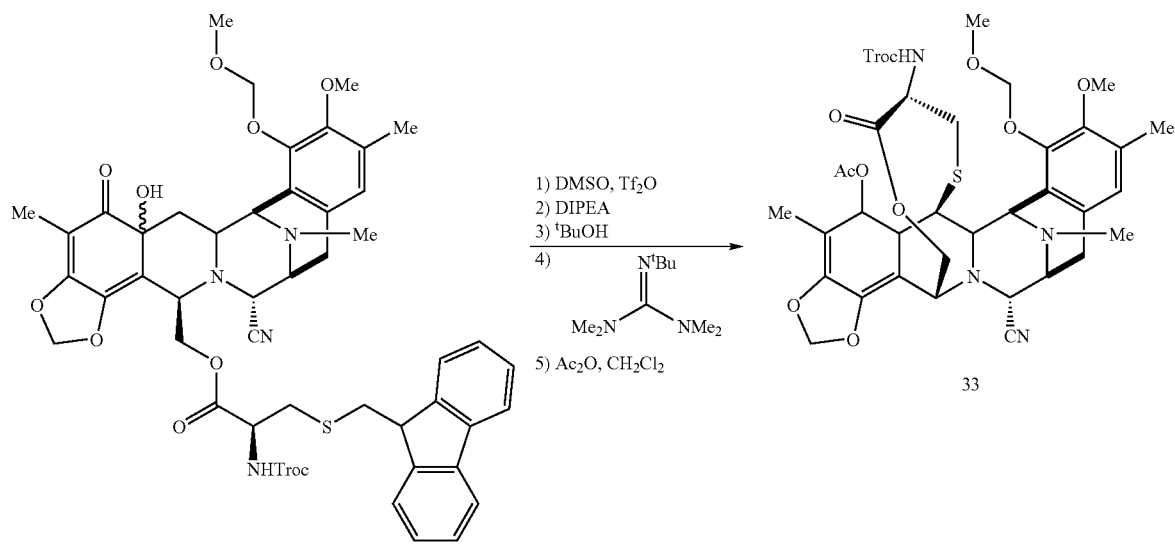

The reaction flask was flamed twice, purged vacuum/Argon several times and kept under Argon atmosphere for the reaction. To a solution of DMSO (39.1 ml, 0.55 ml, 5 equiva- 118.8, 116.5, 112.1, 100.6, 97.8, 73.3, 60.5, 59.4, 59.2, 58.3, 57.6, 57.4, 56.1, 53.3, 53.1, 40.6, 40.0, 31.0, 22.2, 18.9, 14.4, 8.1.

ESI-MS m/z: Calcd. for $C_{36}H_{39}Cl_3N_4O_{11}S$: 842.1. Found (M+H)$^+$: 843.1

Example 18

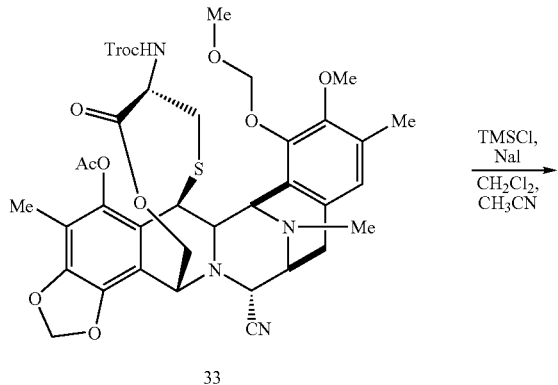

33

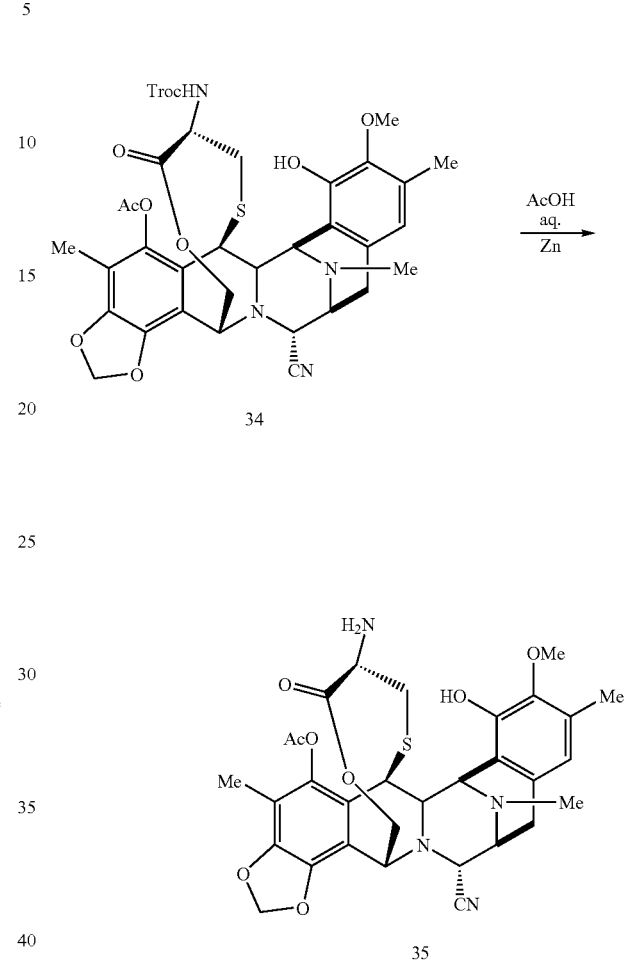

34

To a solution of 33 (12 mg, 0.014 ml) in dry dichloromethane (1.2 ml) and HPLC grade acetonitrile (1.2 ml) was added at 23° C. sodium iodide (21 mg, 0.14 ml) and freshly distilled (over calcium hydride at atmospheric pressure) trimethylsilyl chloride (15.4 mg, 0.14 ml). The reaction mixture turned to orange colour. After 15 min the solution was diluted with dichloromethane (10 ml) and was washed with a freshly aqueous saturated solution of $Na_2S_2O_4$ (3×10 ml). The organic layer was dried over sodium sulphate, filtered and concentrated. It was obtained compound 34 (13 mg, quantitative) as pale yellow solid which was used without further purification.

$^1$H-NMR (300 MHz, CDCl$_3$): δ 6.85 (s, 1H), 6.09 (s, 1H), 5.99 (s, 1H), 5.27 (d, J=5.8 Hz, 1H), 5.14 (d, J=5.3 Hz, 1H), 5.03 (d, J=11.9 Hz, 1H), 4.82 (d, J=12.2, 1H), 4.63 (d, J=13.0 Hz, 1H), 4.52 (m, 1H), 4.34 (m, 1H), 4.27 (bs, 1H), 4.18 (m, 2H), 3.76 (s, 3H), 3.56 (s, 3H), 3.44 (m, 1H), 3.42 (m, 1H), 2.91 (m, 2H), 2.32 (s, 3H), 2.28 (s, 3H), 2.21 (s, 3H), 2.03 (s, 3H).

ESI-MS m/z: Calcd. for $C_{34}H_{35}N_4O_{10}S$: 798.1. Found (M+H)$^+$: 799.1

Example 19

34

35

To a solution of 34 (13 mg, 0.016 ml) in a mixture of acetic acid/H$_2$O (90:10, 1 ml) was added powder Zinc (5.3 mg, 0.081 ml) at 23° C. The reaction mixture was heated at 70° C. for 6 h. After this time, was cooled to 23° C., diluted with CH$_2$Cl$_2$ (20 ml) and washed with aqueous saturated solution of sodium bicarbonate (15 ml) and aqueous solution of Et$_3$N (15 ml). The organic layer was dried over sodium sulphate, filtered and concentrated. The residue was purified by flash column chromatography with Silica-NH$_2$ (eluent: ethyl acetate/hexane gradient from 0:100 to 50:50) to afford compound 35 (6.8 mg, 77% for two steps) as a pale yellow solid.

$^1$H-NMR (300 MHz, CDCl$_3$): δ 6.51 (s, 1H), 6.03 (dd, J=1.3 Hz, J=26.5 Hz, 2H), 5.75 (bs, 1H), 5.02 (d, J=11.6 Hz, 1H), 4.52 (m, 1H), 4.25 (m, 2H), 4.18 (d. J=2.5 Hz, 1H), 4.12 (dd, J=1.9 Hz, J=11.5 Hz, 1H), 3.77 (s, 3H), 3.40 (m, 2H), 3.26 (t, J=6.4 Hz, 1H), 2.88 (m, 2H), 2.30-2.10 (m, 2H), 2.30 (s, 3H), 2.28 (s, 3H), 2.18 (s, 3H), 2.02 (s, 3H).

$^{13}$C-NMR (75 MHz, CDCl$_3$): δ 174.1, 168.4, 147.8, 145.4, 142.9, 140.8, 140.1, 131.7, 130.2, 129.1, 128.3, 120.4, 118.3, 117.9, 113.8, 111.7, 101.7, 61.2, 59.8, 59.2, 58.9, 54.4, 53.8, 54.4, 41.3, 41.5, 34.1, 23.6, 20.3, 15.5, 9.4.

ESI-MS m/z: Calcd. for $C_{31}H_{34}N_4O_8S$: 622.7. Found (M+H)$^+$: 623.2.

Example 20

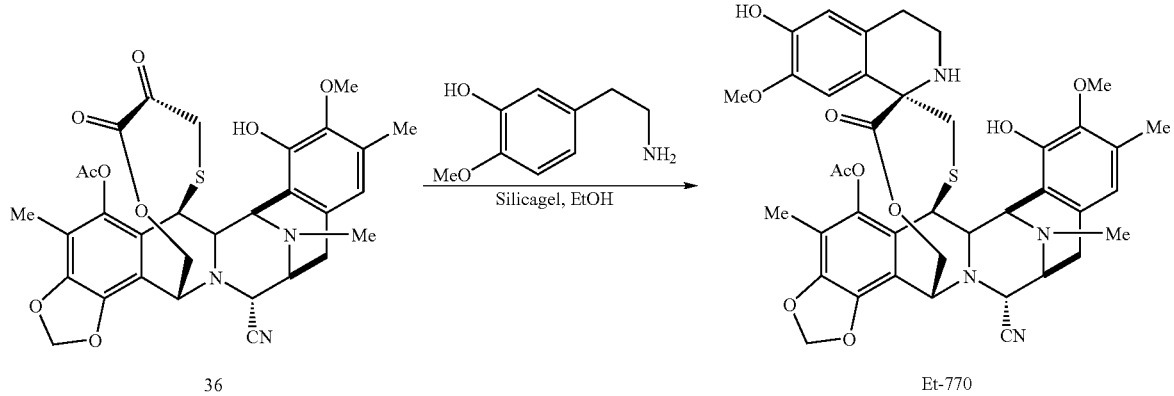

To a solution of 36 (49 mg, 0.08 ml) and 2-[3-hydroxy-4-methoxyphenyl]ethylamine (46.2 mg, 0.27 ml) in ethanol (2.5 ml) was added silica gel (105 mg) at 23° C. The reaction mixture was stirred at 23° C. for 14 h. It was diluted with hexane and poured into a column of chromatography (ethyl acetate/hexane from 1/3 to 1/1) to afford Et-770 (55 mg, 90%) as a pale yellow solid.

$^1$H-NMR (300 MHz, CDCl$_3$): δ 6.60 (s, 1H), 6.47 (s, 1H), 6.45 (s, 1H), 6.05 (s, 1H), 5.98 (s, 1H), 5.02 (d, J=1.4 Hz, 1H), 4.57 (bs, 1H), 4.32 (bs, 1H), 4.28 (d, J=5.3 Hz, 1H), 4.18 (d, J=2.5 Hz, 1H), 4.12 (dd, J=2.1 Hz, J=11.5 Hz, 1H), 3.78 (s, 3H), 3.62 (s, 3H), 3.50 (d, J=5.0 Hz, 1H), 3.42 (m, 1H), 3.10 (ddd, J=4.0 Hz, J=10.0 Hz, J=11.0 Hz, 1H), 2.94 (m, 2H), 2.79 (m, 1H), 2.61 (m, 1H), 2.47 (m, 1H), 2.35 (m, 1H), 2.32 (s, 3H), 2.27 (s, 3H), 2.20 (s, 3H), 2.09 (m, 1H), 2.04 (s, 3H).

ESI-MS m/z: Calcd. for C$_{40}$H$_{42}$N$_4$O$_{10}$S: 770.7. Found (M+H)$^+$: 771.2

Example 22

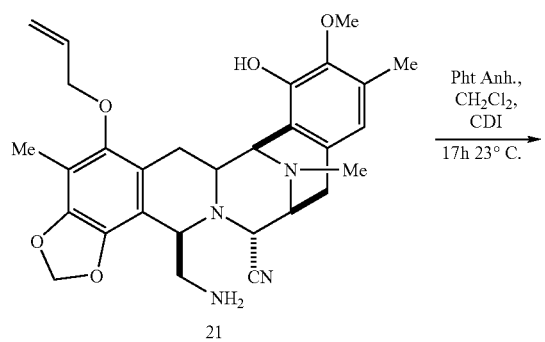

To a solution of 21 (22 mg, 0.042 ml) in CH$_2$Cl$_2$ (0.8 ml) was added phthalic anhydride (6.44 mg, 0.042 ml) and the reaction mixture was stirred for 2 h at 23° C. Then, carbonyldiimidazole (1 mg, 0.006 ml) was added and the mixture was stirred at 23° C. for 7 h. Then, carbonyldiimidazole (5.86 mg, 0.035 ml) was added and the reaction was stirred at 23° C. for an additional 17 h. The solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified by flash column chromatography (SiO$_2$, hexane:ethyl acetate 2:1) to afford 27 (26.4 mg, 96%) as a white solid.

Rf: 0.58 (ethyl acetate).

$^1$H NMR (300 MHz, CDCl$_3$): 7.73-7.64 (m, 4H), 6.40 (s, 1H), 6.12-6.01 (m, 1H), 5.63 (s, 1H), 5.58 (d, J=1.5 Hz, 1H), 5.37 (dd, J$_1$=1.8 Hz, J$_2$=17.4 Hz), 5.23 (dd, J$_1$=1.8 Hz, J$_2$=10.5 Hz, 1H), 5.12 (d, J=1.5 Hz, 1H), 4.22-4.15 (m, 3H), 4.08 (d, J=1.8 Hz, 1H), 3.68 (s, 3H), 3.59-3.55 (m 2H), 3.35 (d, J=8.1 Hz, 1H), 3.27-3.16 (m, 2H), 3.05 (dd, J$_1$=8.1 Hz, J$_2$=18.3 Hz, 1H), 2.64 (d, J=18.0 Hz, 1H), 2.30 (s, 3H), 2.24 (s, 3H), 2.09 (s, 3H), 1.80 (dd, J$_1$=11.4 Hz, J$_2$=15 Hz, 1H);

$^{13}$C NMR (75 MHz, CDCl$_3$): δ 167.7, 148.9, 146.4, 144.2, 142.6, 139.5, 134.0, 133.5, 132.0, 131.0, 128.3, 123.0, 121.3, 120.9, 118.1, 117.5, 116.8, 113.6, 112.4, 100.8, 74.5, 60.6, 60.5, 57.7, 56.6, 55.6, 55.5, 42.3, 41.7, 26.6, 25.5, 15.9, 9.46.

ESI-MS m/z: Calcd. for $C_{37}H_{35}N_4O_7$: 648.79. Found (M+H)$^+$: 649.3.

Example 23

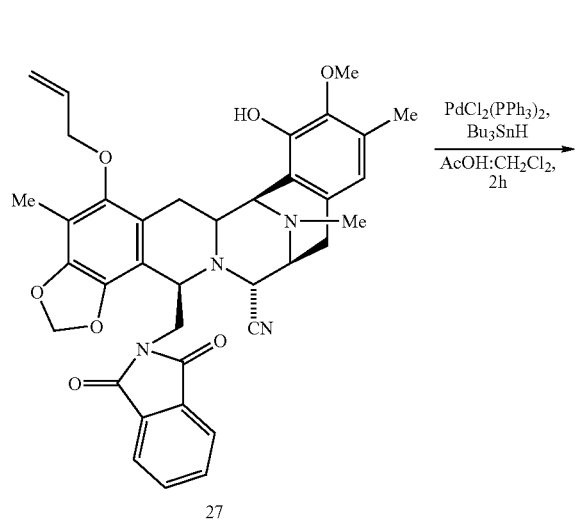

27

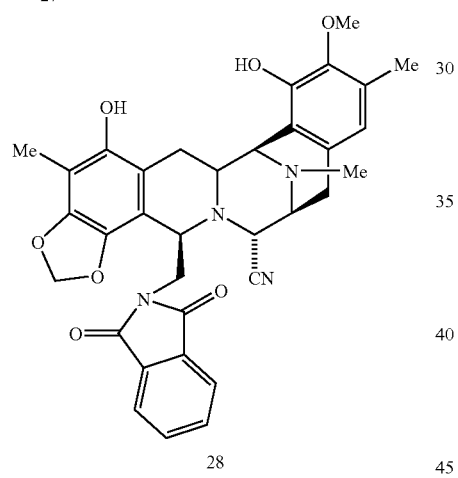

28

To a solution of 27 (26 mg, 0.041 ml) in CH$_2$Cl$_2$ (11 ml), acetic acid (11 ml), (PPh$_3$)$_2$PdCl$_2$ (2.36 mg) and Bu$_3$SnH (28 ml, 0.10 ml) were added at 23° C. After stirring at that temperature for 2 h the reaction was poured into a pad of flash column (SiO$_2$, gradient Hex to hexane:ethyl acetate 2:1) to afford 28 (24.7 mg, 99%) as a white solid.

Rf: 0.33 (hexane:ethyl acetate 2:1).

$^1$H NMR (300 MHz, CDCl$_3$): δ 7.75-7.70 (m, 2H), 7.69-7.65 (m, 2H), 6.39 (s, 1H), 5.82 (bs, 1H), 5.50 (d, J=1.5 Hz, 1H), 5.0 (d, J=1.5 Hz, 1H), 4.45 (bs, 1H), 4.23-4.19 (m, 2H), 4.10-4.09 (m, 1H), 3.73 (s, 3H), 3.60-3.48 (m, 2H), 3.36-3.33 (m, 1H), 3.26-3.20 (m, 1H), 3.14-3.08 (m, 1H), 3.98 (d, J=14.4 Hz, 1H), 2.61 (d, J=18.3 Hz, 1H), 2.30 (s, 3H), 2.23 (s, 3H), 2.06 (s, 3H), 1.85 (dd, J$_1$=12 Hz, J$_2$=15.3 Hz);

$^{13}$C NMR (75 MHz, CDCl$_3$): δ 167.8, 146.4, 145.1, 143.9, 142.7, 137.1, 133.5, 131.9, 130.8, 128.4, 122.9, 120.8, 118.0, 116.8, 114.0, 113.4, 106.4, 100.4, 60.6, 60.5, 57.8, 56.6, 55.5, 55.2, 42.6, 41.5, 25.6, 25.5, 15.8, 8.9.

ESI-MS m/z: Calcd. for $C_{34}H_{32}N_4O_7$: 608.6. Found (M+H)$^+$: 609.2.

Example 24

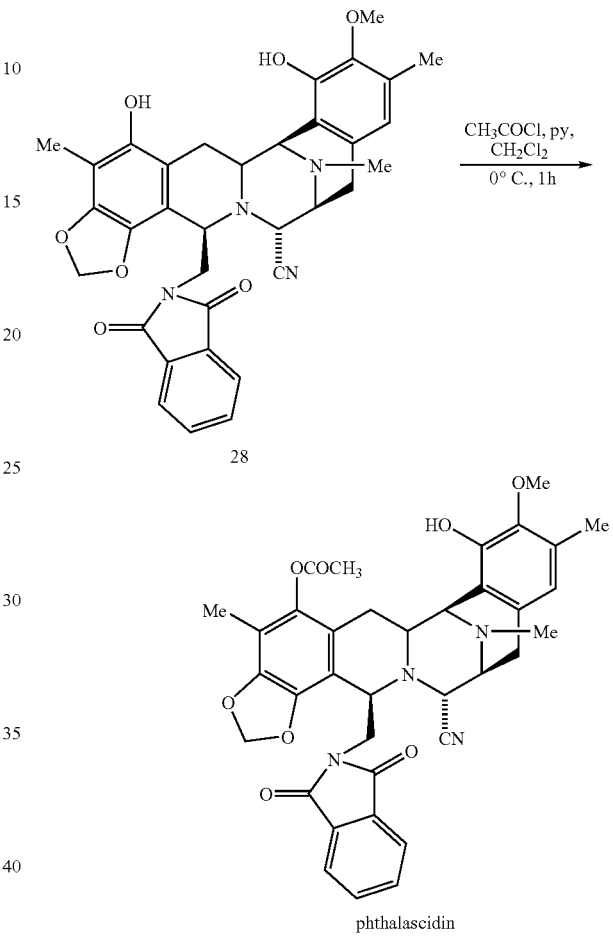

28 phthalascidin

To a solution of 28 (357 mg, 0.058 ml) in CH$_2$Cl$_2$ (3 ml), acetyl chloride (41.58 ml, 0.58 ml) and pyridine (47.3 ml, 0.58 ml) were added at 0° C. The reaction mixture was stirred for 1 h and then, the solution was diluted with CH$_2$Cl$_2$ (15 ml) and washed with 0.1 N HCl (15 ml). The organic layer was dried over sodium sulphate, filtered, and the solvent was eliminated under reduced pressure. The residue was purified by flash column chromatography (RP-18, CH$_3$CN:H$_2$O 60:40) to afford phthalascidin (354 mg, 94%) as a white solid.

Rf: 0.37 (CH$_3$CN:H$_2$O 7:3, RP-18).

$^1$H NMR (300 MHz, CDCl$_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2H), 4.02 (d, J=2.1 Hz, 1H), 3.64-3.62 (m, 5H), 3.33 (d, J=8.4 Hz, 1H), 3.21-3.16 (m, 1H), 3.02 (dd, J$_1$=8.1 Hz, J$_2$=18 Hz, 1H), 2.76 (dd, J$_1$=1.8 Hz, J$_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, J$_1$=12.0 Hz, J$_2$=15.3 Hz, 1H))

$^{13}$C NMR (75 MHz, CDCl$_3$)): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

ESI-MS m/z: Calcd. for $C_{36}H_{34}N_4O_8$: 650. Found (M+H)$^+$: 651.2.

112.7, 111.7, 101.4, 99.1, 79.2, 59.5, 58.8, 57.5, 57.4, 56.4, 55.5, 55.0, 41.3, 39.0, 28.2, 26.4, 24.6, 19.9, 18.4, 15.4, 9.1.

ESI-MS m/z: Calcd. for $C_{38}H_{49}N_5O_{10}$: 735.82. Found (M+H)$^+$: 736.3.

Example 25

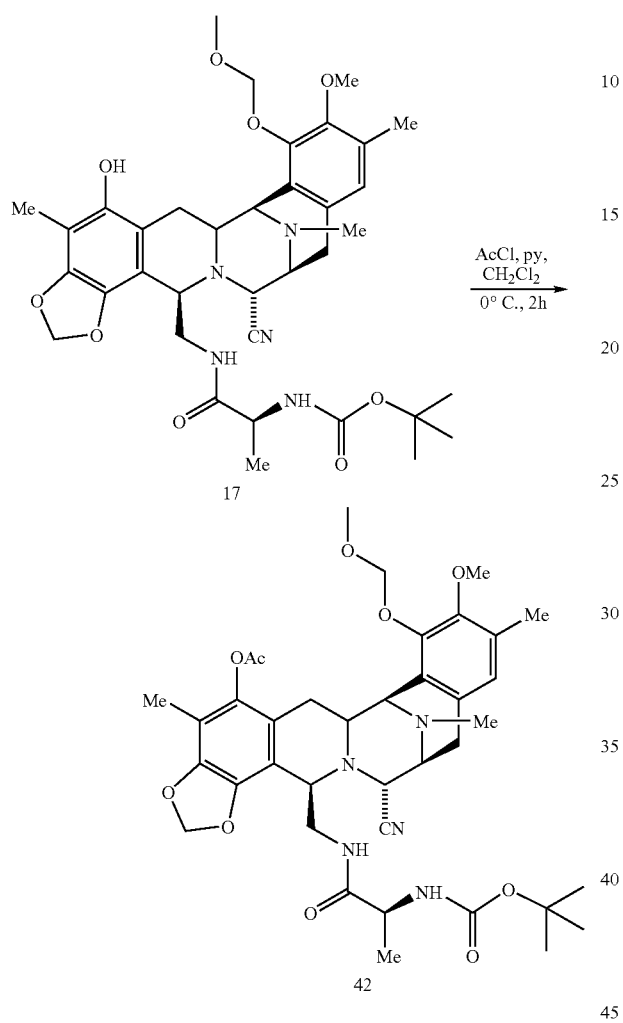

Example 26

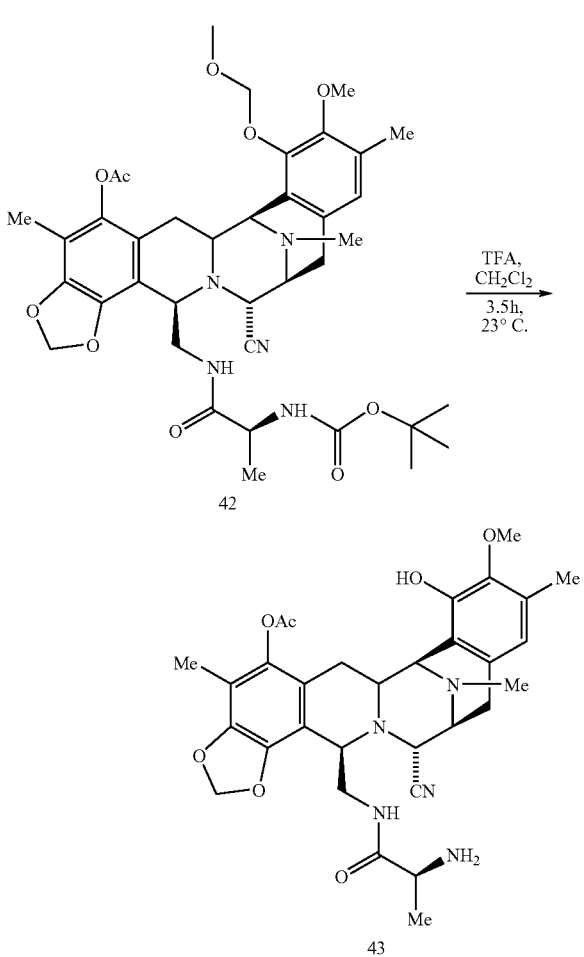

To a solution of 17 (300 mg, 0.432 ml) in $CH_2Cl_2$ (2 ml), acetyl chloride (30.7 ml, 0.432 ml) and pyridine (34.9 ml, 0.432 ml) were added at 0° C. The reaction mixture was stirred for 2 h at that temperature and then, the solution was diluted with $CH_2Cl_2$ (15 ml) and washed with 0.1 N HCl (15 ml). The organic layer was dried over sodium sulphate, filtered, and the solvent was eliminated under reduced pressure to afford 42 (318 mg, 100%) as a white solid that was used in subsequent reactions with no further purification.

Rf: 0.5 (ethyl acetate:methanol 5:1).

$^1$H NMR (300 MHz, CDCl$_3$). δ 6.66 (s, 1H), 5.93 (d, J=1.2 Hz, 1H), 5.83 (d, J=1.2 Hz, 1H), 5.42 (t, J=6.6 Hz, 1H), 5.07 (d, J=5.7 Hz, 1H), 4.98 (d, J=5.7 Hz, 1H), 4.16 (d, J=1.8 Hz, 1H), 4.11 (d, J=2.7 Hz, 1H), 3.98 (bs, 1H), 3.73-3.61 (m, 2H), 3.64 (s, 3H), 3.52-3.48 (m, 1H), 3.50 (s, 3H), 3.33 (d, J=9.6 Hz, 1H), 3.17-3.14 (m, 1H), 2.97-2.87 (m, 1H), 2.75-2.70 (d, J=16.8 Hz, 1H), 2.26 (s, 6H), 2.16 (s, 3H), 1.96 (s, 3H), 1.70 (dd, J$_1$=11.7 Hz, J$_2$=15.6 Hz, 1H), 1.33 (s, 9H), 0.59 (d, J=6.0 Hz, 3H).

$^{13}$C NMR (75 MHz, CDCl$_3$)): δ 172.0, 168.3, 162.3, 148.2, 144.4, 140.4, 140.2, 130.9, 130.5, 125.3, 123.4, 120.8, 117.6,

To a solution of 42 (318 mg, 0.432 ml) in $CH_2Cl_2$ (2.16 ml), trifluoroacetic acid (1.33 ml, 17.30 ml) was added and the reaction mixture was stirred for 3.5 h at 23° C. The reaction was quenched at 0° C. with saturated aqueous sodium bicarbonate (60 ml) and extracted with $CH_2Cl_2$ (2×70 ml). The combined organic layers were dried (sodium sulphate) and concentrated in vacuo. The residue was purified by flash column chromatography (SiO$_2$, ethyl acetate:methanol 20:1) to afford 43 (154 mg, 60%) as a white solid.

Rf: 0.22 (ethyl acetate:methanol 5:1).

$^1$H NMR (300 MHz, CDCl$_3$). δ 6.47 (s, 1H), 6.22 (bs, 1H), 5.95 (d, J=1.2 Hz, 1H), 5.88 (d, J=1.2 Hz, 1H), 4.08-4.06 (m, 2H), 4.01 (bs, 1H), 3.69 (s, 3H), 3.49 (d, J=3.6 Hz, 1H), 3.33 (d, J=8.1 Hz, 1H), 3.26-3.22 (m, 1H), 2.95 (dd, J$_1$=8.1 Hz, J$_2$=18 Hz, 1H), 2.80-2.76 (m, 2H), 2.58 (d, J=18 Hz, 1H), 2.29 (s, 3H), 2.27 (s, 3H), 2.21 (s, 3H), 1.96 (s, 3H), 1.77 (dd, J$_1$=12.3 Hz, J$_2$=15.6 Hz, 1H), 0.90 (d, J=6.9 Hz, 3H).

$^{13}$C NMR (75 MHz, CDCl$_3$)): δ 174.8, 169.0, 146.8, 144.4, 142.8, 140.5, 140.2, 131.1, 128.8, 120.8, 120.5, 117.1, 112.9, 111.6, 101.5, 60.3, 59.0, 56.5, 56.3, 55.6, 55.1, 50.2, 41.6, 39.5, 26.8, 26.3, 24.9, 20.2, 15.4, 9.2.

ESI-MS m/z: Calcd. for C$_{31}$H$_{37}$N$_5$O$_7$: 591.65. Found (M+H)$^+$: 592.3.

Example 27

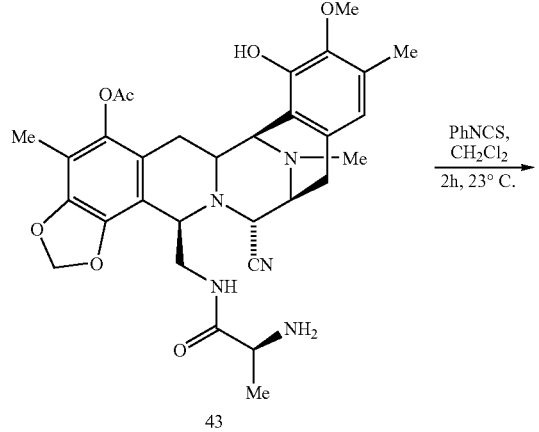

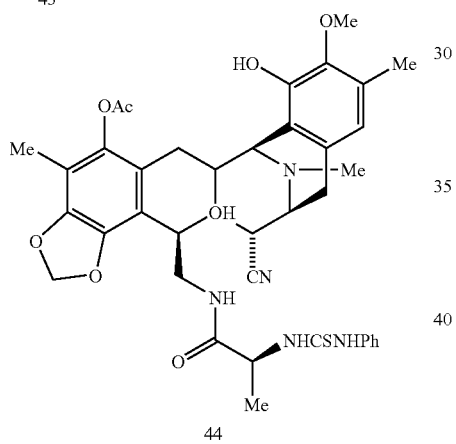

To a solution of 43 (154 mg, 0.26 ml) in CH$_2$Cl$_2$ (1.3 ml), phenyl isothiocyanate (186 ml, 1.56 ml) was added and the mixture was stirred at 23° C. for 2 h. The reaction was concentrated in vacuo and the residue was purified by flash column chromatography (SiO$_2$, gradient Hexane to hexane:ethyl acetate 1:1) to afford 44 (120 mg, 63%) as a white solid.

Rf: 0.41 (ethyl acetate:methanol 5:1).

$^1$H NMR (300 MHz, CDCl$_3$). δ 8.17 (s, 1H), 7.49-7.44 (m, 3H), 7.31-7.24 (m, 3H), 7.05 (d, J=6.9 Hz, 1H), 5.98 (d, J=1.2 Hz, 1H), 5.87 (d, J=1.2 Hz, 1H), 5.52 (bs, 1H), 4.54 (t, J=6.6 Hz, 1H), 4.15 (d, J=2.1 Hz, 1H), 4.03 (d, J=2.7 Hz, 2H), 3.80 (bs, 1H), 3.66 (s, 3H), 3.40 (bs, 1H), 3.32 (d, J=7.8 Hz, 1H), 3.16 (d, J=11.7 Hz, 1H), 2.82-2.61 (m, 3H), 2.29 (s, 3H), 2.20 (s, 3H), 2.01 (s, 3H), 1.99 (s, 3H), 1.80 (dd, J$_1$=12.0 Hz, J$_2$=15.9 Hz, 1H), 0.62 (d, J=6.0 Hz, 3H).

$^{13}$C NMR (75 MHz, CDCl$_3$) δ 178.5, 171.9, 168.7, 146.7, 144.5, 142.6, 140.6, 140.3, 136.3, 131.0, 129.9, 128.9, 126.7, 124.4, 120.9, 120.6, 117.7, 116.6, 112.7, 111.9, 101.4, 60.4, 58.7, 57.5, 56.1, 55.7, 55.1, 53.3, 41.4, 38.8, 26.3, 24.4, 20.2, 18.1, 15.3, 9.2.

ESI-MS m/z: Calcd. for C$_{38}$H$_{42}$N$_6$O$_7$S: 726.3. Found (M+H)$^+$: 727.3.

Example 28

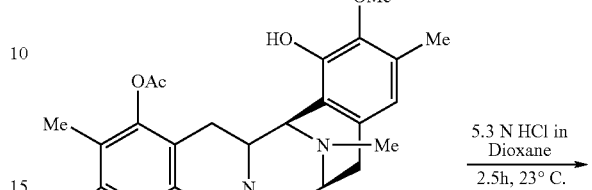

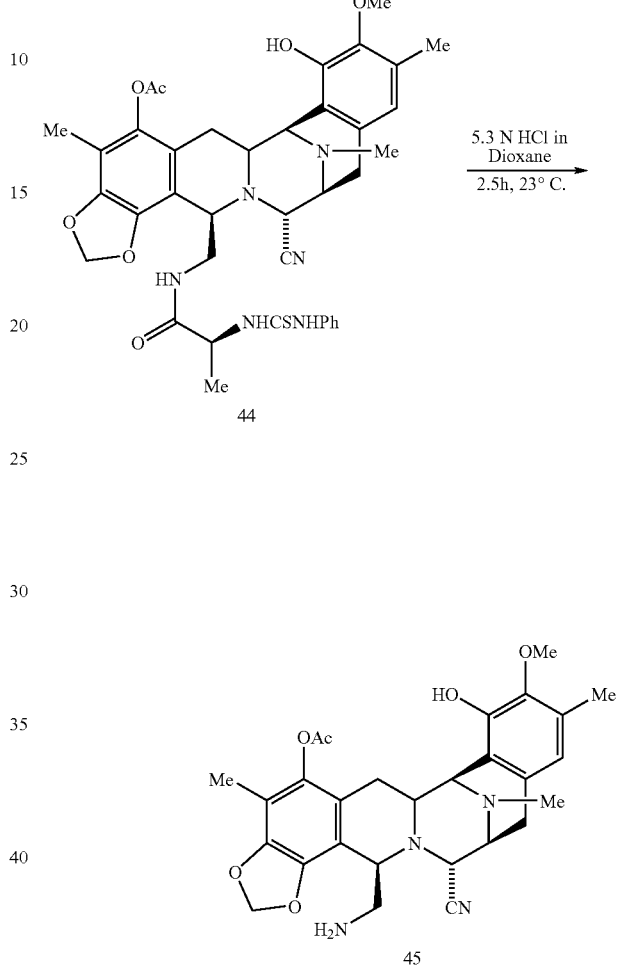

To a solution of 44 (120 mg, 0.165 ml) in dioxane (0.9 ml), 5.3N HCl/dioxane (1.8 ml) was added and the reaction was stirred at 23° C. for 2.5 h. Then, CH$_2$Cl$_2$ (10 ml) and H$_2$O (5 ml) were added to this reaction and the organic layer was decanted. The aqueous phase was basified with saturated aq sodium bicarbonate (20 ml) (pH=8) at 0° C. and then, extracted with CH$_2$Cl$_2$ (2×15 ml). The combined organic extracts were dried (sodium sulphate), and concentrated in vacuo to afford 45 (75 mg, 87%) as a white solid that was used in subsequent reactions with no further purification.

Rf: 0.23 (ethyl acetate:methanol 5:1).

$^1$H NMR (300 MHz, CDCl$_3$): δ 6.43 (s, 1H), 5.94 (d, J=1.2 Hz, 1H), 5.87 (d, J=1.2 Hz, 1H), 4.10 (d, J=2.1 Hz, 1H), 3.98 (d, J=2.4 Hz, 1H), 3.91 (bs, 1H), 3.69 (s, 3H), 3.34-3.25 (m, 2H), 3.05 (dd, J$_1$=1.8 Hz, J$_2$=8.1 Hz, 1H), 2.80-2.73 (m, 3H), 2.46 (d, J=18 Hz, 1H), 2.30 (s, 3H), 2.28 (s, 3H), 2.20 (s, 3H), 1.98 (s, 3H), 1.79 (dd, J$_1$=12.6 Hz, J$_2$=16.2 Hz, 1H);

$^{13}$C NMR (75 MHz, CDCl$_3$)): δ 168.7, 146.7, 144.4, 142.9, 140.4, 130.4, 128.9, 121.1, 120.8, 117.8, 116.8, 113.6, 111.5, 101.4, 67.6, 60.5, 59.8, 58.4, 56.6, 55.8, 55.3, 43.6, 41.8, 31.3, 25.6, 20.2, 15.6, 9.2.

ESI-MS m/z: Calcd. for $C_{28}H_{32}N_4O_6$: 520.58. Found (M+H)$^+$: 521.3.

Example 29

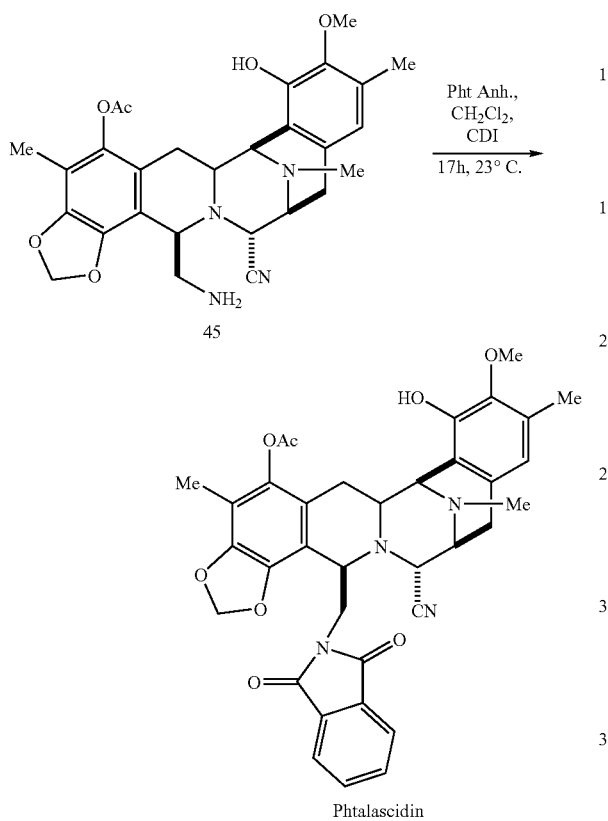

Phtalascidin

ESI-MS m/z: Calcd. for $C_{36}H_{34}N_4O_8$: 650. Found (M+H)$^+$: 651.2.

Example 30

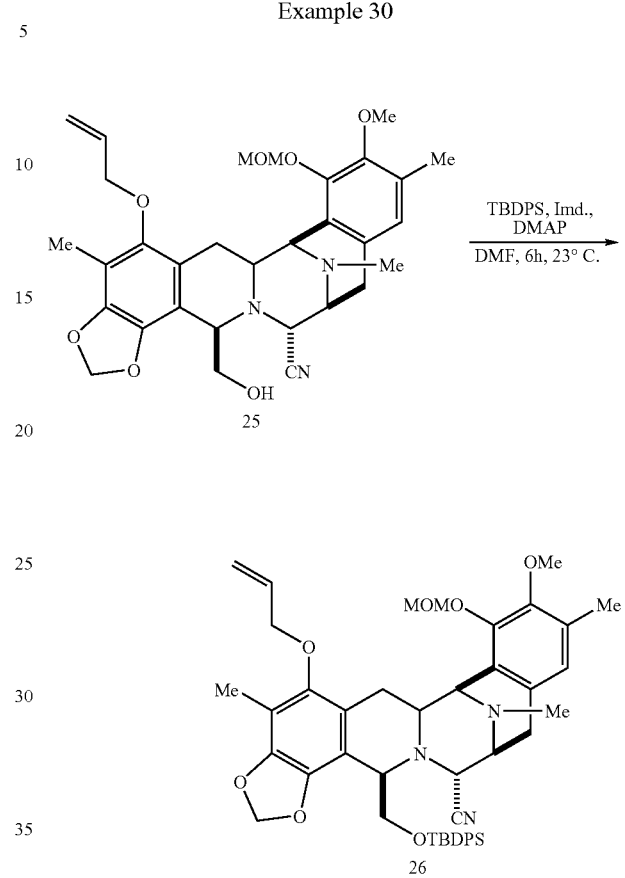

To a solution of 45 (10 mg, 0.02 ml) in $CH_2Cl_2$ (0.4 ml) was added phthalic anhydride (2.84 mg, 0.02 ml) and the reaction mixture was stirred for 2 h at 23° C. Then, carbonyldiimidazole (0.5 mg, 0.003 ml) was added and the mixture was stirred at 23° C. for 7 h. Then, carbonyldiimidazole (2.61 mg, 0.016 ml) was added and the reaction was stirred at 23° C. for an additional 17 h. The solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography (RP-18, $CH_3CN:H_2O$ 60:40) to afford phtalascidin (11.7 mg, 93%) as a white solid.

Rf: 0.37 ($CH_3CN:H_2O$ 7:3, RP-18).

$^1$H NMR (300 MHz, $CDCl_3$): δ 7.72-7.68 (m, 2H), 7.67-7.63 (m, 2H), 6.38 (s, 1H), 5.69 (d, J=1.2 Hz, 1H), 5.64 (d, J=1.2 Hz, 1H), 5.30 (bs, 1H), 4.25-4.21 (m, 2H), 4.02 (d, J=2.1 Hz, 1H), 3.64-3.62 (m, 5H), 3.33 (d, J=8.4 Hz, 1H), 3.21-3.16 (m, 1H), 3.02 (dd, $J_1$=8.1 Hz, $J_2$=18 Hz, 1H), 2.76 (dd, $J_1$=1.8 Hz, $J_2$=15.6 Hz, 1H), 2.63 (d, J=17.7 Hz, 1H), 2.29 (s, 3H), 2.28 (s, 3H), 2.21 (s, 3H), 2.0 (s, 3H), 1.73 (dd, $J_1$=12.0 Hz, $J_2$=15.3 Hz, 1H));

$^{13}$C NMR (75 MHz, $CDCl_3$)): δ 168.5, 167.6, 146.2, 144.2, 142.5, 141.0, 140.5, 133.4, 131.8, 130.7, 128.2, 120.9, 120.8, 117.9, 116.4, 113.6, 101.1, 60.4, 60.0, 57.0, 56.3, 55.6, 55.4, 41.6, 41.5, 26.5, 25.2, 20.2, 15.7, 9.4.

To a solution of 25 (18 mg, 0.032 ml) in DMF (0.05 ml), cat. DMAP (0.5 mg, 0.004 ml), imidazole (5 mg, 0.08 ml) and tert-Butyldiphenylsilyl chloride (12.5 ml, 0.048 ml) were added at 0° C. and the reaction mixture was stirred for 6 h at 23° C. Water (10 ml) was added at 0° C. and the aqueous phase was extracted with hexane:ethyl acetate 1:10 (2×10 ml). The organic layer was dried (sodium sulphate), filtered, and the solvent was removed under reduced pressure. The crude was purified by flash column chromatography ($SiO_2$, hexane:ethyl acetate 3:1) to afford 26 (27 mg, 88%) as a white solid.

Rf: 0.29 (hexane:ethyl acetate 3:1).

$^1$H NMR (300 MHz, $CDCl_3$) δ 7.61-7.58 (m, 2h), 7.42-7.28 (m, 8H), 6.71 (s, 1H), 6.19-6.02 (m, 1H), 5.78 (d, J=1.2 Hz, 1H), 5.64 (d, J=1.2 Hz, 1H), 5.40 (dd, $J_1$=1.2 Hz, $J_2$=17.1 Hz, 1H), 5.27 (dd, $J_1$=1.2 Hz, $J_2$=10.2 Hz, 1H), 5.13 (s, 2H), 4.45 (d, J=2.4 Hz, 1H), 4.24 (d, J=2.1 Hz, 1H), 4.17-4.06 (m, 3H), 3.75 (s, 3H), 3.64 (dd, $J_1$=2.4 Hz, $J_2$=9.9 Hz, 1H), 3.59 (s, 3H), 3.42-3.21 (m, 4H), 3.10 (dd, $J_1$=8.1 Hz, $J_2$=17.7 Hz, 1H), 2.70 (d, J=17.7 Hz, 1H), 2.33 (s, 3H), 2.26 (s, 3H), 2.11 (s, 3H), 2.08-1.89 (m, 1H), 0.87 (s, 9H);

$^{13}$C NMR (75 MHz, $CDCl_3$): δ 148.5, 148.3, 148.1, 144.0, 139.0, 135.6, 135.4, 133.8, 133.1, 132.6, 130.5, 130.3, 129.6, 129.4, 127.5, 127.4, 125.1, 124.3, 121.6, 118.5, 117.5, 112.9, 111.7, 100.8, 99.2, 74.0, 67.7, 61.5, 59.6, 59.0, 57.7, 57.1, 55.4, 41.6, 29.6, 26.6, 25.5, 18.8, 15.8, 9.2.

ESI-MS m/z: Calcd. for $C_{47}H_{55}N_3O_7Si$: 801.3. Found (M+H)$^+$: 802.3.

Example 31

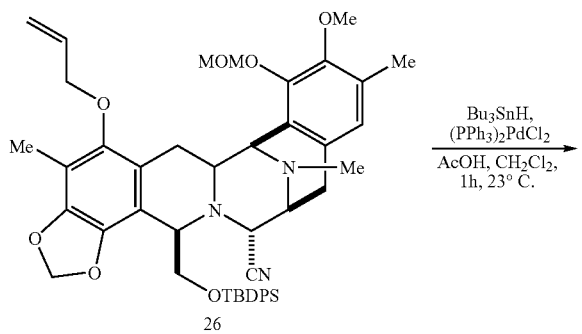

To a solution of 26 (7 mg, 0.0087 ml) in $CH_2Cl_2$ (0.15 ml), acetic acid (2.5 ml, 0.044 ml), $(PPh_3)_2PdCl_2$ (0.5 mg, 6.96× 10$^{-4}$ ml) and $Bu_3SnH$ (3.5 ml, 0.013 ml) were added at 23° C. The reaction mixture was stirred at that temperature for 1 h. The solution was diluted with a mixture of hexane:ethyl acetate 5:1 (0.5 ml) and poured into a pad of flash column (SiO$_2$, gradient 5:1 to 1:1 hexane:ethyl acetate) affording ET-11 (5 mg, 75%) as a white solid.

Rf: 0.36 (hexane:ethyl acetate 1:5, silica).

$^1$H NMR (300 MHz, CDCl$_3$): δ 7.56 (m, 2h), 7.41-7.25 (m, 8H), 6.67 (s, 1H), 5.72 (d, J=1.0 Hz, 1H), 5.58 (d, J=1.0 Hz, 1H), 5.51 (s, 1H), 5.38 (d, J=5.75 Hz, 1H), 5.16 (d, J=5.7 Hz, 1H), 4.57 (d, J=2.9 Hz, 1H), 4.21 (m, 1H), 4.09 (m, 1H), 3.72 (s, 3H), 3.71 (s, 3H), 3.68 (dd, J$_1$=2.1 Hz, J$_2$=10.4 Hz, 1H), 3.38-3.26 (m, 3H), 3.11 (dd, J$_1$=2.5 Hz, J$_2$=15.7 Hz, 1H), 3.01 (dd, J$_1$=8.9 Hz, J$_2$=17.9 Hz, 1H), 2.70 (d, J=17.9 Hz, 1H), 2.31 (s, 3H), 2.25 (s, 3H), 2.06 (s, 3H), 1.89 (dd, J$_1$=12.1 Hz, J$_2$=15.7 Hz, 1H), 0.9 (s, 9H).);

$^{13}$C NMR (75 MHz, CDCl$_3$): δ 149.0, 147.4, 145.3, 144.3, 136.3, 135.7, 135.4, 133.2, 130.9, 130.5, 129.6, 129.5, 127.5, 125.0, 118.6, 112.5, 112.1, 105.7, 100.5, 99.8, 68.5, 61.5, 59.7, 58.8, 57.7, 56.9, 56.5, 55.4, 41.7, 26.6, 26.2, 25.5, 18.9, 15.8, 14.2, 8.7.

ESI-MS m/z: Calcd. for $C_{44}H_{51}N_3O_7Si$: 761. Found (M+H)$^+$: 762.

Example 32

A solution of 2 (3.0 g, 5.46 ml) and phenyl isothiocyanate (3.92 mL, 32.76 ml) in $CH_2Cl_2$ (27 ml) was stirred at 23° C. for 1.5 h. The reaction mixture was partitioned between $CH_2Cl_2$ (10 ml) and $H_2O$ (5 ml). The organic layer was dried over sodium sulphate, filtered and concentrated. The residue was purified by flash column chromatography (SiO$_2$, gradient Hex to 2:3 hexane:ethyl acetate) to give 3 (3.29 g, 88%) as a yellow solid.

Rf: 0.27 (ACN:H$_2$O 3:2, RP-C18);

$^1$H NMR (300 MHz, CDCl$_3$): δ 7.77 (bs, 1H), 7.42-7.11 (m, 5H), 6.65 (d, 1H), 6.29 (s, 1H), 5.6-5.5 (m, 1H), 4.19-4.14 (m, 2 h), 4.08 (d, 1H), 3.92 (s, 3H), 3.87-3.65 (m, 6H), 3.77 (s, 3H), 3.37-2.98 (m, 8H), 2.50 (d, 1H), 2.31 (s, 3H), 2.20 (s, 3H), 1.96 (d, 1H), 1.87 (s, 3H), 1.81-1.75 (m, 1H), 0.96 (d, 3H);

$^{13}$C NMR (75 MHz, CDCl$_3$): δ 185.7, 180.9, 178.9, 172.0, 155.7, 147.1, 143.2, 142.4, 136.0, 135.1, 130.5, 129.9, 129.3, 128.5, 126.9, 124.4, 120.2, 117.4, 116.3, 77.1, 60.9, 58.6, 56.2, 55.8, 55.0, 54.6, 53.5, 41.7, 40.3, 25.1, 24.5, 18.4, 15.8, 8.7

ESI-MS m/z: Calcd. for $C_{36}H_{40}N_6O_6S$: 684.8. Found (M+H)$^+$: 685.2.

ESI-MS m/z: Calcd. for $C_{26}H_{30}N_4O_5$: 478.5. Found (M+H)$^+$: 479.2

Example 33

Example 34

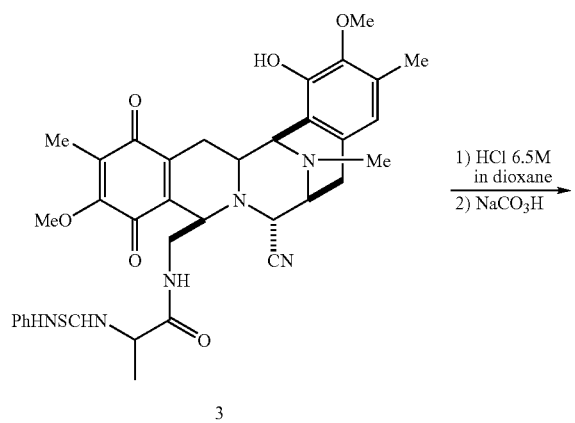

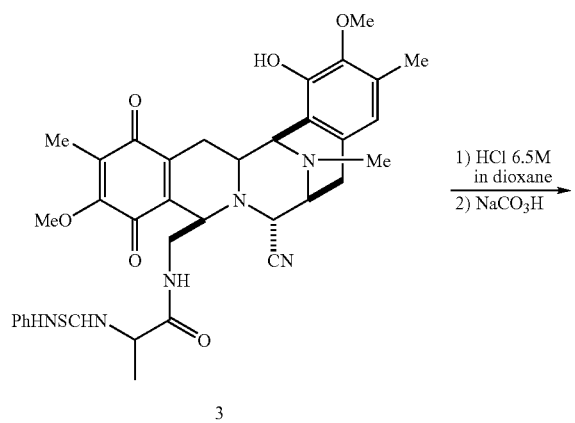

A solution of 3 (0.143 g, 0.208 ml) in 6.5 M HCl/dioxane (150 ml) was stirred at 23° C. for 6 h. Then, toluene (3 ml) was added to this reaction and the organic layer was decanted. The residue was partitioned between saturated aqueous sodium bicarbonate (3 ml) and CHCl$_3$ (3×3 ml) The organic layers were dried and concentrated to afford title compound as a mixture of 4 and 6 (4:6 90:10) which slowly cyclizes to 6 on standing.

Rf: 0.4 (ethyl acetate:methanol 5:1, silica);

$^1$H NMR (300 MHz, CDCl$_3$): δ 6.45 (s, 1H), 4.16 (m, 1H), 4.02 (d, 1H), 3.96 (s, 3H), 3.79 (m, 2 h), 3.75 (s, 3H), 3.35 (m, 1H), 3.20-3.00 (m, 3H), 2.87 (d, 1H), 2.75 (d, 1H), 2.43 (d, 1H), 2.34 (s, 3H), 2.30 (s, 3H), 1.93 (s, 3H), 1.72-1.5 (m, 3H);

A solution of 3 (0.143 g, 0.208 ml) in 6.5M HCl/dioxane (150 ml) was stirred at 23° C. for 1 h. Evaporation of the solvent gave a residue which was purified by flash column chromatography (ethyl acetate/methanol/triethylamine 100:25:0.1) to give 6 (80 mg, 83%) as a yellow solid.

Rf: 0.26 (ACN:H$_2$O 3:2, RP-C18);

$^1$H NMR (500 MHz, CDCl$_3$): δ 6.46 (s, 1H), 5.9 (bs, 1H) 4.67 (dd, J=18.3 Hz, J=7.8 Hz, 1H), 4.24 (d, 1H), 4.16 (s, 3H), 3.93 (d, J=2.7 Hz, 1H), 3.8 (m, 2 h), 3.77 (s, 3H), 3.45 (m, 2 h), 3.08 (dd, J=17.9 Hz, J=3.6 Hz, 1H), 2.78 (m, 1H), 2.55 (d, 1H), 2.3 (m, 1H), 2.3 (s, 3H), 2. 28 (s, 3H), 1.90 (s, 3H);

$^{13}$C NMR (75 MHz, CDCl$_3$): δ 186.2, 162.1, 154.9, 146.9, 145.3, 143.0, 130.1, 129.4, 128.1, 125.0, 121.4, 116.4, 116.2, 66.6, 60.7, 60.7, 60.1, 59.6, 58.8, 55.6, 54.9, 41.9, 25.3, 24.7, 15.7, 8.9.

ESI-MS m/z: Calcd. for $C_{26}H_{28}N_4O_4$: 460.5. Found (M+H)+: 461.1

ESI-MS m/z: Calcd. for $C_{28}H_{32}N_4O_6$: 520.6. Found (M+H)+: 521.1

Example 35

Example 36

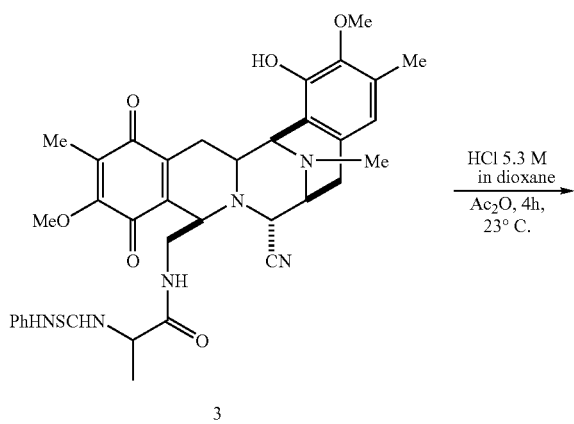

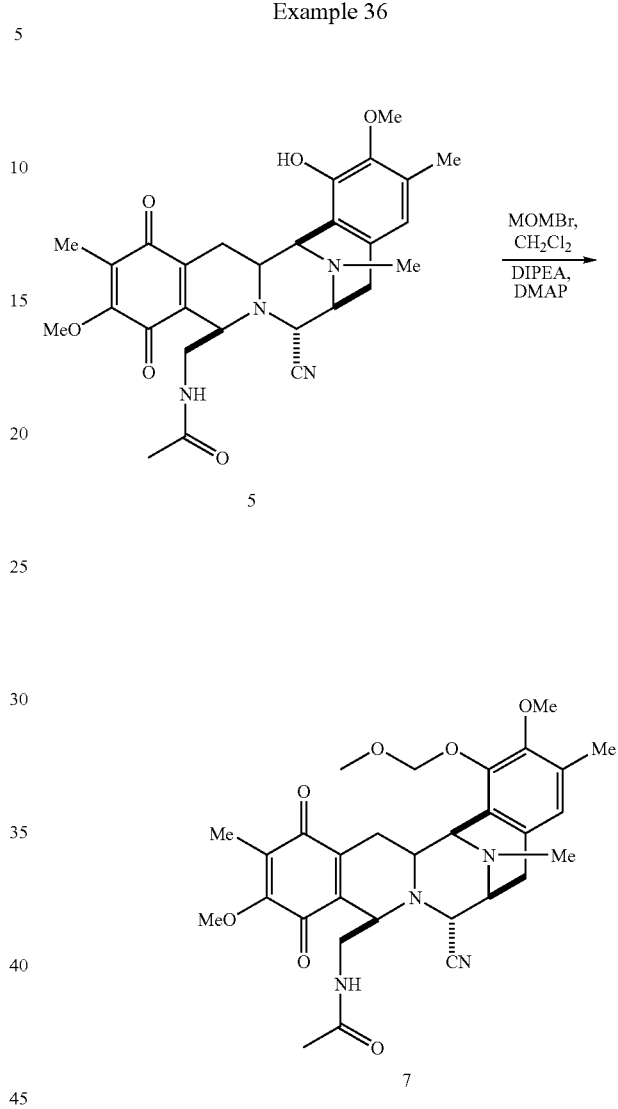

To a solution of 3 (2.38 g, 3.47 ml) in dioxane (5 ml) 5.3M HCl in dioxane (34 ml) was added and the reaction was stirred at 23° C. for 45 minutes. Then Ac$_2$O (51 ml, 539.5 ml) was added and the mixture was stirred for 4 h. The reaction was cooled at 0° C. and partitioned between aqueous saturated Na$_2$CO$_3$ (300 ml) and ethyl acetate (300 ml) at this temperature. The organic phase was dried over sodium sulphate, filtered and concentrated. The residue was purified by flash column chromatography (SiO$_2$, gradient CH$_2$Cl$_2$ to CH$_2$Cl$_2$: ethyl acetate 1:2) to give 5 (1.75 g, 97%) as a yellow solid.

Rf: 0.53 (ACN:H$_2$O 3:2, RP-C18);

$^1$H NMR (300 MHz, CDCl$_3$): δ 6.51 (s, 1H), 5.98 (bs, 1H), 4.84 (dd, 1H), 4.17 (d, 1H), 4.00 (d, 1H), 3.99 (s, 3H), 3.85 (bs, 1H), 3.81 (m, 1H), 3.74 (s, 3H), 3.70 (d, 1H), 3.23 (m, 1H), 3.11 (dd, 1H), 3.09 (m, 1H), 2.93 (m, 2 h), 2.44 (d, 1H), 3.67 (s, 3H), 2.25 (s, 3H), 1.70 (s, 3H), 1.60-1.50 (m, 2 h), 1.29 (s, 3H);

$^{13}$C NMR (75 MHz, CDCl$_3$): δ 185.9, 180.8, 169.9, 160.2, 156.2, 147.0, 143.1, 140.4, 136.1, 130.6, 129.6, 127.9, 120.4, 117.2, 61.0, 60.7, 58.6, 56.1, 55.7, 55.1, 54.3, 41.8, 41.1, 25.7, 23.9, 22.2, 15.7, 8.7.

To a solution of 5 (1.75 g, 3.36 ml) in CH$_2$Cl$_2$ (17 ml) diisopropylethylamine (11.71 ml, 67.23 ml), DMAP (20 mg, 0.17 ml) and bromomethyl methyl ether (4.11 ml, 50.42 ml) were added at 0° C. After 6 h at 23° C. the reaction was partitioned between CH$_2$Cl$_2$ (50 ml) and aqueous saturated sodium bicarbonate (25 ml). The organic layer was dried over sodium sulphate and the solvent was eliminated under reduced pressure. The crude was purified by flash column chromatography (RP-18, CH$_3$CN/H$_2$O 1/1) to give 7 (1.32 g, 70%) as a yellow solid.

Rf: 0.34 (ACN:H$_2$O 2:3, RP-C18);

$^1$H NMR (300 MHz, CDCl$_3$): δ 6.74 (s, 1H), 5.14 (s, 2 h), 4.82 (m, 1H), 4.22 (d, 1H), 4.00 (s, 3H), 4.0 (m, 1H), 3.83 (m, 2 h), 3.7 (s, 3H), 3.58 (s, 3H), 3.4 (m, 1H), 3.2-2.95 (m, 6H), 2.43 (d, 1H), 2.37 (s, 3H), 2.22 (s, 3H), 1.89 (s, 3H), 1.5-1.4 (m, 2 h), 1.31 (s, 3H);

$^{13}$C NMR (75 MHz, CDCl$_3$): δ 185.9, 180.7, 169.6, 156.2, 148.9, 148.5, 140.3, 136.2, 131.3, 130.1, 127.7, 124.6, 123.7, 117.3, 99.5, 99.2, 60.9, 59.7, 58.8, 57.6, 56.4, 55.7, 55.0, 54.2, 51.0, 41.6, 41.0, 40.5, 25.5, 23.9, 22.3, 19.3, 15.6, 14.6, 8.6.

ESI-MS m/z: Calcd. for $C_{30}H_{36}N_4O_7$: 564.6. Found (M+H)$^+$: 565.3

Example 37

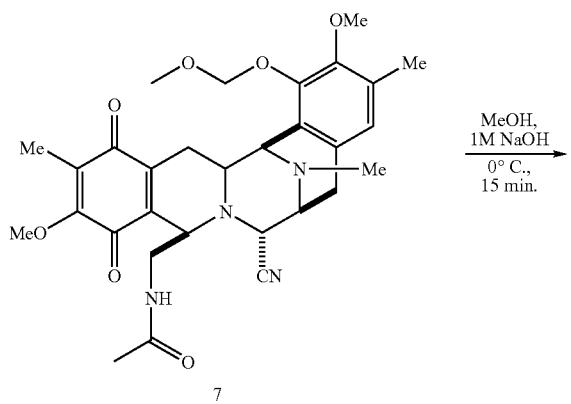

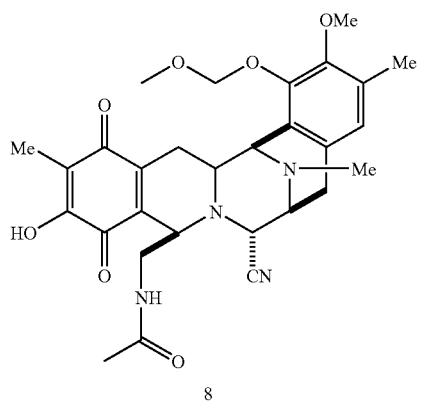

8

To a solution of 7 (0.37 g, 0.65 ml) in methanol (74 ml) at 0° C. was added 1M sodium hydroxide (130 ml). The reaction was stirred for 15 minutes and then, quenched at 0° C. with 6M HCl to pH=5. The mixture was extracted with ethyl acetate (3×50 ml) and the combined organic layers were dried over sodium sulphate and concentrated in vacuo. The residue was purified by flash column chromatography (RP-C18 $CH_3CN:H_2O$ 1/:1) to afford 8 (232 mg, 65%) as a yellow oil.

Rf: 0.5 (ACN:$H_2O$ 3:2, RP-C18);

$^1$H NMR (300 MHz, CDCl$_3$): δ 6.75 (s, 1H), 5.15 (s, 2 h), 4.86 (m, 1H), 4.26 (d, 1H),), 4.01 (d, 1H), 3.88-3.81 (m, 2 h), 3.70 (s, 3H), 3.58 (s, 3H), 3.39 (m, 1H), 3.27-3.21 (m, 1H), 3.18-3.08 (m, 2 h), 3.03-2.97 (m, 1H) 2.47 (d, 1H), 2.37 (s, 3H), 2.22 (s, 3H), 1.90 (s, 3H), 1.57-1.46 (m, 2 h), 1.33 (s, 3H);

$^{13}$C NMR (75 MHz, CDCl$_3$): δ 185.3, 180.6, 175.9, 170.1, 151.5, 148.9, 148.6, 143.3, 133.7, 131.5, 129.9, 124.7, 123.5, 117.1, 117.0, 99.2, 59.8, 58.7, 57.8, 56.3, 55.3, 54.9, 54.3, 41.5, 40.7, 29.6, 25.5, 24.4, 22.2, 20.7, 15.7, 8.0.

ESI-MS m/z: Calcd. for $C_{29}H_{34}N_4O_7$: 550.6. Found (M+H)$^+$: 551.2

Example 38

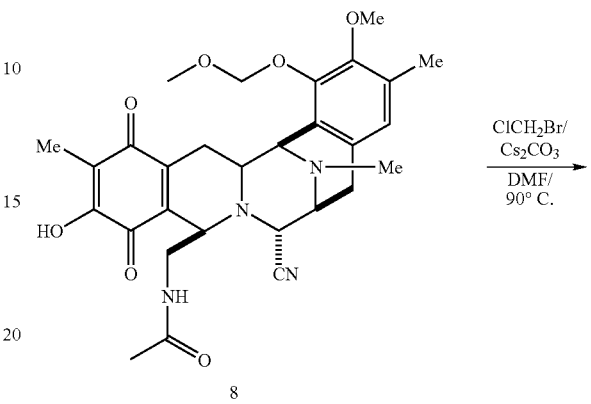

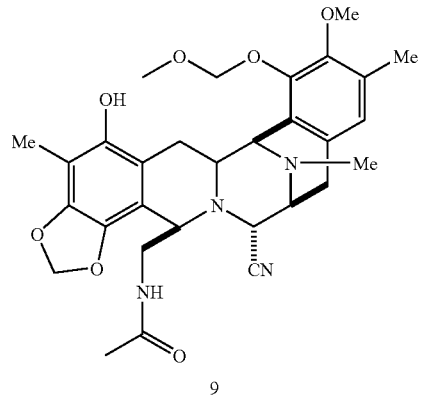

9

To a degassed solution of compound 8 (240 mg, 0.435 ml) in DMF (30 ml) 10% Pd/C (48 mg) was added and the reaction was stirred under H$_2$ (atmospheric pressure.) for 1 h. The reaction was filtered through a pad of celite under Argon to a Schlenk tube, as a colourless solution, containing anhydrous Cs$_2$CO$_3$ (240 mg, 0.739 ml). Then, bromochloromethane (0.566 ml, 8.71 ml) was added. The tube was sealed and stirred at 90° C. for 3 h. The reaction was cooled and filtrated through celite and washed with CH$_2$Cl$_2$. The organic layer was concentrated and dried (sodium sulphate) to afford 9 as a brown oil that was used in the next step with no further purification.

Rf: 0.36 (SiO$_2$, hexane:ethyl acetate 1:5)

$^1$H NMR (300 MHz, CDCl$_3$): δ 6.71 (s, 3H), 5.89 (d, 1H), 5.81 (d, 1H), 5.63 (bs, 1H), 5.33 (d, 1H), 5.17 (d, 1H), 4.97 (m, 1H), 4.20 (d, 1H), 4.09 (m, 1H), 3.99 (m, 1H), 3.68 (m, 1H), 3.65 (s, 6H), 3.59-3.47 (m, 4H), 3.37-3.27 (m, 2 h), 3.14-2.97 (m, 2 h), 2.62 (d, 1H), 2.32 (s, 3H), 2.20 (s, 3H), 2.08 (s, 3H), 1.72 (m, 1H), 1.36 (s, 3H);

$^{13}$C NMR (75 MHz, CDCl$_3$): δ 169.8, 149.1, 147.4, 145.5, 136.2, 130.9, 130.8, 125.0, 122.9, 117.7, 112.6, 111.8, 106.4, 100.8, 99.8, 59.8, 58.9, 57.7, 56.6, 56.4, 55.5, 55.2, 41.6, 40.1, 29.6, 25.9, 25.0, 22.6, 15.6, 8.8.

ESI-MS m/z: Calcd. for $C_{30}H_{36}SiN_4O_7$: 564.6. Found (M+H)$^+$: 565.3.

Example 39

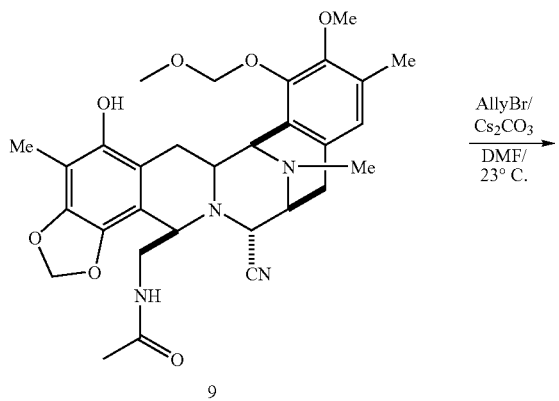

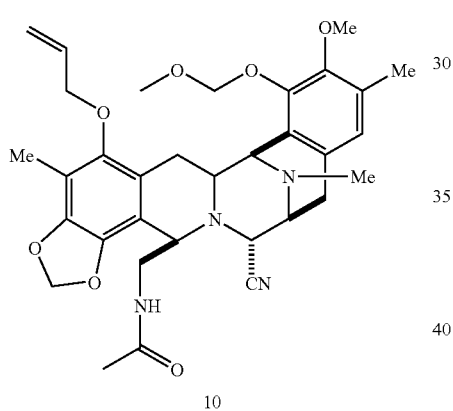

To a flask containing 9 (245 mg, 0.435 ml) in DMF, (4 ml), cesium carbonate (425 mg, 1.30 ml) and allyl bromide (376 ml, 4.35 ml) were added at 0° C. and the mixture was stirred at 23° C. for 1 h. The reaction was filtered though a pad of celite and partitioned between $CH_2Cl_2$ (25 ml) and $H_2O$ (10 ml). The organic phase was dried (sodium sulphate) and concentrated at reduced pressure to afford a residue that was purified by flash column chromatography ($SiO_2$, $CHCl_3$:ethyl acetate 1:2) to give 10 as a yellow oil. (113 mg, 43%).

Rf: 0.36 (hexane:ethyl acetate 1:5)

$^1$H NMR (300 MHz, CDCl$_3$): δ 6.74 (s, 1H), 6.3-6.0 (m, 1H), 5.94 (d, 1H), 5.87 (d, 1H), 5.43-5.36 (m, 2 h), 5.22 (s, 2 h), 5.00 (m, 1H), 4.22 (m, 1H), 4.17-4.01 (m, 1H), 3.98 (m, 2 h), 3.71-3.67 (m, 1H), 3.69 (s, 3H), 3.62-3.51 (m, 3H), 3.58 (s, 3H), 3.39-3.37 (m, 1H), 3.31-3.26 (m, 3H), 3.09 (dd, 1H), 2.56 (d, 1H), 2.36 (s, 3H), 2.21 (s, 3H), 2.11 (s, 3H), 2.24-2.10 (m, 1H), 1.82-1.73 (m, 1H), 1.24 (bs, 3H)

$^{13}$C NMR (75 MHz, CDCl$_3$): δ 169.4, 148.8, 148.3, 139.1, 133.7, 130.9, 130.3, 125.2, 120.2, 117.7, 113.1, 112.6, 101.3, 99.3, 74.1, 59.7, 59.3, 57.8, 57.0, 56.1, 56.1, 55.2, 41.6, 41.0, 40.9, 29.7, 26.3, 22.5, 15.6, 9.3

ESI-MS m/z: Calcd. for $C_{33}H_{40}N_4O_7$: 604.7. Found (M+H)$^+$: 605.3.

Example 40

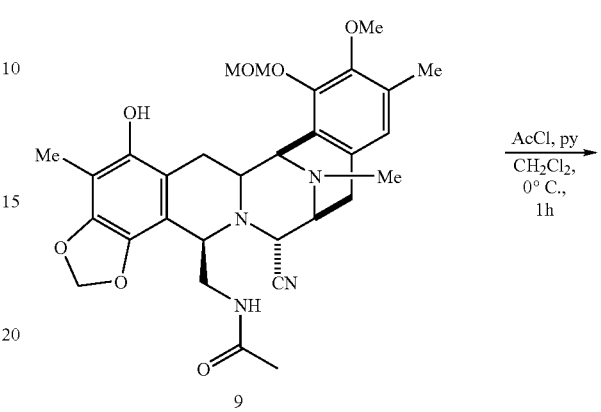

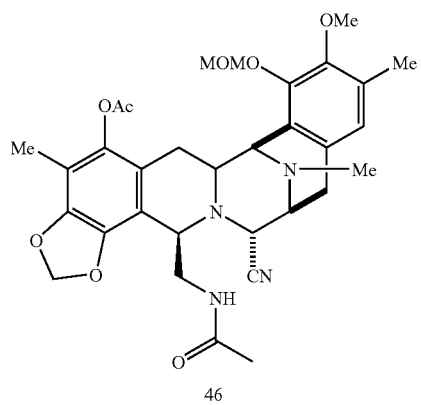

To a solution of 9 (22 mg, 0.039 ml) in $CH_2Cl_2$ (0.2 ml), acetyl chloride (2.79 ml, 0.039 ml) and pyridine (3.2 ml, 0.039 ml) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure to afford 46 (22 mg, 93%) as a white solid.

Rf: 0.4 (hexane:ethyl acetate 1:5).

$^1$H NMR (300 MHz, CDCl$_3$). δ 6.74 (s, 1H), 5.97 (d, J=0.9 Hz, 1H), 5.91 (d, J=0.9 Hz, 1H), 5.12 (d, J=5.7 Hz, 2 h), 5.04 (d, J=5.7 Hz, 1H) 4.90 (t, J=6 Hz, 1H), 4.17 (d, J=2.7 Hz, 1H), 4.05 (d, J=2.7 Hz, 1H), 4.01 (bs, 1H), 3.71 (s, 3H), 3.57 (s, 3H), 3.50-3.44 (m, 2 h), 3.38-3.36 (m, 1H), 3.30-3.26 (m, 1H), 3.00 (dd, J$_1$=7.8 Hz, J$_2$=18.0 Hz, 1H), 2.79 (d, J=12.9 Hz, 1H), 2.60 (d, J=18.0 Hz, 1H), 2.35 (s, 3H), 2.32 (s, 3H), 2.21 (s, 3H), 2.00 (s, 3H), 1.68 (dd, J$_1$=11.7 Hz, J$_2$=15.6 Hz, 1H).

ESI-MS m/z: Calcd. for $C_{32}H_{38}N_4O_8$: 606.67. Found $(M+H)^+$: 607.3.

ESI-MS m/z: Calcd. for $C_{30}H_{34}N_4O_7$: 562.61. Found $(M+H)^+$: 563.3.

Example 41

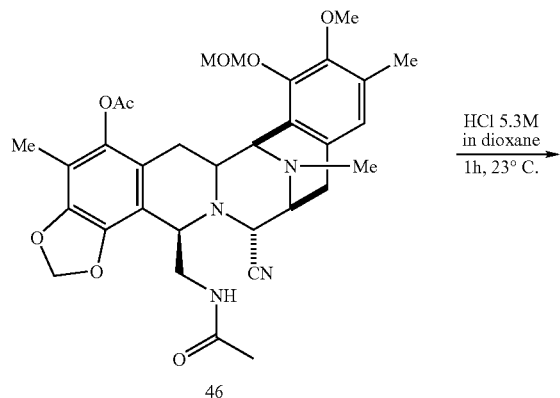

46

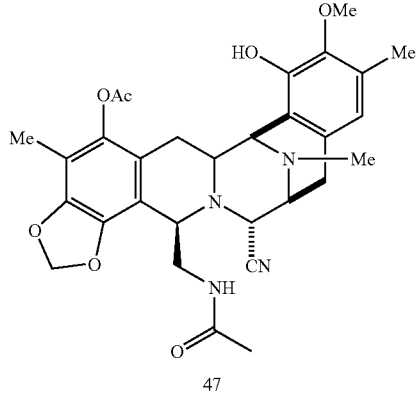

47

To a solution of 46 (8 mg, 0.013 ml) in dioxane (0.1 ml), 5.3N HCl/dioxane (0.5 ml) was added and the reaction was stirred at 23° C. for 1 h. Then, the solution was diluted with $CH_2Cl_2$ (5 ml) and washed with 0.1 N HCl (3 ml). The organic layer was dried over sodium sulphate, filtered, and the solvent was eliminated under reduced pressure to afford 47 (5 mg, 70%) as a white solid.

Rf: 0.4 (hexane:ethyl acetate 1:5).

$^1$H NMR (300 MHz, CDCl$_3$). δ 6.51 (s, 1H), 5.97 (d, J=1.2 Hz, 1H), 5.91 (d, J=1.2 Hz, 1H), 4.97 (bs, 1H), 4.11 (bs, 1H), 4.04-4.02 (m, 2 h), 3.75 (s, 3H),), 3.65 (d, J=2.1 Hz, 2 h), 3.56-3.30 (m, 2 h), 3.04 (dd, $J_1$=7.5 Hz, $J_2$=18 Hz, 1H), 2.80 (d, J=14.4 Hz, 1H), 2.59 (d, J=18.3 Hz, 1H), 2.33 (s, 3H), 2.24 (s, 3H), 2.00 (s, 3H), 1.76 (dd, $J_1$=12.0 Hz, $J_2$=15.9 Hz, 1H), 1.33 (s, 3H), 1.25 (s, 3H).

Example 42

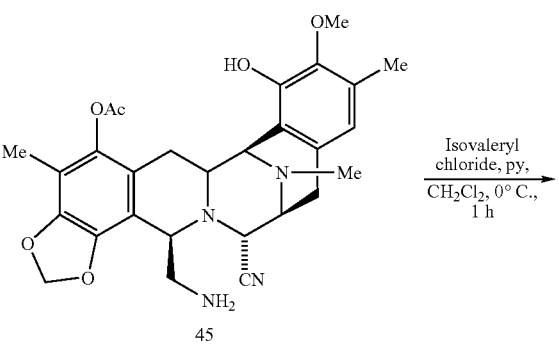

45

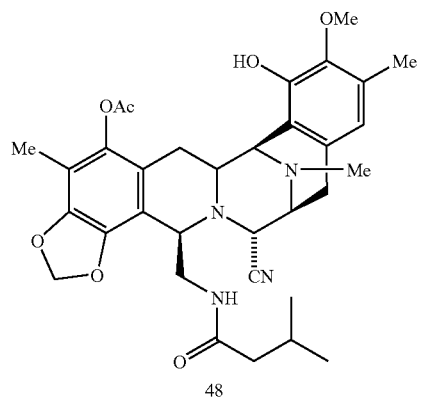

48

To a solution of 45 (10 mg, 0.0192 ml) in $CH_2Cl_2$ (0.3 ml), isovaleryl chloride (2.34 ml, 0.0192 ml) and pyridine (1.55 ml, 0.0192 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography (SiO$_2$, Hex: ethyl acetate 1:2) to afford 48 (11 mg, 95%) as a white solid.

Rf: 0.12 (Hex: ethyl acetate 1:2).

$^1$H NMR (300 MHz, CDCl$_3$): δ 6.50 (s, 1H), 5.98 (d, J=1.5 Hz, 1H), 5.91 (d, J=1.5 Hz, 1H), 5.75 (s, 1H), 5.02 (t, J=5.4 Hz, 1H), 4.10 (d, J=1.5 Hz, 1H), 4.06 (d, J=2.7 Hz, 1H), 4.02 (d, J=2.7 Hz, 1H), 3.77 (s, 3H), 3.76-3.71 (m, 1H), 3.86-3.28 (m, 3H), 3.04 (dd, $J_1$=8.1 Hz, $J_2$=18.3 Hz, 1H), 2.78 (d, J=15.9 Hz, 1H), 2.55 (d, J=18 Hz, 1H), 2.32 (s, 6H), 2.26 (s, 3H), 1.98 (s, 3H), 1.84-1.68 (m, 2 h), 1.36 (d, J=7.2 Hz, 2 h), 0.69 (d, J=6.6 Hz, 3H), 0.62 (d, J=6.6 Hz, 3H).

ESI-MS m/z: Calcd. for $C_{33}H_{40}N_4O_7$: 604.69. Found (M+H)$^+$: 605.3.

Example 43

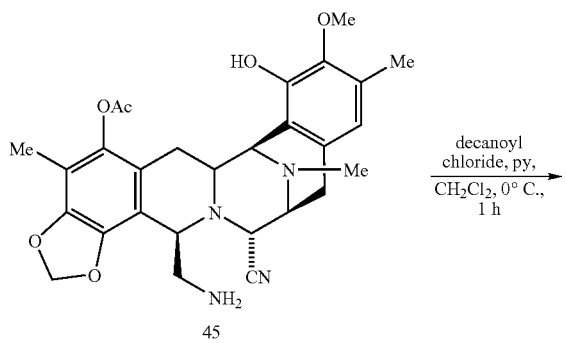

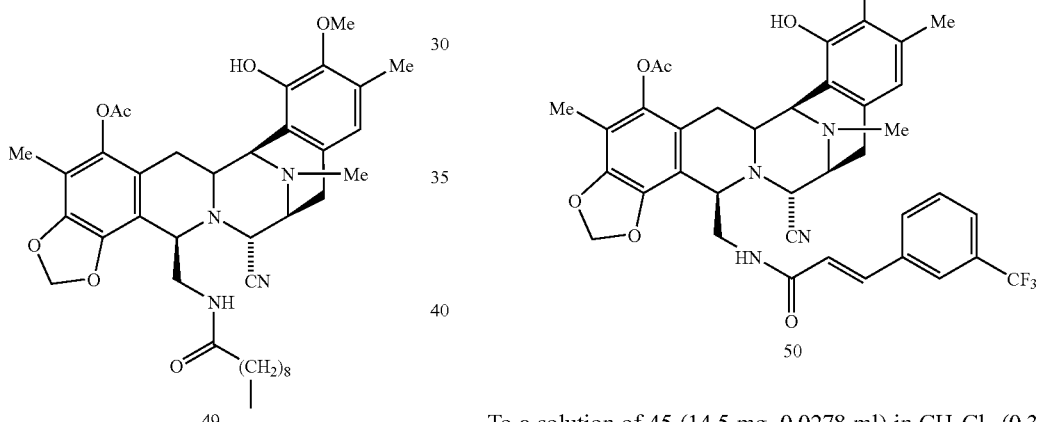

To a solution of 45 (10 mg, 0.0192 ml) in $CH_2Cl_2$ (0.3 ml), isovaleryl chloride (3.98 ml, 0.0192 ml) and pyridine (1.55 ml, 0.0192 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 1:2) to afford 49 (12.4 mg, 96%) as a white solid.

Rf: 0.7 (ethyl acetate:methanol 10:1).

$^1$H NMR (300 MHz, CDCl$_3$): δ 6.50 (s, 1H), 5.98 (d, J=1.5 Hz, 1H), 5.91 (d, J=1.5 Hz, 1H), 5.73 (s, 1H), 5.08 (t, J=5.4 Hz, 1H), 4.10 (d, J=1.5 Hz, 1H), 4.05 (m., 1H), 4.01 (m, 1H), 3.76 (s, 3H), 3.65-3.61 (m, 1H), 3.40-3.27 (m, 3H), 3.03 (dd, J$_1$=8.1 Hz, J$_2$=18.6 Hz, 1H), 2.78 (d, J=13.2 Hz, 1H), 2.57 (d, J=18.3 Hz, 1H), 2.32 (s, 3H), 2.31 (s, 3H), 2.25 (s, 3H), 1.99 (s, 3H), 1.79 (dd, J$_1$=12.0 Hz, J$_2$=16.5 Hz, 1H), 1.73-1.42 (m, 4H), 1.33-1.18 (m, 10H), 1.03 (m, 2 h), 0.87 (t, J=6.6 Hz, 3H).

ESI-MS m/z: Calcd. for $C_{38}H_{50}N_4O_7$: 674.83. Found (M+H)$^+$: 675.5.

Example 44

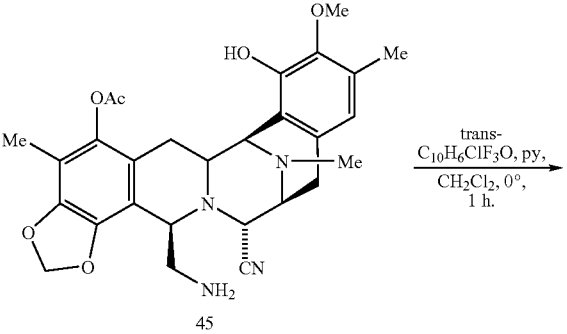

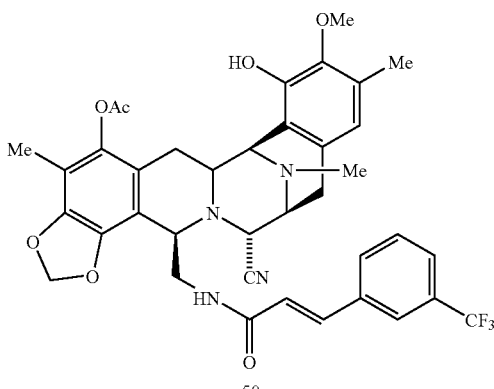

To a solution of 45 (14.5 mg, 0.0278 ml) in $CH_2Cl_2$ (0.3 ml), trans-3-trifluoromethyl cinnamoyl chloride (4.76 ml, 0.0278 ml) and pyridine (2.25 ml, 0.0278 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 1:1) to afford 50 (18.7 mg, 94%) as a white solid.

Rf: 0.64 (ethyl acetate:methanol 5:1).

$^1$H NMR (300 MHz, CH$_3$OD). δ 7.74-7.55 (m, 4H), 7.23 (d, J=16.0 Hz, 1H), 6.34 (s, 1H), 6.12 (d, J=16.0 Hz, 1H), 6.07 (d, J=0.9 Hz, 1H), 5.96 (d, J=0.9 Hz, 1H), 4.39 (d, J=2.4 Hz, 1H), 4.07-4.05 (m, 1H), 3.81 (bs, 1H), 3.46-3.51 (m, 3H), 3.42 (s, 3H), 3.09 (br d, J=12.0 Hz, 1H), 2.94-2.85 (m, 2 h), 2.74 (d, J=18.3 Hz, 1H), 2.38 (s, 3H), 2.23 (s, 3H), 2.02 (s, 3H), 1.80 (s, 3H), 1.84-1.75 (m, 1H).

$^{13}$C NMR (75 MHz, CDCl$_3$)): δ 168.7, 165.3, 146.5, 144.7, 142.6, 140.6, 138.0, 135.9, 131.0, 130.9, 129.1, 128.6, 125.8, 125.7, 124.5, 124.4, 122.7, 121.2, 117.8, 116.5, 113.0, 112.0, 101.7, 60.4, 59.1, 56.5, 56.4, 55.6, 55.3, 41.8, 40.3, 26.6, 25.1, 20.3, 15.4, 9.3.

ESI-MS m/z: Calcd. for $C_{38}H_{37}F_3N_4O_7$: 718.72. Found (M+H)+: 719.3.

Example 45

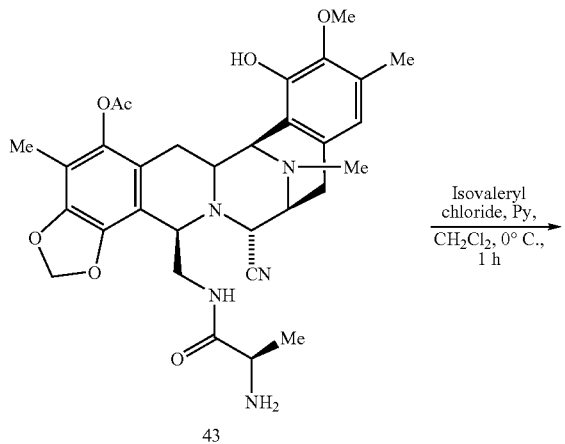

43

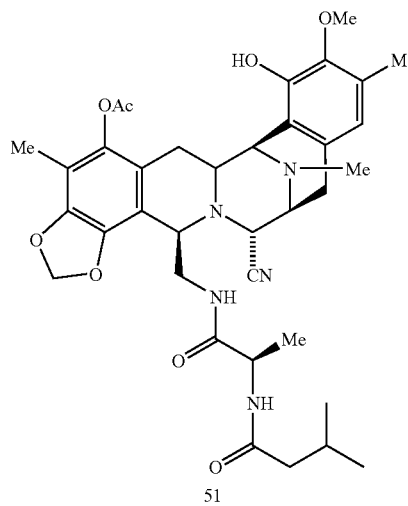

51

To a solution of 43 (33 mg, 0.0557 ml) in $CH_2Cl_2$ (0.4 ml), isovaleryl chloride (6.79 ml, 0.0557 ml) and pyridine (4.5 ml, 0.0557 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 1:2) to afford 51 (34 mg, 91%) as a white solid.

Rf: 0.09 (Hex: ethyl acetate 1:2).

$^1$H NMR (300 MHz, $CDCl_3$): δ 6.46 (s, 1H), 6.10 (bs, 1H), 5.99 (d, J=0.9 Hz, 1H), 5.90 (d, J=0.9 Hz, 1H), 5.30 (t, J=6.0 Hz, 1H), 4.10-4.05 (m, 3H), 3.81 (bs, 1H), 3.74 (s, 3H), 3.54 (bs, 1H), 3.38-3.36 (m, 1H), 3.29-3.21 (m, 1H), 3.00 (dd, $J_1$=8.0 Hz, $J_2$=18.0 Hz, 1H), 2.25 (s, 3H), 2.20 (s, 3H), 2.00 (s, 3H), 1.95-1.90 (m, 3H), 0.87 (d, J=6.6 Hz, 6H), 0.76 (d, J=6.0 Hz, 3H).

ESI-MS m/z: Calcd. for $C_{36}H_{45}N_5O_8$: 675.77. Found (M+H)+: 676.3.

Example 46

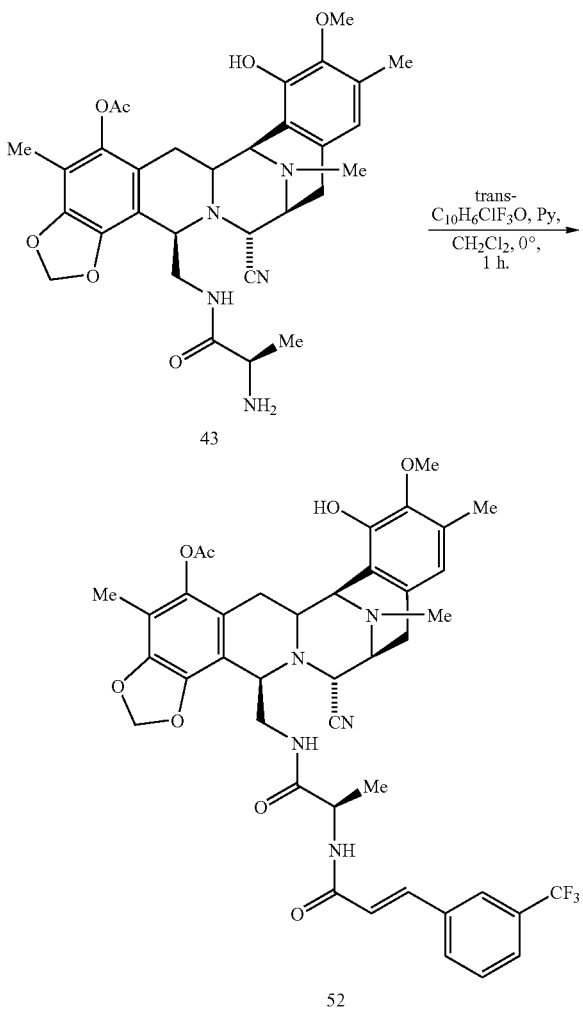

To a solution of 43 (33 mg, 0.0557 ml) in $H_2Cl_2$ (0.4 ml), trans-3-trifluoromethyl cinnamoyl chloride (9.52 ml, 0.0557 ml) and pyridine (4.5 ml, 0.0557 ml) were added at 0° C. The reaction mixture was stirred for 1 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 1:2) to afford 52 (40 mg, 92%) as a white solid.

Rf: 0.21 (hexane:ethyl acetate 1:2).

$^1$H NMR (300 MHz, $CD_3OD$). δ 7.74-7.47 (m, 4H), 6.49 (s, 1H), 6.40 (d, J=15.6 Hz, 1H), 6.00 (d, J=1.5 Hz, 1H), 5.90 (d, J=1.5 Hz, 1H), 5.47 (t, J=6 Hz, 1H), 4.12-4.09 (m, 3H), 3.93 (bs, 1H), 3.71 (s, 3H), 3.59-3.58 (m, 1H), 3.38 (d, J=7.8 Hz, 1H), 3.29 (d, J=12.0 Hz, 1H), 3.00 (dd, $J_1$=8.1 Hz, $J_2$=18.3 Hz, 1H), 2.79-2.78 (m, 1H), 2.65 (d, J=18.3 Hz, 1H), 2.29 (s, 6H), 2.28 (s, 3H), 2.22 (s, 3H), 1.84-1.80 (m, 1H), 0.85-0.84 (m, 3H).

$^{13}$C NMR (75 MHz, $CDCl_3$) δ 171.9, 168.8, 164.4, 146.9, 144.6, 143.0, 140.5, 140.5, 139.3, 135.7, 131.1, 131.0, 129.4, 129.1, 126.0, 124.1, 124.0, 122.4, 121.1, 120.7, 120.6, 117.7, 116.9, 112.8, 112.0, 101.6, 60.6, 59.3, 57.1, 56.3, 55.9, 55.2, 49.0, 41.7, 49.9, 26.5, 25.1, 20.2, 18.4, 15.7, 9.3.

ESI-MS m/z: Calcd. for $C_{41}H_{42}F_3N_5O_8$: 789.8. Found $(M+H)^+$: 790.3.

Example 47

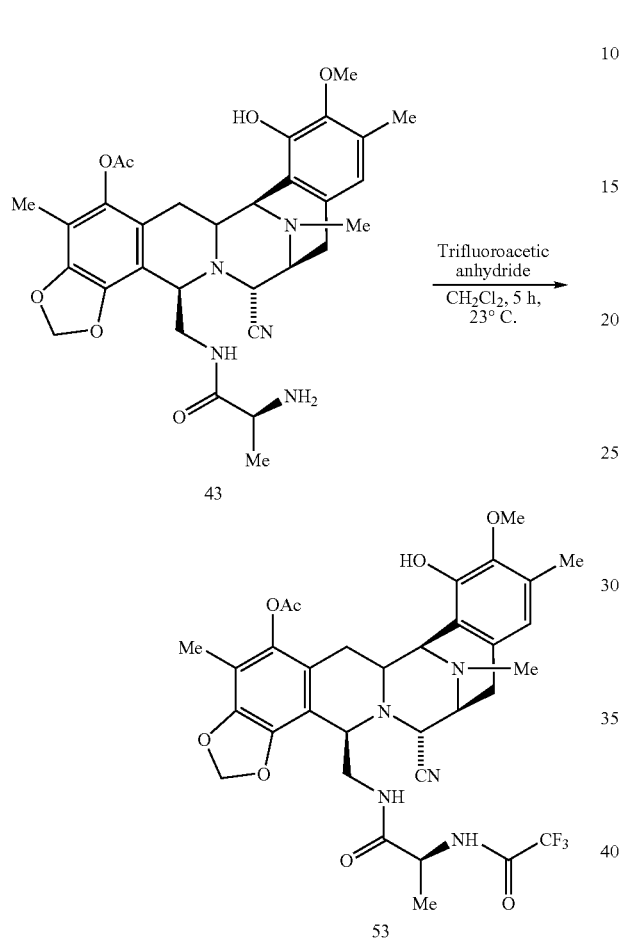

To a solution of 43 (10 mg, 0.0169 ml) in $CH_2Cl_2$ (0.2 ml) trifluoroacetic anhydride (2.38 μl, 0.0169 ml) was added at 23° C. The reaction mixture was stirred for 5 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 3:2) to afford 53 (10.7 mg, 93%) as a white solid.

Rf: 0.57 (ethyl acetate:methanol 5:1).

$^1$H NMR (300 MHz, $CDCl_3$) δ 6.45 (s, 1H), 6.00 (d, J=1.2 Hz, 1H), 5.90 (d, J=1.2 Hz, 1H), 5.87 (bs, 1H), 5.32 (bs, 1H), 4.12 (d, J=2.1 Hz, 1H), 4.08 (d, J=1.8 Hz, 1H), 3.78-3.56 (m, 3H), 3.72 (s, 3H), 3.40 (d, J=8.1 Hz, 1H), 3.25 (d, J=9.3 Hz, 1H), 3.00 (dd, $J_1$=8.4 Hz, $J_2$=18.0 Hz, 1H), 2.77 (dd, $J_1$=2.1 Hz, $J_2$=15.9 Hz, 1H), 2.68 (d, J=18.6 Hz, 1H), 2.30 (s, 3H), 2.28 (s, 3H), 2.22 (s, 3H), 2.00 (s, 3H), 1.75 (dd, $J_1$=11.4 Hz, $J_2$=15.9 Hz, 1H), 0.69 (d, J=6.3 Hz, 3H).

$^{13}$C NMR (75 MHz, $CDCl_3$) δ 170.1, 168.6, 156.0, 147.0, 144.6, 143.0, 140.6, 140.4, 131.0, 129.4, 120.9, 120.7, 117.6, 116.8, 112.4, 112.1, 101.6, 60.5, 59.0, 57.1, 56.3, 55.6, 55.2, 48.7, 41.6, 39.4, 26.5, 24.9, 20.2, 17.8, 15.4, 9.2.

ESI-MS m/z: Calcd. for $C_{33}H_{36}F_3N_5O_8$: 687.63. Found $(M+H)^+$: 688.66.

Example 48

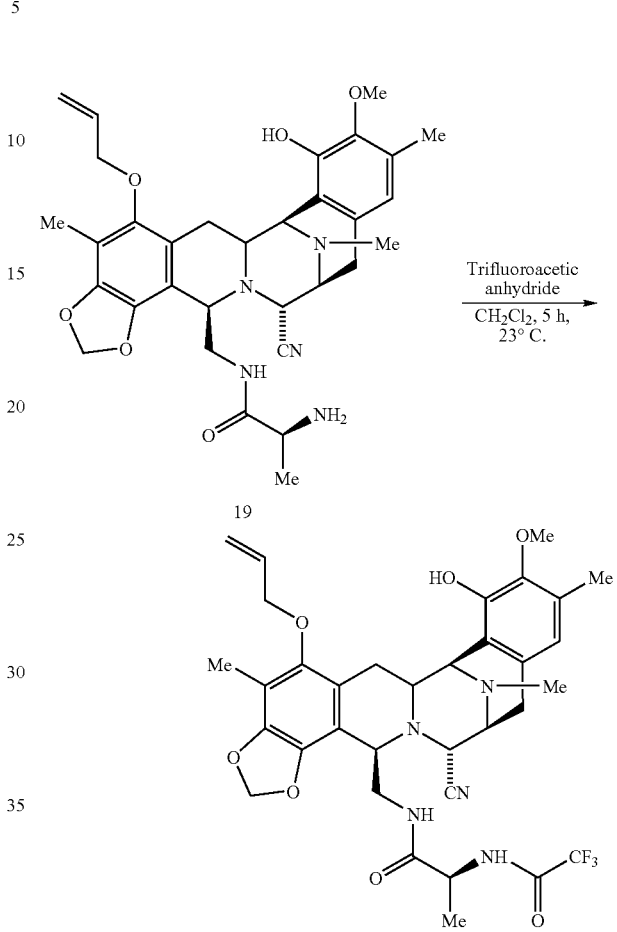

To a solution of 19 (11 mg, 0.0169 ml) in $CH_2Cl_2$ (0.2 ml) trifluoroacetic anhydride (2.38 ml, 0.0169 ml) was added at 23° C. The reaction mixture was stirred for 5 h and then, the solution was diluted with $CH_2Cl_2$ (5 ml) and washed with 0.1 N HCl (3 ml). The organic layer was dried over sodium sulphate, filtered, and the solvent was eliminated under reduced pressure. The residue was purified by flash column chromatography ($SiO_2$, Hex: ethyl acetate 3:2) to afford 54 (10.7 mg, 93%) as a white solid.

Rf: 0.6 (ethyl acetate:methanol 5:1).

$^1$H NMR (300 MHz, $CDCl_3$) δ 7.33 (d, J=6.3 Hz, 1H), 6.45 (s, 1H), 6.04 (m, 1H), 5.95 (d, J=1.5 Hz, 1H), 5.84 (d, J=1.5 Hz, 1H), 5.32 (m, 2 h), 5.21 (m, 1H), 4.11 (m, 4H), 3.73 (s, 3H), 3.64 (m, 2 h), 3.51 (m, 1H), 3.37 (d, J=7.8 Hz, 1H), 3.22 (m, 2 h), 3.03 (dd, 1H, $J_1$=8.1 Hz, $J_2$=18.3 Hz, 1H), 2.60 (d, J=18.3 Hz, 1H), 2.29 (s, 3H), 2.24 (s, 3H), 2.08 (s, 3H), 1.86 (dd, $J_1$=12 Hz, $J_2$=16.2 Hz, 1H), 0.82 (d, J=7.2 Hz, 3H).

$^{13}$C NMR (75 MHz, $CDCl_3$) δ 170.0, 156.0, 148.4, 147.1, 144.3, 143.0, 138.7, 133.8, 130.5, 129.4, 120.6, 120.4, 117.6, 117.5, 117.0, 113.5, 112.5, 112.4, 101.1, 74.1, 66.8, 60.4, 59.3, 56.9, 56.6, 56.3, 55.4, 48.7, 41.6, 40.1, 26.2, 25.0, 17.6, 15.4, 9.1.

ESI-MS m/z: Calcd. for $C_{35}H_{39}F_3N_5O_7$: 685.69. Found (M+H)$^+$: 686.3.

Example 49

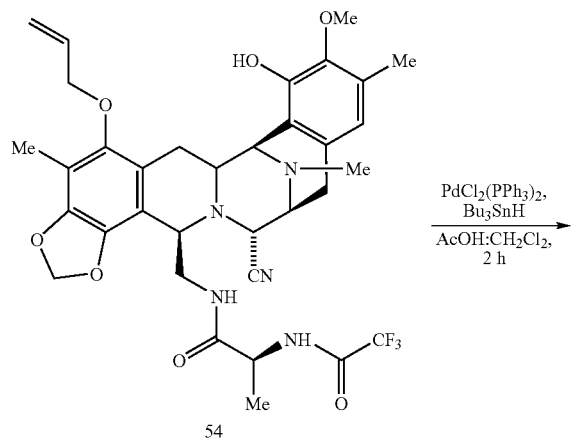

54

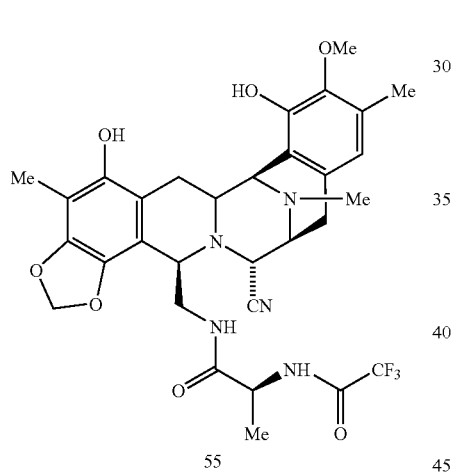

55

To a solution of 54 (100 mg, 0.415 ml) in CH$_2$Cl$_2$ (4 ml), acetic acid (40 ml), (PPh$_3$)$_2$PdCl$_2$ (8.4 mg, 0.012 ml) and Bu$_3$SnH (157 ml, 0.56 ml) were added at 23° C. After stirring at that temperature for 2 h the reaction was poured into a pad of flash column (SiO$_2$, gradient Hex to hexane:ethyl acetate 2:1) to afford 55 (90 mg, 96%) as a white solid.

Rf: 0.6 (hexane:ethyl acetate 1:2).

$^1$H NMR (300 MHz, CDCl$_3$) δ 7.55 (d, J=7.2 Hz, 1H), 6.45 (s, 1H), 5.90 (d, J=1.2 Hz, 1H), 5.82 (d, J=1.2 Hz, 1H), 5.37 (t, J=6.0 Hz, 1H), 4.15 (d, J=2.1 Hz, 1H), 4.04 (d, J=1.8 Hz, 1H), 3.70 (s, 3H), 3.66-3.53 (m, 2 h), 3.37-3.31 (m, 2 h), 3.19-3.15 (d, J=11.7 Hz, 1H), 3.08-3.00 (m, 2 h), 2.56 (d, J=18.3 Hz, 1H), 2.30 (s, 3H), 2.24 (s, 3H), 2.04 (s, 3H), 1.91 (dd, J$_1$=12.0 Hz, J$_2$=15.6 Hz, 1H), 0.84 (d, J=6.9 Hz, 3H).

$^{13}$C NMR (75 MHz, CDCl$_3$) δ 170.1, 156.3, 147.3, 144.9, 144.4, 143.3, 136.7, 130.7, 129.3, 120.6, 117.6, 117.4, 114.4, 112.1, 107.7, 101.0, 85.8, 60.5, 59.3, 56.5, 56.4, 56.2, 55.2, 48.9, 41.6, 40.9, 25.7, 25.3, 18.0, 15.6, 8.7.

ESI-MS m/z: Calcd. for $C_{32}H_{35}F_3N_5O_7$: 645.63. Found (M+H)$^+$: 646.2.

Example 50

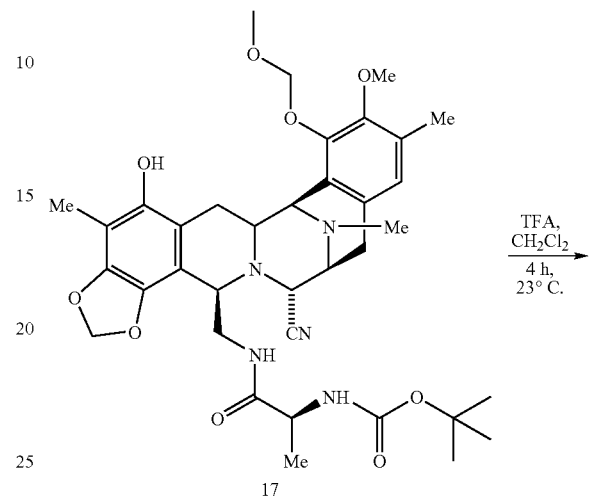

17

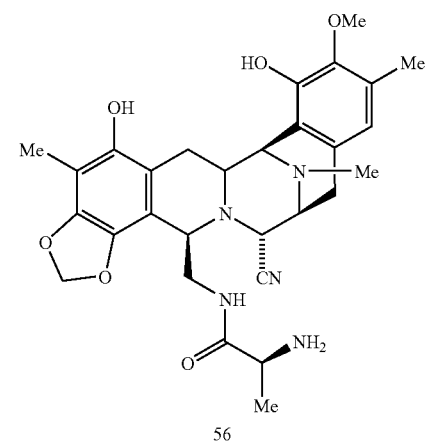

56

To a solution of 17 (200 mg, 0.288 ml) in CH$_2$Cl$_2$ (1.44 ml), trifluoroacetic acid (888 ml, 11.53 ml) was added and the reaction mixture was stirred for 4 h at 23° C. The reaction was quenched at 0° C. with saturated aqueous sodium bicarbonate (60 ml) and extracted with ethyl acetate (2×70 ml). The combined organic layers were dried (sodium sulphate) and concentrated in vacuo to afford 56 (147 mg, 93%) as a white solid that was used in subsequent reactions with no further purification.

Rf: 0.19 (ethyl acetate:methanol 5:1).

$^1$H NMR (300 MHz, CD$_3$OD). δ 6.48 (s, 1H), 5.88, d, J=0.9 Hz, 1H), 5.81 (d, J=0.9 Hz, 1H), 4.35 (d, J=2.4 Hz, 1H), 4.15 (d, J=1.8 Hz, 1H), 3.99-3.98 (m, 1H), 3.70 (s, 3H), 3.52-2.96 (m, 7H), 2.68 (d, J=18.3 Hz, 1H), 2.24 (s, 3H), 2.23 (s, 3H), 2.06 (s, 3H), 1.85 (dd, J$_1$=11.7 Hz, J$_2$=15.6 Hz, 1H), 0.91 (d, J=6.6 Hz, 3H).

$^{13}$C NMR (75 MHz, CD$_3$OD): δ 173.2, 149.1, 145.6, 144.9, 138.0, 132.2, 130.6, 121.4, 119.6, 117.4, 114.3, 109.2, 102.5, 82.3, 60.4, 58.4, 58.3, 57.8, 56.6, 50.1, 42.3, 41.6, 27.8, 26.2, 19.5, 15.5, 9.8.

ESI-MS m/z: Calcd. for $C_{29}H_{35}N_5O_6$: 549.62. Found (M+H)$^+$: 550.3.

Example 51

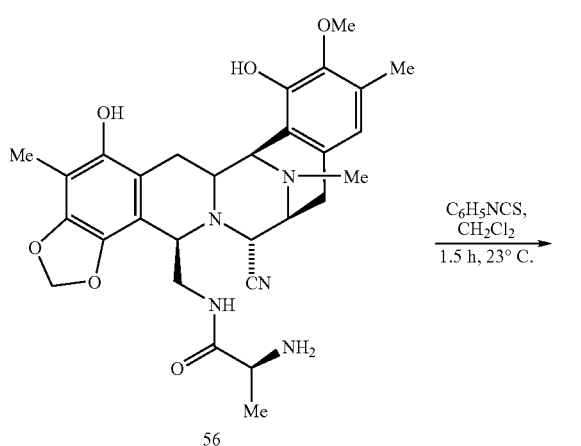

To a solution of 56 (10 mg, 0.018 ml) in $CH_2Cl_2$ (0.4 ml), phenyl isothiocyanate (13 ml, 0.109 ml) was added and the reaction was stirred at 23° C. for 1.5 h. The mixture was concentrated in vacuo and the residue was purified by flash column chromatography (SiO$_2$, gradient Hexane to 1:1 hexane:ethyl acetate) to afford 57 (8 mg, 65%) as a white solid.

Rf: 0.57 (ethyl acetate:methanol 10:1).

$^1$H NMR (300 MHz, CDCl$_3$): δ 7.88 (bs, 1H), 7.41-7.36 (m, 2 h), 7.27-7.22 (m, 1H), 7.02-7.00 (d, J=7.8 Hz, 2 h), 6.71 (d, J=−7.2 Hz, 1H), 6.31 (s, 1H), 6.17 (bs, 1H), 5.93 (d, J=−1.2 Hz, 1H), 5.83 (d, J=1.2 Hz, 1H), 5.55 (bs, 1H), 5.20-5.17 (m, 1H), 4.16 (d, J=1.8 Hz, 1H), 4.05 (bs, 1H), 4.02 (d, J=2.4 Hz, 1H), 3.79 (s, 3H), 3.75-3.71 (m, 1H), 3.35 (d, J=7.8 Hz, 1H), 3.28-3.19 (m, 2 h), 3.12-2.97 (m, 2 h), 2.50 (d, J=18.3 Hz, 1H), 2.32 (s, 3H), 2.21 (s, 3H), 2.15-2.09 (dd, J$_1$=11.4 Hz, J$_2$=15.9 Hz, 1H), 1.95 (s, 3H), 0.88 (d, J=6.9 Hz, 3H).

$^{13}$C NMR (75 MHz, CDCl$_3$): δ 178.5, 171.7, 147.2, 145.0, 144.3, 143.3, 137.0, 135.7, 130.6, 130.4, 129.6, 127.5, 124.3, 120.6, 117.7, 117.2, 115.3, 112.1, 108.3, 100.9, 60.9, 59.5, 56.7, 56.5, 56.2, 55.2, 54.1, 41.7, 41.1, 26.3, 25.4, 18.5, 15.8, 9.0.

ESI-MS m/z: Calcd. for $C_{36}H_{40}N_6O_6S$: 684.81. Found (M+H)$^+$: 685.3.

Example 52

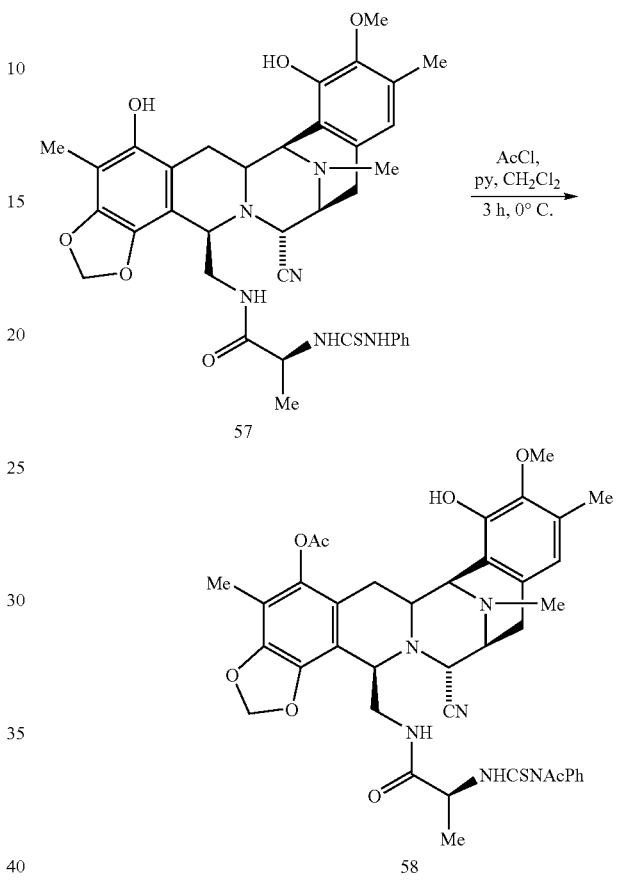

To a solution of 57 (45 mg, 0.065 ml) in $CH_2Cl_2$ (0.5 ml), acetyl chloride (4.67 ml, 0.065 ml) and pyridine (5.3 ml, 0.065 ml) were added at 0° C. The reaction mixture was stirred for 3 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography (RP-18, CH$_3$CN: H$_2$O 40:60) to afford 58 (14 mg, 28%) as a white solid.

Rf: 0.34 (CH$_3$CN: H$_2$O 7:15).

$^1$H NMR (300 MHz, CDCl$_3$). δ 11.90 (d, J=6.6 Hz, 1H), 7.45-7.40 (m, 3H), 7.18-7.15 (m, 2 h), 6.58 (s, 1H), 6.00 (d, J=1.2 Hz, 1H), 5.89 (d, J=1.2 Hz, 1H), 5.70 (s, 1H), 5.37 (t, J=4.8 Hz, 1H), 4.48 (m, 1H), 4.23 (bs, 1H), 4.07 (bs, 2H), 3.85-3.75 (m, 1H), 3.70 (s, 3H), 3.46-3.41 (m, 2 h), 3.24-3.20 (m, 1H), 3.00-2.95 (m, 1H), 2.87-2.75 (m, 1H), 2.31 (s, 3H), 2.28 (s, 3H), 2.24 (s, 3H), 2.00 (s, 3H), 1.85 (dd, J$_1$=11.4 Hz, J$_2$=15.6 Hz, 1H), 1.66 (s, 3H), 0.82 (d, J=6.0 Hz, 3H).

$^{13}$C NMR (75 MHz, CDCl$_3$)): δ 182.6, 174.3, 171.0, 146.6, 144.6, 142.7, 142.3, 140.7, 140.2, 131.3, 129.8, 129.3, 128.9, 128.8, 121.5, 120.4, 117.3, 116.6, 112.8, 112.0, 111.3, 101.5, 60.5, 59.0, 57.6, 56.2, 55.9, 55.3, 55.1, 41.6, 39.4, 27.8, 26.5, 24.8, 20.2, 17.1, 15.5, 9.3.

ESI-MS m/z: Calcd. for $C_{40}H_{44}N_6O_8S$: 768.88. Found (M+H)$^+$: 769.2.

Example 53

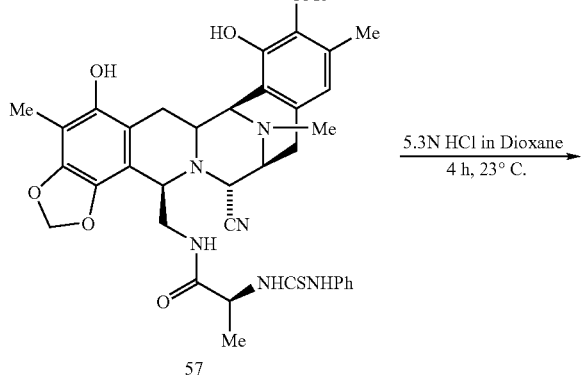

57

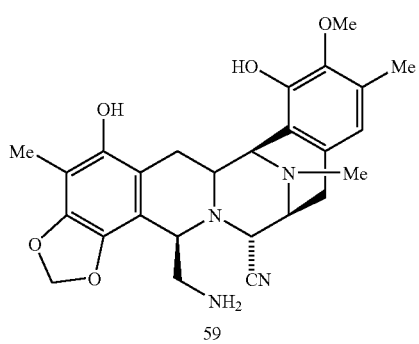

59

A solution of 57 (130 mg, 0.189 ml) in dioxane (1 ml), 5.3N HCl/dioxane (1.87 ml) was added and the reaction was stirred at 23° C. for 4 h. Then, CH$_2$Cl$_2$ (15 ml) and H$_2$O (10 ml) were added to this reaction and the organic layer was decanted. The aqueous phase was basified with saturated aq sodium bicarbonate (60 ml) (pH=8) at 0° C. and then, extracted with ethyl acetate (2×50 ml). The combined organic extracts were dried (sodium sulphate), and concentrated in vacuo to afford 59 (63 mg, 70%) as a white solid.

Rf: 0.15 (ethyl acetate:methanol 5:1).

$^1$H NMR (300 MHz, CDCl$_3$). δ 6.67 (s, 1H), 5.99 (d, J=0.9 Hz, 1H), 5.91 (d, J=1.2 Hz, 1H), 5.10 (bs, 1H), 4.32 (d, J=7.2 Hz, 1H), 4.25 (dd, J$_1$=3.6 Hz, J$_2$=9.3 Hz, 1H), 3.7 (s, 3H), 3.71-3.64 (m, 2 h), 3.50 (dd, J$_1$=2.4 Hz, J$_2$=15.9 Hz, 1H), 3.42-3.37 (m, 2h), 3.16 (dd, J$_1$=3.6 Hz, J$_2$=12.9 Hz, 1H), 2.57 (dd, J$_1$=9.3 Hz, J$_2$=12.9 Hz, 1H), 2.27 (s, 3H), 2.11 (s, 3H), 1.91 (dd, J$_1$=12.0 Hz, J$_2$=15.9 Hz, 1H).

ESI-MS m/z: Calcd. for $C_{26}H_{30}N_4O_5$: 478.5. Found (M+H)$^+$: 479.3.

Example 54

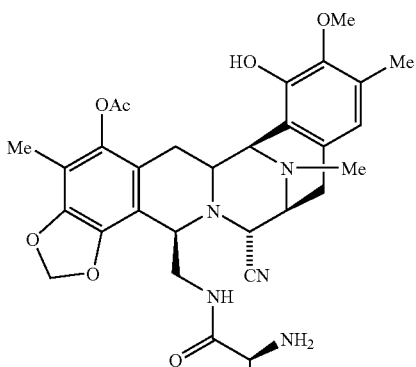

43

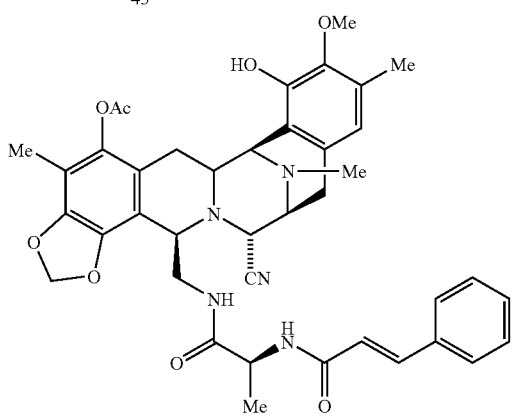

60

A solution of 43 (20 mg, 0.0338 mmol) in CH$_2$Cl$_2$ (0.3 ml), cinnamoyl chloride (5.63 mg, 0.0338 mmol) and pyridine (2.73 ml, 0.0338 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 60 (22 mg, 90%) as a white solid.

Rf: 0.56 (EtOAc:MeOH 5:1).

$^1$H NMR (300 MHz, CDCl$_3$). 7.51 (s, 1H), 7.50-7.47 (m, 2H), 7.36-7.35 (m, 2H), 6.43 (s, 1H), 6.36 (brd, J=15.9 Hz, 2H), 6.01 (d, J=1.5 Hz, 1H), 5.90 (brd, J=1.5 Hz, 2H), 5.42 (t, J=6.0 Hz 1H), 4.12-4.07 (m, 3H), 3.96-3.95 (m, 1H), 3.73 (bs, 3H), 3.58 (bs, 2H), 3.39 (d, J=8.7 Hz, 1H), 3.25 (d, J=11.7 Hz, 1H), 3.0 (dd, J$_1$=7.5 Hz, J$_2$=17.7 Hz, 1H), 2.78 (d, J=15.9 Hz, 1H), 2.67 (d, J=16.5 Hz, 1H), 2.29 (s, 6H), 2.23 (s, 3H), 1.99 (s, 3H), 1.82 (dd, J$_1$=11.4 Hz, J$_2$=15.6 Hz, 1H), 0.83 (d, J=6.0 Hz, 3H).

$^{13}$C NMR (75 MHz, CDCl$_3$)): δ. 172.0, 165.0, 146.9, 144.6, 143.1, 141.0, 140.5, 134.8, 131.0, 129.7, 129.1, 128.8, 127.8, 125.5, 123.8, 123.0, 121.1, 120.5, 117.7, 116.9, 112.8, 112.0, 101.9, 60.6, 59.2, 57.1, 56.4, 55.9, 55.3, 48.8, 41.7, 40.0, 26.5, 25.1, 20.3, 18.5, 15.7, 9.3.

ESI-MS m/z: Calcd. for $C_{40}H_{43}N_5O_8$: 721.8. Found (M+H)+: 722.3.

Example 55

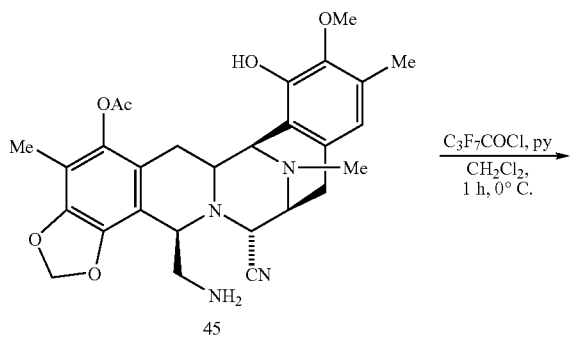

45

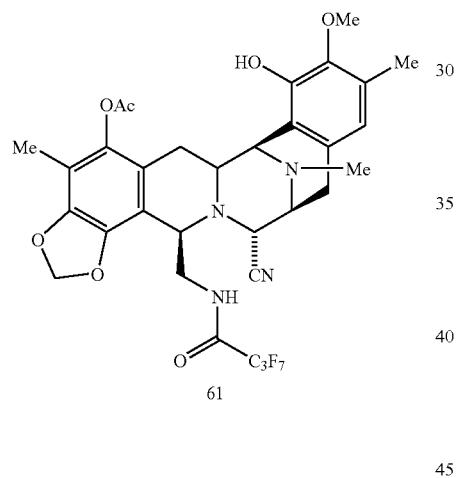

61

A solution of 45 (19 mg, 0.0364 mmol) in $CH_2Cl_2$ (0.3 ml), heptafluorobutyryl chloride (5.44 ml, 0.0364 mmol) and pyridine (2.95 ml, 0.0364 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc: MeOH 20:1) to afford 61 (11.7 mg, 45%) as a white solid.

Rf: 0.76 (EtOAc:MeOH 5:1).

$^1$H NMR (300 MHz, $CDCl_3$) δ 6.46 (s, 1H), 6.12 (bs, 1H), 5.98 (d, J=1.2 Hz, 1H), 5.93 (d, J=1.2 Hz, 1H), 5.72 (bs, 1H), 4.13-4.11 (m, 2H), 4.0 (d, J=2.4 Hz, 1H), 3.98-3.96 (m, 1H), 3.73 (s, 3H), 3.39 (d, J=7.5 Hz, 1H), 3.39-3.28 (m, 2H), 3.09 (dd, $J_1$=8.1 Hz, $J_2$=18.0 Hz, 1H), 2.80 (d, J=16.2 Hz, 1H), 2.46 (d, J=18.3 Hz, 1H), 2.32 (s, 6H), 2.21 (s, 3H), 1.99 (s, 3H), 1.80 (dd, $J_1$=12.0 Hz, $J_2$=16.2 Hz, 1H).

ESI-MS m/z: Calcd. for $C_{32}H_{31}F_7N_4O_7$: 716.6. Found (M+H)+: 717.2.

Example 56

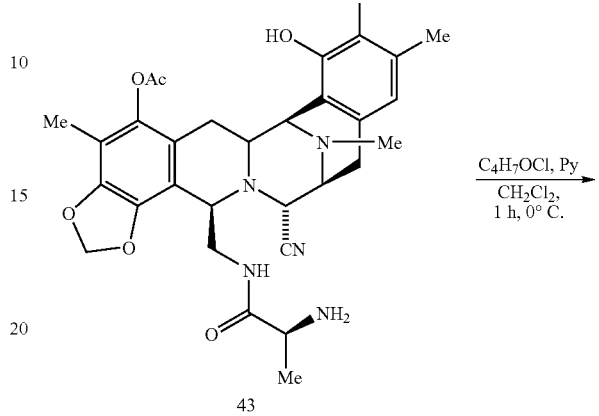

43

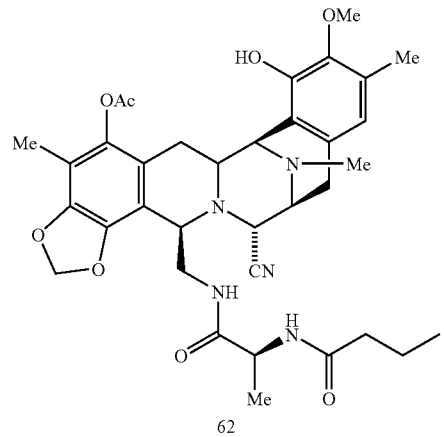

62

A solution of 43 (24 mg, 0.04 mmol) in $CH_2Cl_2$ (0.3 ml), butyryl chloride (4.15 ml, 0.04 mmol) and pyridine (3.28 ml, 0.04 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc:MeOH 20:1) to afford 62 (24 mg, 90%) as a white solid.

Rf: 0.35 (EtOAc:MeOH 5:1).

$^1$H NMR (300 MHz, $CDCl_3$) δ 6.47 (s, 1H), 6.10 (d, J=6.5 Hz, 1H), 6.0 (d, J=1.5 Hz, 1H), 5.91 (d, J=1.5 Hz, 1H), 5.86 (bs, 1H), 5.31 (d, J=6.9 Hz, 1H), 4.11-4.06 (m, 3H), 3.85-3.81 (m, 1H), 3.75 (s, 3H), 3.59-3.53 (m, 2H), 3.38 (d, J=7.5 Hz, 1H), 3.27-3.22 (m, 1H), 3.0 (dd, $J_1$=7.8 Hz, $J_2$=17.4 Hz, 1H), 2.79 (d, J=15.3 Hz, 1H), 2.63 (d, J=17.7 Hz, 1H), 2.31 (s, 3H), 2.0 (s, 3H), 1.80 (dd, $J_1$=12.0 Hz, $J_2$=15.9 Hz, 1H), 1.58 (q, J=7.2 Hz, 2H), 0.89 (t, J=7.2 Hz, 3H), 0.76 (d, J=6.6 Hz, 3H).

ESI-MS m/z: Calcd. for $C_{35}H_{43}N_5O_8$: 661.64. Found $(M+H)^+$: 662.3

Example 57

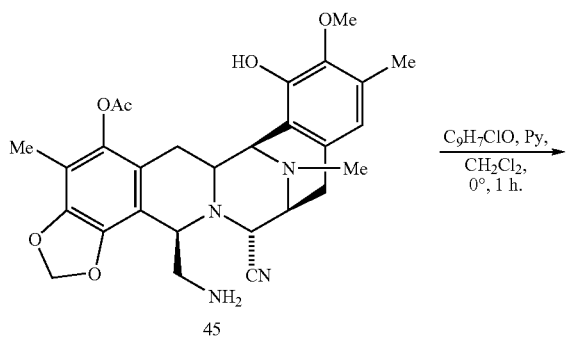

ESI-MS m/z: Calcd. for $C_{37}H_{38}N_4O_7$: 650.72. Found $(M+H)^+$: 651.2.

Example 58

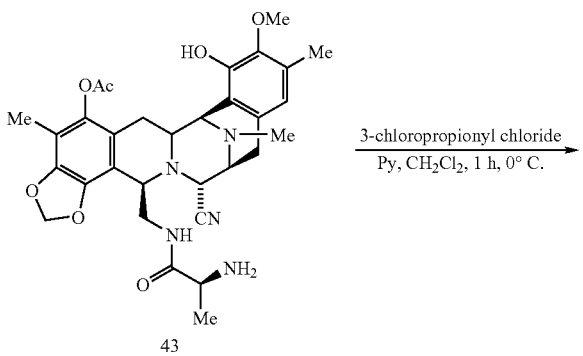

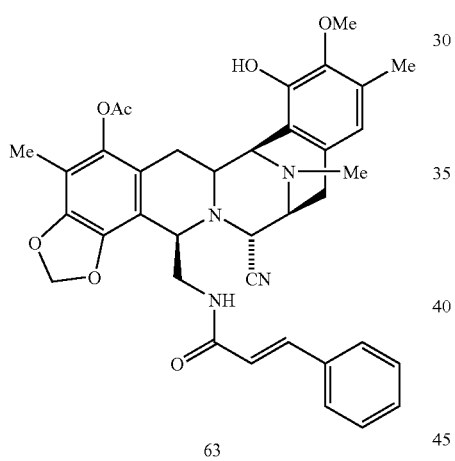

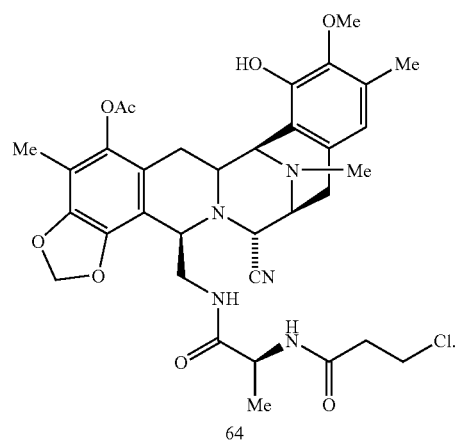

A solution of 43 (19 mg, 0.0364 mmol) in $CH_2Cl_2$ (0.3 ml), cinnamoyl chloride (6.06 mg, 0.0364 mmol) and pyridine (2.95 ml, 0.0364 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc: MeOH 20:1) to afford 63 (20.1 mg, 85%) as a white solid.

Rf: 0.65 (EtOAc:MeOH 5:1).

$^1$H NMR (300 MHz, $CDCl_3$) δ 7.39-7.29 (m, 5H), 6.42, (s, 1H), 6.01 (d, J=1.5 Hz, 1H), 5.92 (d, J=1.5 Hz, 1H), 5.73 (bs, 1H), 5.24 (t, J=6.8 Hz, 1H), 4.12-4.08 (m, 3H), 3.66-3.64 (m, 2H), 3.58 (bs, 3H), 3.36 (d, J=8.7 Hz, 1H), 3.29 (d, J=12.0 Hz, 1H), 2.98 (dd, $J_1$=8.1 Hz, $J_2$=18 Hz, 1H), 2.33 (s, 6H), 2.29 (s, 3H), 2.01 (s, 3H), 1.84 (dd, $J_1$=12.0 Hz, $J_2$=15.9 Hz, 1H).).

A solution of 43 (20 mg, 0.0338 mmol) in $CH_2Cl_2$ (0.3 ml), 3-chloropropionyl chloride (3.22 ml, 0.0338 mmol) and pyridine (2.73 ml, 0.0338 mmol) were added at 0° C. The reaction mixture was stirred for 1 h and then, the solution was diluted with $CH_2Cl_2$ (10 ml) and washed with 0.1 N HCl (5 ml). The organic layer was dried over sodium sulphate, filtered, and the solvent was eliminated under reduced pressure. The residue was purified by flash column chromatography ($SiO_2$, EtOAc: MeOH 20:1) to afford 64 (20.5 mg, 89%) as a white solid.

Rf: 0.32 (EtOAc:Hexane 5:1).

$^1$H NMR (300 MHz, $CDCl_3$) 6.48 (s, 3H), 6.28 (m, 1H), 5.99 (d, J=1.2 Hz, 1H), 5.91 (d, J=1.2 Hz, 1H), 5.86 (bs, 1H), 5.31 (m, 1H), 4.08-4.07 (m, 3H), 3.75 (s, 3H), 3.72-3.53 (m, 5H), 3.39 (d, J=8.1 Hz, 1H), 3.24 (d, J=12.0 Hz, 1H), 3.00 (dd, $J_1$=8.1 Hz, $J_2$=18.0 Hz, 1H), 2.79 (d, J=13.5 Hz, 1H), 2.50 (t,

J=6.3 Hz, 2H), 2.32 (s, 3H), 2.28 (s, 3H), 2.25 (s, 3H), 2.0 (s, 3H), 1.79 (dd, J$_1$=12.3 Hz, J$_2$=14.8 Hz, 1H), 0.81 (d, J=6.3 Hz, 3H).

ESI-MS m/z: Calcd. for C$_{32}$H$_{38}$N$_4$O$_7$: 590.67. Found (M+H)$^+$: 591.2.

Example 59

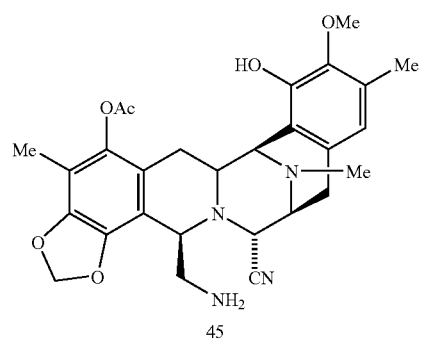

Example 60

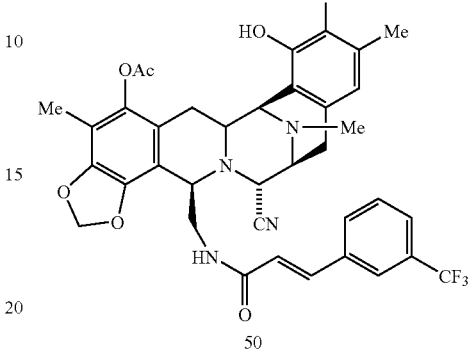

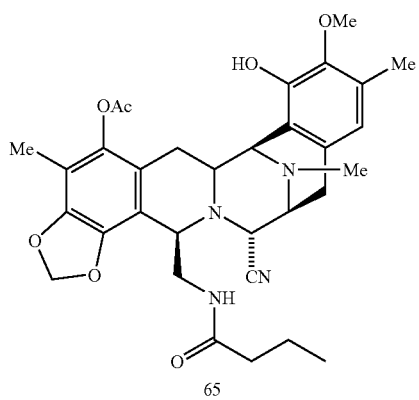

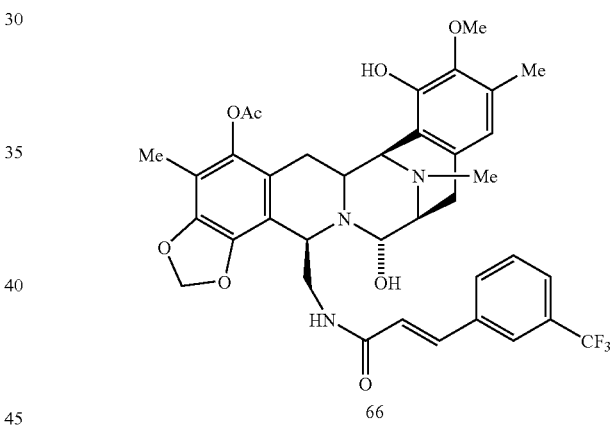

A solution of 43 (19 mg, 0.0364 mmol) in CH$_2$Cl$_2$ (0.3 ml), butyryl chloride (3.78 ml, 0.0364 mmol) and pyridine (2.95 ml, 0.0364 mmol) were added at 0° C. The reaction mixture was stirred for 1 h and then, the solution was diluted with CH$_2$Cl$_2$ (10 ml) and washed with 0.1 N HCl (5 ml). The organic layer was dried over sodium sulphate, filtered, and the solvent was eliminated under reduced pressure. The residue was purified by flash column chromatography (SiO$_2$, EtOAc:MeOH 20:1) to afford 64 (19 mg, 87%) as a white solid.

Rf: 0.60 (EtOAc:MeOH 5:1).

$^1$H NMR (300 MHz, CDCl$_3$) 6.50 (s, 1H), 5.98 (d, J=1.5 Hz, 1H), 5.91 (d, J=1.5 Hz, 1H), 5.75 (s, 1H), 5.01 (t, J=6.4 Hz, 1H), 4.10-4.09 (m, 1H), 4.06 (d, J=2.1 Hz, 1H), 4.03-4.02 (m, 1H), 3.76 (s, 3H), 3.67-3.60 (m, 1H), 3.42-3.35 (m, 2H), 3.29 (d, J=12.0 Hz, 1H), 3.02 (dd, J$_1$=7.8 Hz, J$_2$=17.7 Hz, 1H), 2.79 (d, J=14.1 Hz, 1H), 2.56 (d, J=18.3 Hz, 1H), 2.32 (s, 3H), 2.31 (s, 3H), 2.25 (s, 3H), 1.78 (dd, J$_1$=12.0 Hz, J$_2$=15.9 Hz, 1H), 1.63 (s, 3H), 1.53-1.46 (m, 2H), 1.28-1.16 (m, 2H), 0.68 (t, J=7.2 Hz, 3H).

To a solution of 50 (31.7 mg, 0.044 mmol) in CH$_3$CN/H$_2$O (1.5 ml/0.5 ml), AgNO$_3$ (225 mg, 1.32 mmol) was added and the reaction was stirred at 23° C. for 17 h. Then brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 66 (16 mg, 51%) as a white solid.

Rf: 0.26 (EtOAc:MeOH 5:1).

$^1$H NMR (300 MHz, CDCl$_3$) δ 7.66-7.42 (m, 4H), 7.20 (bs, 1H), 6.44 (s, 1H), 5.97 (b, J=1.2 Hz, 1H), 5.90 (d, J=1.2 Hz, 1H), 5.76 (bs, 1H), 5.28 (bs, 1H), 4.54 (bs, 1H), 4.43 (bs, 1H), 4.00 (bs, 1H), 3.68-3.57 (m, 4H), 3.47 (d, J=3.3 Hz, 1H), 3.40 (d, J=11.7 Hz, 1H), 3.17 (d, J=6.9 Hz, 1H), 2.92 (dd, J$_1$=8.1 Hz, J$_2$=17.7 Hz, 1H), 2.74 (d, J=17.1 Hz, 1H), 2.48 (d, J=18.6 Hz, 1H), 2.32 (s, 6H), 2.28 (s, 3H), 1.99 (s, 3H), 1.76 (dd, J$_1$=12.0 Hz, J$_2$=16.2 Hz, 1H).

ESI-MS m/z: Calcd. for $C_{37}H_{38}F_3N_3O_8$: 709. Found ($M^+$-17): 692.3.

Example 61

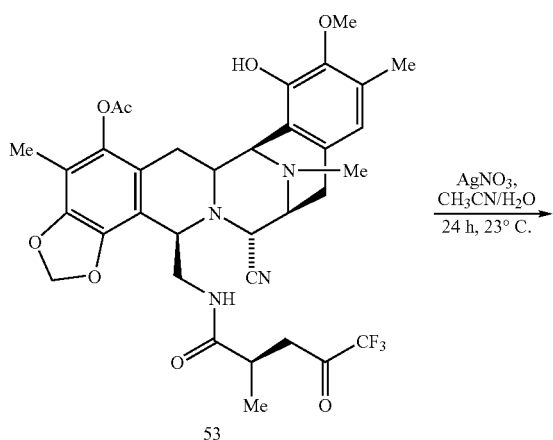

ESI-MS m/z: Calcd. for $C_{32}H_{37}F_3N_4O_9$: 678.66. Found ($M^+$-17): 661.2.

Example 62

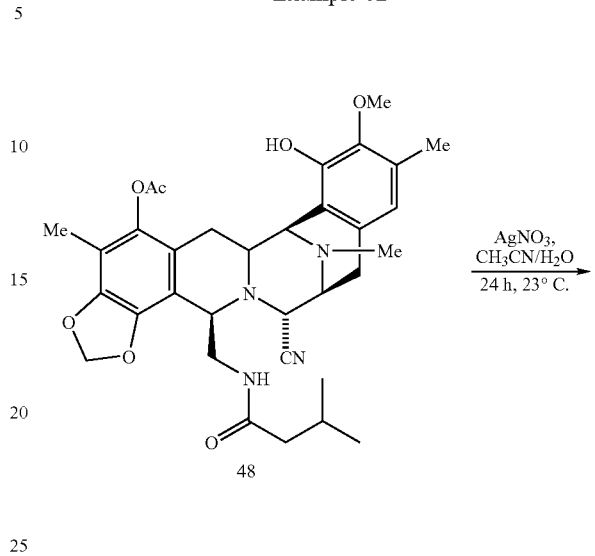

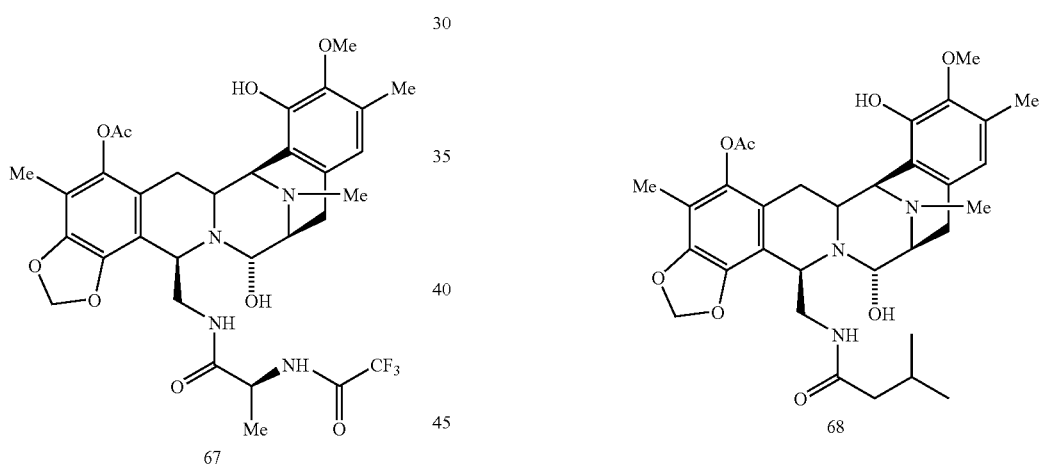

To a solution of 53 (57 mg, 0.0828 mmol) in $CH_3CN/H_2O$ (1.5 mL/0.5 ml), $AgNO_3$ (650 mg, 3.81 mmol) was added and the reaction was stirred at 23° C. for 24 h. Then, brine (10 ml) and Aq sat $NaHCO_3$ (10 ml) were added at 0° C. and the mixture was stirred for 15 min, filtered through a pad of celite and washed with $CH_2Cl_2$ (20 ml). The solution was decanted and the organic layer was dried and concentrated in vacuo. The residue was purified by flash column chromatography ($SiO_2$, EtOAc:MeOH 5:1) to afford 67 (28 mg, 50%) as a white solid.

Rf: 0.28 (EtOAc:MeOH 10:1).

$^1$H NMR (300 MHz, $CDCl_3$) d 6.47 (s, 1H), 5.97 (s, 1H), 5.88 (s, 1H), 5.35 (bs, 1H), 4.51 (bs, 1H), 4.41 (bs, 1H), 4.12-4.05 (m, 1H), 4.00 (d, J=2.7 Hz, 1H), 3.77 (s, 3H), 3.64 (bs, 1H), 3.46 (d, J=3.3 Hz, 1H), 3.34 (d, J=11.4 Hz, 1H), 3.18 (d, J=7.5 Hz, 1H), 2.95 (dd, $J_1$=8.4 Hz, $J_2$=18.3 Hz, 1H), 2.70 (d, J=15.6 Hz, 1H), 2.48 (d, J=17.7 Hz, 1H), 2.28 (s, 3H), 2.27 (s, 3H), 2.26 (s, 3H), 1.98 (s, 3H), 1.68 (dd, $J_1$=12 Hz, $J_2$=15.6 Hz, 1H), 0.86 (d, J=6.3 Hz, 3H).

To a solution of 48 (32 mg, 0.0529 mmol) in $CH_3CN/H_2O$ (1.5 ml/0.5 ml), $AgNO_3$ (270 mg, 1.58 mmol) was added and the reaction was stirred at 23° C. for 24 h. Then, brine (10 ml) and Aq sat $NaHCO_3$ (10 ml) were added at 0° C. and the mixture was stirred for 15 min, filtered through a pad of celite and washed with $CH_2Cl_2$ (20 ml). The solution was decanted and the organic layer was dried and concentrated in vacuo. The residue was purified by flash column chromatography ($SiO_2$, EtOAc:MeOH 5:1) to afford 68 (18 mg, 56%) as a white solid.

Rf: 0.40 (EtOAc:MeOH 5:1).

$^1$H NMR (300 MHz, $CDCl_3$) δ 6.50 (s, 1H), 5.95 (d, J=1.2 Hz, 1H), 5.88 (d, J=1.2 Hz, 1H), 5.23 (d, J=6.9 Hz, 1H), 4.45 (d, J=3.3 Hz, 1H), 4.38 (s, 1H), 4.01 (d, J=2.4 Hz, 1H), 3.78 (m, 1H), 3.77 (s, 3H), 3.41-3.37 (m, 1H), 3.17-3.15 (m, 1H), 2.96 (dd, $J_1$=7.8 Hz, $J_2$=18.0 Hz, 1H), 2.70 (d, J=15.3 Hz, 1H), 2.40 (d, J=18.0 Hz, 1H), 2.30 (s, 6H), 2.27 (s, 3H), 1.76-1.65 (m, 1H), 1.35-1.25 (m, 2H), 0.89-0.82 (m, 1H), 0.69 (d, J=6.6 Hz, 3H), 0.58 (d, J=6.6 Hz, 3H)

Example 63

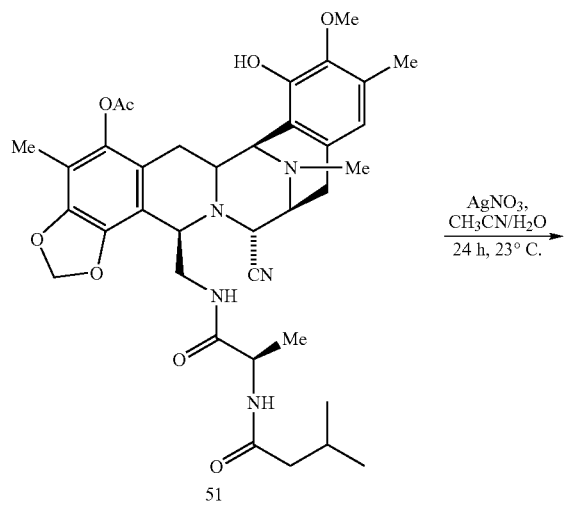

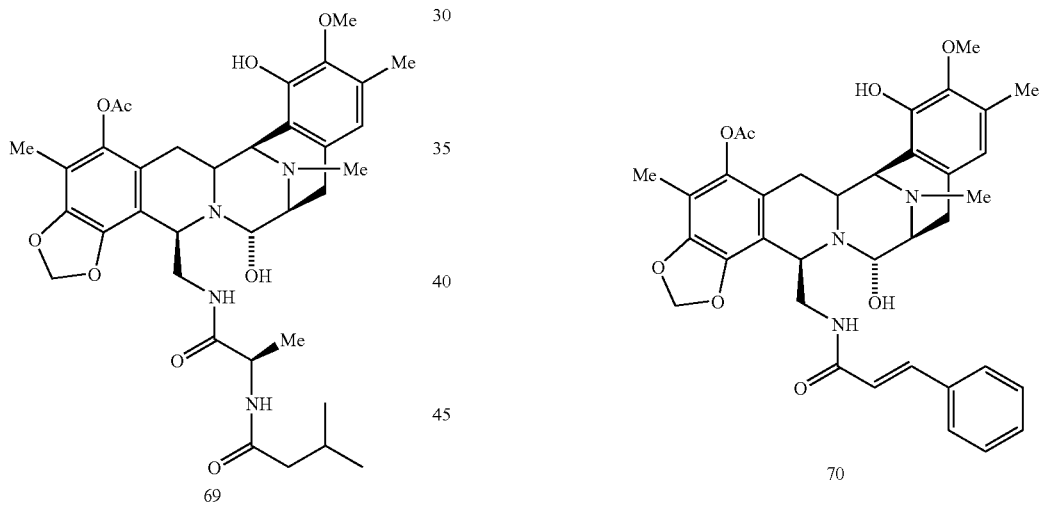

To a solution of 51 (27 mg, 0.04 mmol) in CH$_3$CN/H$_2$O (1.5 ml/0.5 ml), AgNO$_3$ (204 mg, 1.19 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 69 (10 mg, 38%) as a white solid.

Rf: 0.38 (EtOAc:MeOH 5:1).

$^1$H NMR (300 MHz, CDCl$_3$) δ 6.48 s, 1H), 6.16 (bs, 1H), 5.98 (d, J=1.5 Hz, 1H), 5.89 (d, J=1.5 Hz, 1H), 5.33 (t, J=6.0 Hz, 1H), 4.50 (m, 1H), 4.40 (m, 1H), 4.11-4.09 (m, 1H), 4.00 (d, J=2.6 Hz, 1H), 3.78 (s, 3H), 3.41-3.32 (m, 3H), 3.18 (d, J=8.4 Hz, 1H), 2.94 (dd, J$_1$=8.4 Hz, J$_2$=18.3 Hz, 1H), 2.70 (d, J=14.4 Hz, 1H), 4.45 (d, J=18.3 Hz, 1H), 2.31 (s, 3H), 2.28 (s, 3H), 2.27 (s, 3H), 2.04 (s, 3H), 2.00-1.86 (m, 3H), 1.73 (m, 1H), 0.87 (d, J=6.3 Hz, 6H).

Example 64

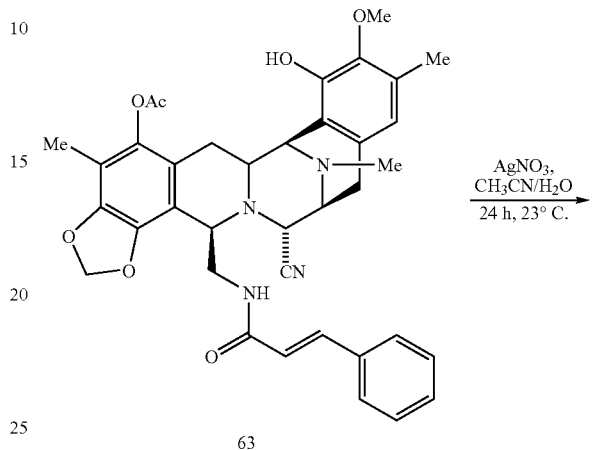

To a solution of 63 (15 mg, 0.023 mmol) in CH$_3$CN/H$_2$O (1.5 ml/0.5 ml), AgNO$_3$ (118 mg, 0.691 mmol) was added and the reaction was stirred at 23° C. for 24 h. Then, brine (10 ml) and Aq sat NaHCO$_3$ (10 ml) were added at 0° C. and the mixture was stirred for 15 min, filtered through a pad of celite and washed with CH$_2$Cl$_2$ (20 ml). The solution was decanted and the organic layer was dried and concentrated in vacuo. The residue was purified by flash column chromatography (SiO$_2$, EtOAc:MeOH 5:1) to afford 70 (20.1 mg, 85%) as a white solid.

Rf: 0.43 (EtOAc:MeOH 5:1).

$^1$H NMR (300 MHz, CDCl$_3$) δ 7.38-7.28 (m, 5H), 6.48 (s, 1H), 5.98 (d, J=1.5 Hz, 1H), 5.91 (d, J=1.5 Hz, 1H), 5.75 (bs, 1H), 5.38 (brd, 1H), 5.30 (bs, 1H), 4.53 (m, 1H), 4.42 (m, 1H), 4.02 (d, J=2.7 Hz, 1H), 3.78-3.65 (m, 5H), 3.46-3.40 (m, 2H), 3.17 (d, J=7.8 Hz, 1H), 2.94 (dd, J$_1$=7.8 Hz, J$_2$=17.7 Hz, 1H), 2.73 (d, J=16.8 Hz, 1H), 2.45 (d, J=18.0 Hz, 1H), 2.31 (s, 6H), 2.28 (s, 3H), 1.97 (s, 3H), 1.77 (dd, $J_1$=12.0 Hz, $J_2$=15.3 Hz, 1H).

Example 65

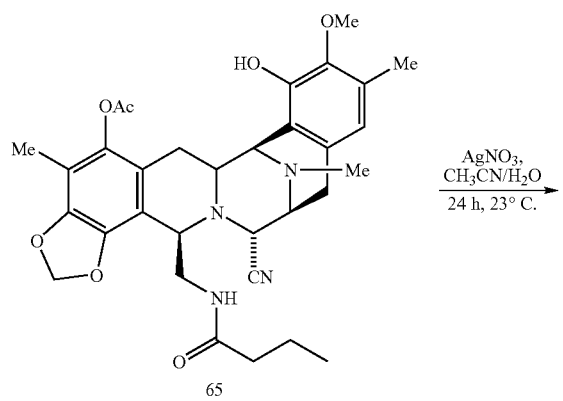

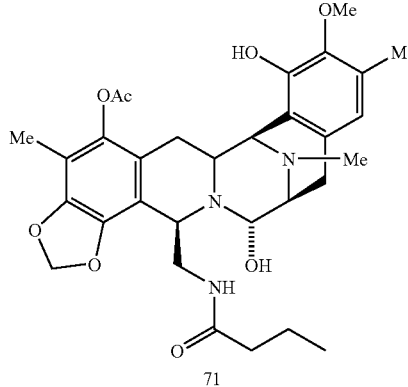

To a solution of 65 (25 mg, 0.042 mmol) in $CH_3CN/H_2O$ (1.5 ml/0.5 ml), $AgNO_3$ (215.56 mg, 1.269 mmol) was added and the reaction was stirred at 23° C. for 24 h. Then, brine (10 ml) and Aq sat $NaHCO_3$ (10 ml) were added at 0° C. and the mixture was stirred for 15 min. filtered through a pad of celite and washed with $CH_2Cl_2$ (20 ml). The solution was decanted and the organic layer was dried and concentrated in vacuo. The residue was purified by flash column chromatography ($SiO_2$, EtOAc:MeOH 5:2) to afford 71 (16 mg, 65%) as a white solid.

Rf: 0.0.5 (EtOAc:MeOH 5:2).

$^1$H NMR (300 MHz, $CDCl_3$) δ 6.50 (s, 1H), 5.95 (d, J=1.5 Hz, 1H), 5.78 (s, 1H), 5.19 (bs, 1H), 4.45 (d, J=3.3 Hz, 1H), 4.37 (bs, 1H), 4.11 (brd, J=4.8 Hz, 1H), 4.01 (d, J=2.1 Hz, 1H), 3.76 (s, 1H), 3.71-3.69 (m, 1H), 3.49-3.35 (m, 1H), 3.24 (d, J=13.5 Hz, 1H), 3.15 (d, J=9.3 Hz, 1H), 2.95 (dd, $J_1$=8.1 Hz, $J_2$=17.7 Hz, 1H), 2.70 (d, J=15.6 Hz, 1H), 2.40 (d, J=18.0 Hz, 1H), 2.31 (s, 3H), 2.29 (s, 3H), 2.26 (s, 3H), 1.96 (s, 3H), 1.75-1.66 (m, 1H), 1.52-1.17 (m, 2H), 0.66 (t, J=7.2 Hz, 3H).

Fermentation Procedures

Example A

Seed medium YMP3 containing 1% glucose; 0.25% beef extract; 0.5% bacto-peptone; 0.25% NaCl; 0.8% $CaCO_3$ was inoculated with 0.1% of a frozen vegetative stock of the microorganism, strain A2-2 of *Pseudomonas fluorescens*, and incubated on a rotary shaker (250 rpm) at 27° C. After 30 h of incubation, the seed culture was added to a agitated-vessel fermentor with a production medium composed of 2% dextrose; 4% mannitol, 2% dried brewer's yeast (Vitalevor® Biolux, Belgium); 1% $(NH_4)_2SO_4$; 0.04% $K_2HPO_4$; 0.8 KCl; 0.001% $FeCl_3$; 0.1% L-Tyr; 0.8% $CO_3Ca$; 0.05% PPG-2000; 0.2% anti-foam silicone (ASSAF-100, RHODIA UK). The sterilisation was carried out at 122° C. 30 minutes. The volume inoculated was a 2% (v/v). The temperature was 27° C. (0 to 16 h) and 24° C. from 16 h to final process (41 hours). The dissolve oxygen-pressure was upper to 25%. The pH was controlled at 6.0 with diluted sulphuric acid since 28 hours till final process. The overpressure was 0.5 bar. A 1% mannitol or sorbitol was added from 16 h to final process (for two days running) and 2% for three days fermentation-process.

After 41 or 64 hours, the fermentation broth must be extracted for recovery safracin B or KCN treatment in the clarified broth for recovery safracin B-cyano.

Example B

Obtention of safracin B cyano from the crude extract.

A clarification or filtration from the fermentation broth at pH 6 removes the solids. The clarified broth was adjusted a pH 9.5 with diluted sodium hydroxide and extracted twice with 2:1 (v/v) ethyl acetate, methylene chloride or butyl acetate. The extraction was carried out into an agitated-vessel during 20', the temperature of the mixture was maintained at 8 to 10° C. The two phases were separated by a liquid-liquid centrifuge. The organic phase was dried with sodium sulphate anhydrous or frozen and then filtered for removing ice. This organic phase (ethyl acetate layer) was evaporated until obtention of an oil-crude extract.

Example C

Obtention of safracin B cyano from the clarified broth.

A clarification or filtration from the fermentation broth at pH 6 removes the solids. The clarified broth was adjusted at pH 3.9 with concentrated acetic acid. 0.5 grams per litre of KCN are added to the clarified broth an incubated at 20° C. during 1 hour with agitation. Then, the temperature was decreased at 15° C. and the pH was adjusted at 9.5 with diluted sodium hydroxide and extracted with 2:1.5 (v/v) ethyl acetate. The extraction was carried out into an agitated-vessel during 20 minutes, the temperature of the mixture was maintained at 8 to 10° C. The two phases were separated by a liquid-liquid centrifuge. The organic phase was dried with sodium sulphate anhydrous. This organic phase (ethyl acetate layer) was evaporated until obtention of an oil-crude extract. This extract was purified by flash column chromatography ($SiO_2$, gradient 20:1 to 10: to 5:1 ethyl acetate:methanol) to afford quantitatively compound 2 as a light yellow solid.

Rf: 0.55 (ethyl acetate:methanol 5:1); .$t_R$=19.9 min [HPLC, Delta Pack C4, 5 μm, 300 A, 150×3 mm, λ=215 nm, flow=0.7 ml/min, temp=50° C., grad.: $CH_3CN$-aq. NaOAc (10 mM) 85%-70% (20')];

$^1$H NMR (300 Mhz, $CDCl_3$): δ 6.54 (dd, $J_1$=4.4 Hz, $J_2$=8.4 Hz, 1H), 6.44 (s, 1H), 4.12 (d, J=2.4 Hz, 1H), 4.04 (d, J=2.4 Hz, 1H), 4.00 (s, 3H), 3.87 (bs, 1H), 3.65 (ddd, $J_1$=1.5 Hz, $J_2$=8.7 Hz, $J_3$=9.9 Hz, 1H), 3.35 (br. D, J=8.4 Hz, 1H), 3.15-2.96 (m, 4H), 2.92 (q, J=7.2 Hz, 1H), 2.47 (d, J=18.3 Hz, 1H), 2.29 (s, 3H), 2.18 (s, 3H) 1.83 (s, 3H), 1.64 (ddd, $J_1$=2.7 Hz, $J_2$=11.1 Hz, $J_3$=14.1 Hz, 1H), 0.79 (d, J=7.2 Hz, 3H);

$^{13}$C NMR (75 Mhz, $CDCl_3$): δ 186.0 (q), 175.9 (q), 156.2 (q), 146.8 (q), 142.8 (q), 140.7 (q), 136.6 (q), 130.5 (q), 128.8 (q), 127.0 (q), 120.5 (s), 117.4 (q), 116.5 (q), 60.8 (t), 60.4 (s), 58.7 (t), 56.2 (s), 55.7 (s), 54.8 (s), 54.8 (s), 54.4 (s), 50.0 (s), 41.6 (t), 39.8 (d), 25.2 (d), 24.4 (d), 21.2 (t), 15.5 (t), 8.4 (t).

ESI-MS m/z: Calcd for $C_{29}H_{35}N_5O_6$: 549.6. Found $(M+Na)^+$: 572.3.

Example D

A medium (50 l) composed of dextrose (2%), mannitol (4%), dry brewer's yeast (2%), ammonium sulphate (1%), potassium secondary phosphate (0.04%), potassium chloride (0.8%), iron (III) chloride 6-hydrate (0.001%), L-tyrosine (0.1%), calcium carbonate (0.8%), poly-(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM BP-14) and aerated cultivation under agitation was carried out at 27° C. to 24° C. for 64 hours (aeration of 75 l per minute and agitation from 350 to 500 rpm). The pH was controlled by automatic feeding of diluted sulphuric acid from 27 hours to final process. A 2% mannitol was added from 16 hours to final process. The cultured medium (45 l) thus obtained was, after removal of cells by centrifugation, adjusted to pH 9.5 with diluted sodium hydroxide, extracted with 25 litres of ethyl acetate twice. The mixture was carried out into an agitated-vessel at 8° C. for 20 minutes. The two phases were separated by a liquid-liquid centrifuge. The organic phases were frozen at −20° C. and filtered for removing ice and evaporated ice and evaporated until obtention of a 40 g oil-dark-crude extract. After introduction of the cyanide group and purification, 3.0 grams of safracin B cyano were obtained.

Example E

A medium (50 l) composed of dextrose (2%), mannitol (4%), dry brewer's yeast (2%), ammonium sulphate (1%), potassium secondary phosphate (0.02%, potassium chloride (0.2%), Iron (III) chloride 6-hydrate (0.001%, L-tyrosine (0.1%), calcium carbonate (0.8%, poly-(propylene glycol) 2000 (0.05%) and antifoam ASSAF 1000 (0.2%) was poured into a jar-fermentor with 75 l total capacity and, after sterilisation, inoculated with seed culture (2%) of A2-2 strain (FERM BP-14) and aerated cultivation under agitation was carried out at 27° C. to 24° C. for 41 hours (aeration of 75 l per minute and agitation from 350 to 500 rpm). The pH was controlled by automatic feeding of diluted sulphuric acid from 28 hours to final process. A 1% mannitol was added from 16 hours to final process. The cultured medium (45 l) thus obtained was, after removal of cells by centrifugation, adjusted to pH 3.9 with 200 ml of conc. acetic acid. 25 grams of potassium cyanide 97% were added and after 1 hour of agitation at 20° C., the pH was adjusted to 9.5 with 1500 ml of a solution 10% sodium hydroxide. Then, extracted with 35 litres of ethyl acetate. The mixture was carried out into an agitated-vessel at 8° C. for 20 minutes. The two phases were separated by a liquid-liquid centrifuge. The organic phase was dried by sodium sulphate anhydrous and evaporated until obtention of a 60 g oil-dark-crude extract.

After chromatography, 4.9 grams of safracin B cyano were obtained.

REFERENCES

European Patent 309,477.
U.S. Pat. No. 5,721,362.
Sakai, R., Jares-Erijman, E. A., Manzanares, I., Elipe, M. V. S., and Rinehart, K. L. J. Am. Chem. Soc. (1996) 118, 9017-9023
Martinez, E. J., Owa, T., Schreiber, S. L. and Corey, E. J. *Proc. Natl. Acad. Sci. USA,* 1999, 96, 3496-3501.
Japanese Kokai JP-A2 59/225189.
Japanese Kokai JP-A2 60/084,288.
Arai, T,; Kubo, A. In *The Alkaloids, Chemistry and Pharmacology*; Brossi, A. Ed.; Academic: New York, 1983, Vol 21; pp 56-110.
Remers, W. A.: In *The Chemistry of Antitumor Antibiotics*; Vol. 2; Wiley; New York, 1988, pp 93-118.
Gulavita N. K.; Scheuer, P. J.: Desilva, E. D. Abst. Indo-United States Symp. on Bioactive Compounds from Marine Organisms, Goa, India, Feb. 23-27, 1989, p 28.
Arai, T; Takahashi, K; Kubo, A. *J. Antibiot,* 1977, 30, 1015-1018.
Arai. T.; Takahashi, K.; Nakahara, S.; Kubo, A. *Experientia* 1980, 36, 1025-1028.
Mikami, Y.; Takahashi, K; Yazawa, K.; Hour-Young, C.; Arai, T.; Saito, N.; Kubo, A. *J. Antibiot.* 1988, 41, 734-740.
Arai, T.; Takahashi, K.; Ishiguro, K.; Yazawa, K. *J. Antibiot.* 1980, 33, 951-960.
Yazawa, K.; Takahashi, K.; Mikami, Y.; Arai, T.; Saito, N.; Kubo, A. *J. Antibiot.* 1986, 39, 1639-1650.
Arai, T.; Yazawa, K.; Takahashi, K.; Maeda, A.; Mikami, Y. *Antimicrob. Agent Chemother.* 1985, 28, 5-11.
Takahashi, K.; Yazawa, K.; Kishi, K.; Mikami, Y.; Arai, T.; Kubo, A. *J. Antibiot.* 1982, 35, 196-201.
Yazawa, K.; Asaoka, T.; Takahashi, K.; Mikami, Y.; Arai, T. *J. Antibiot.* 1982, 35, 915-917.
Frincke, J. M.; Faulkner, D. J. *J. Am. Chem. Soc.* 1982, 104, 265-269.
He, H.-Y.; Faulkner, D. J. *J. Org. Chem.* 1989, 54, 5822-5824.
Kubo, A.; Saito, N.; Kitahara, Y.; Takahashi, K.; Tazawa, K.; Arai, T. *Chem. Pharm. Bull.* 1987, 35, 440-442.
Trowitzsch-Kienast, W.; Irschik, H.; Reichenback, H.; Wray, V.; Hofle, G. *Liebigs Ann. Chem.* 1988, 475-481.
Ikeda, Y.; Idemoto, H.; Hirayama, F.; Yamamoto, K.; Iwao, K.; Asano, T.; Munakata, T. *J. Antibiot.* 1983, 36, 1279-1283.
Asaoka, T.; Yazawa, K.; Mikami, Y. Arai, T.; Takahashi, K. *J. Antibiot.* 1982, 35, 1708-1710.
Lown, J. W.; Hanstock, C. C.; Joshua, A. V.; Arai, T; Takahashi, K. *J. Antibiot.* 1983, 36, 1184-1194.
Munakata et al. U.S. Pat. No. 4,400,752, 1984.
Y. Ikeda et al. The Journal of Antibiotics. VOL XXXVI, No 10, 1284, 1983.
R. Cooper, S. Unger. The Journal of Antibiotics. VOL XXX-VIII, No 1, 1985.
Corey et al. U.S. Pat. No. 5,721,362. 1998.
Corey et al. J. Am. Chem. Soc. vol 118 pp 9202-92034, 1996.
Proc. Natl. Acad. Sci. USA. Vol. 96, pp 3496-3501 1999

The invention claimed is:
1. The compound of formula

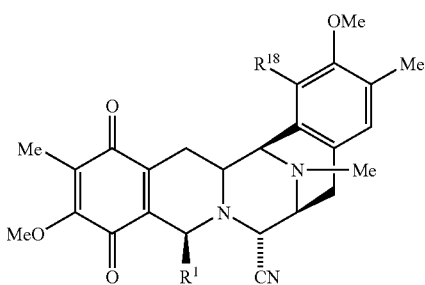

where R¹ is:
 (i) an unsubstituted aminomethylene group; or
 (ii) an aminomethylene group, wherein the amino portion of the aminomethylene group is protected with a protecting group selected from alkyl, alkenyl, alkylsilylalkoxyalkyl, alkoxyalkyl, cyanoalkyl, alkoxyarylalkyl, cycloalkyl, nitroaryl, arylalkyl, and hydroxyarylalkyl; or
 (iii) an N-acylated aminomethylene group, wherein the acyl portion of the N-acylated aminomethylene group is aroyl, arylaroyl, haloaroyl, nitroaroyl, or an acyl group of the formula —CO—R$^a$ where R$^a$ is selected from alkyl, alkoxy, alkenyl, arylalkyl, arylalkenyl, aminoacid, and heterocyclyl, each of which is optionally substituted with halo, cyano, nitro, carboxyalkyl, alkoxy, aryl, aryloxy, heterocyclyl, heterocyclyloxy, alkyl, amino or substituted amino; and
 R$^{18}$ is an OH group protected in the form of an alkyl ether, an alkoxyalkyl ether, an aryloxyalkyl ether, an alkoxyalkoxyalkyl ether, an alkylsilylalkoxyalkyl ether, an alkylthioalkyl ether, an arylthioalkyl ether, an azidoalkyl ether, a cyanoalkyl ether, a chloroalkyl ether, a heterocyclic ether, a cycloalkylalky ether, an alkenyl ether, a cycloalkyl ether, an alkylarylalkyl ether, an alkoxyarylalkyl ether, a nitroarylalkyl ether, a haloarylalkyl ether, an alkylaminocarbonylarylalkyl ether, an alkylsulfinylarylalkyl ether, or an alkylsilyl ether.

2. The compound according to claim 1, which is of formula:

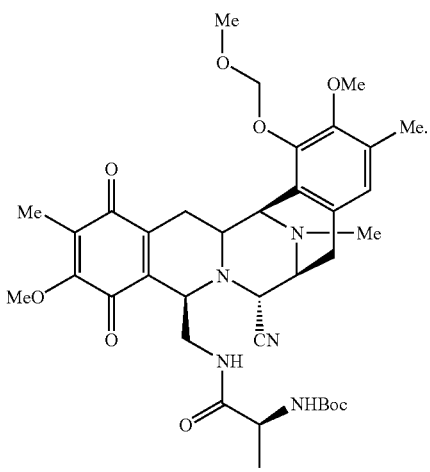

3. The compound of formula

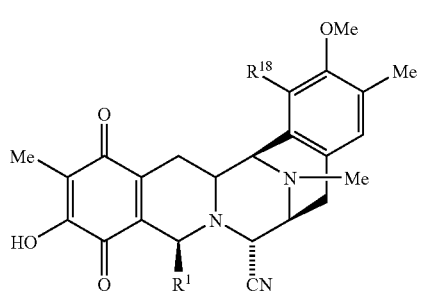

where R¹ is:
 (i) an unsubstituted aminomethylene group; or
 (ii) an aminomethylene group, wherein the amino portion of the aminomethylene group is protected with a protecting group selected from alkyl, alkenyl, alkylsilylalkoxyalkyl, alkoxyalkyl, cyanoalkyl, alkoxyarylalkyl, cycloalkyl, nitroaryl, arylalkyl, and hydroxyarylalkyl; or (iii) an N-acylated aminomethylene group, wherein the acyl portion of the N-acylated aminomethylene group is aroyl, arylaroyl, haloaroyl, nitroaroyl, or an acyl group of the formula —CO—R$^a$ where R$^a$ is selected from alkyl, alkoxy, alkenyl, arylalkyl, arylalkenyl, aminoacid, and heterocyclyl, each of which is optionally substituted with halo, cyano, nitro, carboxyalkyl, alkoxy, aryl, aryloxy, heterocyclyl, heterocyclyloxy, alkyl, amino or substituted amino; and R$^{18}$ is a protected hydroxy group, wherein the oxygen atom together with the protecting group form:

(a) an ether selected from an alkyl ether, an alkoxyalkyl ether, an aryloxyalkyl ether, an alkoxyalkoxyalkyl ether, an alkylsilylalkoxyalkyl ether, an alkylthioalkyl ether, an arylthioalkyl ether, an azidoalkyl ether, a cyanoalkyl ether, a chloroalkyl ether, a heterocyclic ether, a cycloalkylalky ether, an alkenyl ether, a cycloalkyl ether, an alkylarylalkyl ether, an alkoxyarylalkyl ether, a nitroarylalkyl ether, a haloarylalkyl ether, an alkylaminocarbonylarylalkyl ether, an alkylsulfinylarylalkyl ether, and an alkylsilyl ether; or
 (b) arylacyloxy, aryl alkyl carbonate, aliphatic carbonate, alkylsulfinylarylalkyl carbonate, alkyl carbonate, aryl haloalkyl carbonate, aryl alkenyl carbonate, arylcarbamate, alkylphosphinyl, alkylphosphinothioyl, or aryl alkyl sulphonate.

4. The compound according to claim 3, which is of the formula:

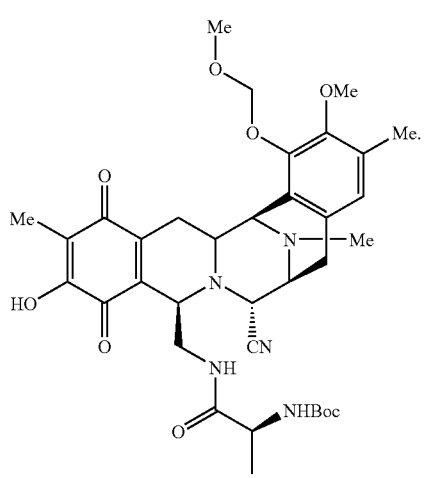

5. The compound of formula:

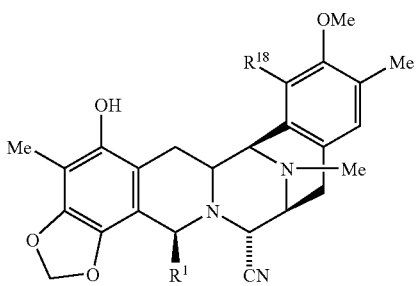

where $R^1$ is:
(i) an aminomethylene group, wherein the amino portion of the aminomethylene group is protected with a protecting group selected from alkyl, alkenyl, alkylsilylalkoxyalkyl, alkoxyalkyl, cyanoalkyl, alkoxyarylalkyl, cycloalkyl, nitroaryl, arylalkyl, and hydroxyarylalkyl; or
(ii) an N-acylated aminomethylene group, wherein the acyl portion of the N-acylated aminomethylene group is an acyl group of the formula —CO—$R^a$ where $R^a$ is selected from alkyl, alkoxy, alkenyl, arylalkenyl, aminoacid, and heterocyclyl, each of which is optionally substituted with halo, cyano, nitro, carboxyalkyl, alkoxy, aryloxy, heterocyclyl, heterocyclyloxy, alkyl, amino or substituted amino; and
$R^{18}$ is a protected hydroxy group, wherein the oxygen atom together with the protecting group form:
(a) an ether selected from an alkyl ether, an alkoxyalkyl ether, an aryloxyalkyl ether, an alkoxyalkoxyalkyl ether, an alkylsilylalkoxyalkyl ether, an alkylthioalkyl ether, an arylthioalkyl ether, an azidoalkyl ether, a cyanoalkyl ether, a chloroalkyl ether, a heterocyclic ether, a cycloalkylalky ether, an alkenyl ether, a cycloalkyl ether, an alkylarylalkyl ether, an alkoxyarylalkyl ether, a nitroarylalkyl ether, a haloarylalkyl ether, an alkylaminocarbonylarylalkyl ether, an alkylsulfinylarylalkyl ether, and an alkylsilyl ether; or
(b) arylacyloxy, aryl alkyl carbonate, aliphatic carbonate, alkylsulfinylarylalkyl carbonate, alkyl carbonate, aryl haloalkyl carbonate, aryl alkenyl carbonate, arylcarbamate, alkylphosphinyl, alkylphosphinothioyl, or aryl alkyl sulphonate.

6. The compound according to claim 5, which is of the formula:

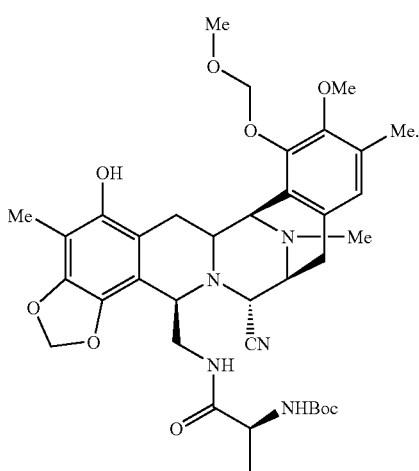

* * * * *